US012102063B2

(12) United States Patent
Lee et al.

(10) Patent No.: US 12,102,063 B2
(45) Date of Patent: *Oct. 1, 2024

(54) APPLICATION OF DRY HYDROGEN PEROXIDE (DHP) GAS TO METHODS OF POULTRY PRODUCTION

(71) Applicant: SYNEXIS LLC, Kansas City, MO (US)

(72) Inventors: James D. Lee, Kansas City, MO (US); James Russell Stephens, Kennesaw, GA (US)

(73) Assignee: Synexis, LLC, Lenexa, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/733,140

(22) Filed: Apr. 29, 2022

(65) Prior Publication Data
US 2022/0354094 A1 Nov. 10, 2022

Related U.S. Application Data

(62) Division of application No. 15/866,208, filed on Jan. 9, 2018, now abandoned.

(60) Provisional application No. 62/444,180, filed on Jan. 9, 2017.

(51) Int. Cl.
| A01K 41/04 | (2006.01) |
| A01K 1/00 | (2006.01) |
| A01K 31/18 | (2006.01) |
| A01K 41/02 | (2006.01) |
| A01K 41/06 | (2006.01) |
| A01K 45/00 | (2006.01) |

(Continued)

(52) U.S. Cl.
CPC ............ *A01K 41/04* (2013.01); *A01K 1/0047* (2013.01); *A01K 31/18* (2013.01); *A01K 41/023* (2013.01); *A01K 41/06* (2013.01); *A01K 45/007* (2013.01); *A61L 2/208* (2013.01); *A61L 9/015* (2013.01); *A61L 2209/16* (2013.01); *A61L 2209/211* (2013.01)

(58) Field of Classification Search
USPC ...... 119/300–348, 6.5, 6.6, 6.8, 174; 422/28
See application file for complete search history.

(56) References Cited

U.S. PATENT DOCUMENTS

| 3,006,320 A | 10/1961 | Bailey |
| 3,148,649 A | 9/1964 | Moore et al. |
| 3,364,037 A | 1/1968 | Mink et al. |

(Continued)

FOREIGN PATENT DOCUMENTS

| CN | 1075604 A | 9/1993 |
| CN | 101854958 A | 10/2010 |

(Continued)

OTHER PUBLICATIONS

Samberg et al., "Application of disinfectants in poultry hatcheries," Rev. Sci. Tech. Off. Int. Epiz., 14(2):365-380 (1995) Poultry Res. 2:1-6 (1993).*

(Continued)

*Primary Examiner* — Andrea M Valenti
(74) *Attorney, Agent, or Firm* — Hovey Williams LLP

(57) ABSTRACT

An improved poultry production method comprising providing dry hydrogen peroxide (DHP) to poultry eggs, chicks and birds, and devices for providing DHP to poultry production during laying, incubating, hatching, and growing.

13 Claims, 21 Drawing Sheets

(51) Int. Cl.
*A61L 2/20* (2006.01)
*A61L 9/015* (2006.01)

(56) References Cited

U.S. PATENT DOCUMENTS

| | | | |
|---|---|---|---|
| 4,932,359 A * | 6/1990 | Sheldon | A01K 43/005 119/6.8 |
| 5,410,958 A | 5/1995 | Schritz | |
| 5,868,998 A | 2/1999 | Larose et al. | |
| 6,126,722 A | 10/2000 | Mitchell et al. | |
| 6,196,160 B1 | 3/2001 | Pas | |
| 6,964,788 B2 | 11/2005 | Phebus et al. | |
| 7,407,624 B2 | 8/2008 | Cumberland et al. | |
| 7,861,673 B2 | 1/2011 | Huisinga et al. | |
| 7,988,923 B2 | 8/2011 | Fink et al. | |
| 8,012,412 B2 | 9/2011 | Normark et al. | |
| 8,168,122 B2 | 5/2012 | Lee | |
| 8,685,329 B2 | 4/2014 | Lee | |
| 8,877,046 B2 | 11/2014 | Ellis | |
| 9,283,295 B2 | 3/2016 | Fink et al. | |
| 9,295,746 B2 | 3/2016 | Ellis | |
| 9,433,691 B2 | 9/2016 | Eide et al. | |
| 9,839,901 B2 | 12/2017 | Ellis et al. | |
| 10,232,076 B2 | 3/2019 | Lee et al. | |
| 2001/0046500 A1 | 11/2001 | Jongsma et al. | |
| 2003/0047087 A1 | 3/2003 | Phebus et al. | |
| 2004/0175391 A1 | 9/2004 | Schasteen et al. | |
| 2005/0051104 A1 | 3/2005 | Wolfe | |
| 2005/0175500 A1 | 8/2005 | Adams et al. | |
| 2005/0226764 A1 | 10/2005 | Moirandat et al. | |
| 2006/0008379 A1 | 1/2006 | Mielnik et al. | |
| 2006/0196428 A1 | 9/2006 | Correa et al. | |
| 2006/0210674 A1 | 9/2006 | Ruff et al. | |
| 2007/0245973 A1 | 10/2007 | Huisinga et al. | |
| 2008/0274012 A1 | 11/2008 | Cumberland et al. | |
| 2009/0007853 A1 | 1/2009 | Johnson et al. | |
| 2009/0041617 A1 | 2/2009 | Lee | |
| 2010/0150958 A1 | 6/2010 | Sheppard | |
| 2010/0183782 A1 | 7/2010 | Marsden et al. | |
| 2010/0323072 A1 | 12/2010 | Bernstein et al. | |
| 2011/0123394 A1 | 5/2011 | Plantinga et al. | |
| 2011/0182772 A1 | 7/2011 | Holt | |
| 2011/0182773 A1 | 7/2011 | Holt | |
| 2011/0183598 A1 | 7/2011 | Holt | |
| 2011/0286881 A1 | 11/2011 | Marsden et al. | |
| 2013/0084215 A1 | 4/2013 | Fukui et al. | |
| 2013/0116174 A1 | 5/2013 | Hargis et al. | |
| 2013/0164385 A1 | 6/2013 | Shannon et al. | |
| 2014/0238308 A1 | 8/2014 | Foreman et al. | |
| 2015/0083051 A1 | 3/2015 | Foreman et al. | |
| 2015/0196675 A1 | 7/2015 | Lee | |
| 2015/0313964 A1 | 11/2015 | Cook et al. | |
| 2017/0263436 A1 | 9/2017 | Brown et al. | |
| 2019/0056122 A1 * | 2/2019 | Lee | A61L 2/208 |
| 2020/0368713 A1 | 11/2020 | Holt | |
| 2021/0038755 A1 | 2/2021 | Eide | |
| 2021/0228762 A1 | 7/2021 | Eide et al. | |
| 2021/0346565 A1 | 11/2021 | Woodbridge | |

FOREIGN PATENT DOCUMENTS

| | | | |
|---|---|---|---|
| CN | 102308761 B | 3/2013 | |
| CN | 105813659 A | 7/2016 | |
| CN | 105941189 A | 9/2016 | |
| CN | 109589441 A1 | 4/2019 | |
| EP | 2644282 A1 | 10/2013 | |
| JP | 2009-527241 A | 7/2009 | |
| WO | 2007/096417 A2 | 8/2007 | |
| WO | 2009021108 A1 | 2/2009 | |
| WO | 2010/093796 A1 | 8/2010 | |
| WO | WO 2010/093796 * | 8/2010 | A61L 9/20 |
| WO | 2012161685 A1 | 11/2012 | |
| WO | 2014186805 A1 | 11/2014 | |
| WO | 2015026958 A1 | 2/2015 | |
| WO | 2015171633 A1 | 11/2015 | |
| WO | 2016172223 A1 | 10/2016 | |
| WO | 2016176486 A1 | 11/2016 | |
| WO | 2018/129537 A2 | 7/2018 | |
| WO | 2020/077263 A1 | 4/2020 | |

OTHER PUBLICATIONS

Short periods of incubation during egg storage increase hatchability and chick quality in long-stored broiler eggs, by Dymond et al, Poultry Science, vol. 92, Issue 11, Nov. 1, 2013, pp. 2077-2987 [retrieved from internet Nov. 7, 2023 https://www.sciencedirect.com/science/article/pii/S0032579119384123].*

Part 1: The Evolution of Hydrogen Peroxide Gas Technologies, by Steris University; Feb. 22, 2016; 5 pages [retrieved from internet Dec. 17, 2019, https://university.steris.com/resources/the-evolution-of-hydrogen peroxide-gas-technologies-part1/].

PoultryWorld, Eggs, 7 pages, retrieved from internet on Jul. 29, 2019 [https://www.poultryworld.net/Eggs/Articles/2016/1/Restoring-the-hatchability-of-stored-eggs-1726859W/] Jan. 15, 2016.

Marsden et al., In view of Proudfoot et al., "Care of Hatching Eggs Before Incubation," Agriculture Canada, Publication 1573/E (1990).

Banwell, "Restoring the hatchability of stored eggs," Poultry World, published online on Jan. 15, 2016.

Anderson, "Time to Think About Hot Weather Management," North Carolina Poultry Industry Joint Area Newsletter, NC State University, North Carolina Cooperative Extension Service, 2006.

Bing et al., "The synergistic effects of slightly acidic electrolyzed water and UV-C light on the inactivation of *Salmonella enteritidis* on contaminated eggshells," Poultry Science 98: 6914-6920, 2019.

Block, "Peroxygen Compounds" Sterilants, Disinfectants, and Antiseptics A. by Chemical Type, 187-191, 2001.

Cantu et al., "Effectiveness of Duck Hatching Eggs Sanitization with the Combination of Hydrogen Peroxide and Ultraviolet Light," J. Appl. Poult. Res. 28: 301-306, 2019.

Gottselig, "Microbial Reduction on Eggshell Surfaces By the Use of Hydrogen Peroxide and Ultraviolet Light," Texas A&M University, Masters Thesis, 2011.

Hrncar et al., "The Effect of Disinfection of Hatching Eggs on Hatchability of Oravka Chickens," Scientific Papers, Animal Science and Biotechnologies, 45(2), 2012.

Hultman et al., "The Physical Chemistry of Decontamination with Gaseous Hydrogen Peroxide," Pharmaceutical Engineering, 2007.

Ikai et al., "Photolysis of Hydrogen Peroxide, an Effective Disinfection System via Hydroxyl Radical Formation," Antimicrobial Agents and Chemotherapy, 54(12), 5086-2091, 2010.

Kacer et al., "Vapor Phase Hydrogen Peroxide—Method for Decontamination of Surfaces and Working Areas from Organic Pollutants," Organic Pollutants Ten Years After the Stockholm Convention—Environmental and Analytical Update, 399-460.

McKenzie, "Peroxygens," Disinfectant Actives Review, Part 2 of 5: "Quats," Poultry Overlook, 2017.

Melo et al., "An evalutaion of alternative methods for sanitizing hatching eggs," Poultry Science Association Inc., 2466-2473, 2019.

Patrzalek et al., "Preliminary evaluation of application of a 3-dimensional network structure of siloxanes Dergall preparation on chick embryo development and microbiological status of eggshells," Poultry Science, 99: 1581-1590, 2020.

Rehkopf et al., Advanced Oxidation Process sanitization of hatching eggs reduces *Salmonella* in Broiler Chicks,: Poultry Science, 96: 3709-3716, 2017.

Samberg et al.,, "Application of disinfectants in poultry hatcheries," Rev. sci. tech. Off. Int. Epiz., 14(2): 365-380, 1995.

Scott et al., "Screening Sanitizing Agents and Methods of Application for Hatching Eggs I. Environmental and User Friendliness," J. Appl. Poultry Res. 2:1-6 (1993).

Scott et al., "Screening Sanitizing Agents and Methods of Application for Hatching Eggs II. Effectiveness Against Microorganisms on the Egg Shell," J. Appl. Poultry Res. 2:7-11 (1993).

Scott et al., "Screening Sanitizing Agents and Methods of Application for Hatching Eggs III Effect of Concentration and Exposure Time on Embryo Viability," J. Appl. Poultry Res. 2: 12-18 (1993).

(56) References Cited

OTHER PUBLICATIONS

Van Den Brand et al., "Management and Production: Effects of floor eggs on hatchability and later life performance in broiler chickens," Poultry Science 95: 1025-1032 (2016).
Whistler et al., "Bacterial Activity, Eggshell Conductance, and Hatchability Effects of Ozone Versus Formaldehyde Disinfection," Poultry Science 68: 1074-1077 (1989).
Wineland, "Spray Sanitizing Hatching Eggs," downloaded from https://www.ces.ncsu.edu/depts/poultsci/tech_manuals/spray_sanitizing.htm, 2018.
Zeweil et al., "Comparing the effectiveness of egg disinfectants against bacteria and mitotic indices of developing chick embryos," The Journal of Basic & Applied Zoology, 70: 1-15 (2015).
Gruhn et al., "Sterilisation von Hühnereievn zur Impfstoffproduktion mit Wasserstoffperoxid in der Gasphase," Pharmazeutische Industrie, 57 (10):873-877 (1995).
Climaco et al., "Eggshell microbiology and quality of hatching eggs subjected to different sanitizing procedures," *Pesq. agropec. bras. Brasilia*, 53(10):1177-1183 (2018).
Keita et al., "A multi-pronged approach to the search for an alternative to formaldehyde as an egg disinfectant without affecting worker health, hatching, or broiler production parameters," Poultry Science, 95(7):1609-1616 (2016).
Musgrove et al., "Effect of inoculation and application methods on the performance of chemicals used to disinfect *Salmonella*-contaminated broiler hatching eggs," J. Appl. Poult. Res. 19: 387-392 (2010).
Tebrun et al., "Preliminary study: Health and performance assessment in broiler chicks following application of six different hatching egg disinfection protocols," PloS one 15(5):e0232825 (2020).
Zhelev and Lazarov, "Efficacy of Ultra-Low Volume Disinfection With Hydrogen Peroxide Vapour in a Poultry Hatchery," Trakia Journal of Sciences, 17(4):340-345 (2019).
"Hydrogen Peroxide Handbook," Chemical and Material Sciences Department, Rocketdyne, a Division of North American Aviation, Inc., Canoga Park, California (1967).
International Search Report dated Jul. 5, 2018, in international patent application No. PCT/US2018/012984.
"Ozone Generators that are Sold as Air Cleaners," downloaded from the United States EPA website (2018).
Pinto, "Hydroxyl Radicals—Hype or Reality," downloaded from www.OzoneExperts.com (2018).
Proudfoot et al., "Effect of Pre-Incubation Fumigation with Formaldehyde on the Hatchability of Chicken Eggs," Can. J. Anim. Sci. 50:453-465 (1970).
Adams, "Vector Abatement Plan—Darling Beetles," CAMM Poultry, Chapter 10c: 10c.1-10.c.12 (2003).
Agalloco et al., "Overcoming Limitations of Vaporized Hydrogen Peroxide," Pharmaceutical Technology, 37(9):1-7 (2013).
Bailey et al., "Effect of Hatching Cabinet Sanitation Treatments on *Salmonella* Cross-Contamination and Hatchability of Broiler Eggs," Poult Sci. 75(2): 191-6 (1996).
Bakst et al., "Impact of Egg Storage on Embryo Development," Proceedings of the International Congress on Bird Reproduction 125-131 (1999).
Bauer et al., "Output and Aerosol Properties of 5 Nebulizer/Compressor Systems with Arformoterol Inhalation Solution," Respiratory Care, 54(10):1342-1347 (2009).
Bergoug, "Effect of pre-incubation and incubation conditions in hatchability, hatch time and hatch window, and effect of post hatch handling on chick quality at placement," World's Poultry Science Journal, (2013).
Berrang et al., "Hatching Egg Sanitization for Prevention or Reduction of Human Enteropathogens: A Review," J. Appl. Poul Res. 279-284 (2000).
Bialka et al., "Efficacy of Electrolyzed Oxidizing Water for the Microbial Safety and Quality of Eggs," Poultry Science 83:2071-2078 (2004).
Boerjan, "Programs for Single Stage Incubation and Chick Quality," Avian Poultry Biology Reviews 13:237-238 (2002).
Boerjan, "Incubation for Uniformity," Aust. Poult. Sci. Symp, 18:174-181 (2006).
Boerjan, "A practical interpretation of 'physiological zero' in hatchery management," Pas Reform Incubation Guide 5.2 or 6.0 (2016).
Bourassa et al., "Elevated Egg Holding-Room Temperature of74° F. (23° C.) Does Not Depress Hatchability or Chick Quality," JAPR: Research Report, Poultry Science Association, Inc. (2003).
Butcher et al., "A Systematic Approach to Solving Hatchability and Chick Quality Problems," IF AS Extension, University of Florida, VMI 36: 1-3 (2002).
Carver, "Internal Parasites," downloaded from https://www.ces.ncsu.edu/ degts/goulsci/tech manuals/internal garas itespdf (2014).
Soares, et al., "Reduced productivity among confined laying hens infested by Allopsoroptoides galli (Mironov, 2013)," Poult. Sci. 95(4):819-22 (2016).
Spray Sanitizing Hatching Eggs from the North Carolina Cooperative Extension Service available on the Web downloaded from www.ces.ncsu.edu/de12ts/12oulsci/tech manuals/s12ray sanitizing.html (2018).
Strother, "Poultry pest management," Publ. No. ARN-483. Alabama Cooperative Extension System. Auburn University (2008).
Summers, "Hydrogen Peroxide H20 2," Poultry Industry Counsel Fact Sheet #12, Hydrogen peroxide Poultry Industry Council of Canada (1991).
Tabler et al., "Arkansas Turkey Growers Face Variety of Challenges," Avian Advice 6(1) (2004).
Tabler et al., "Mortality Patterns Associated with Commercial BroilerProduction," Avian Advice, 6(1): I-3 (2004).
Tabler et al., "Odor and Air Emissions From Poultry Facilities," Avian Advice 6(1) (2004).
Tabler et al., "Odor—An Emerging Concern for Producers," Avian Advice 8(1) (2006).
Tabler, "Factors Affecting Turkey Flock Performance," Avian Advice 8(1) (2006).
Tabler, "Farm Animal Welfare Issues Affect Poultry Producers," Avian Advice 8(1) (2006).
Tabler, "A 100-Flock Comparison of Broiler Feed Ticket Weights and On-Farm Feed Weights at the ABRF," Avian Advice 11(2) (2009).
Tabler et al., "Poultry Litter Production and Associated Challenges," Avian Advice 11 (2) (2009).
Tona et al., "Effects of Egg Storage Time on Spread of Hatch, Chick Quality, and Chick Juvenile Growth," Poultry Science 82:736-741 (2003).
"U.S. Broiler and Egg Production Cycles," NASS Factor Finders for Agriculture, United Statements Department of Agriculture, Washington, DC (2005).
Van de Ven et al., "Significance of chick quality score in broiler production," Animal 6(10):1677-1683 (2012).
Vezzoli et al., "The effect of northern fowl mite (*Ornithonyssus sylviarum*) infestation on hen physiology, physical condition, and egg quality," Poult. Sci. 95(5):1042-9 (2016).
Walker, "Parasite Control in Poultry," Melbourne Bird Veterinary Clinic (2015).
Walls et al., "Effects fo Incubation Delay on Viability and Microbial Growth of Wood Duck (*Aix sponsa*) Eggs," The Auk 128:(4):663. 670 (2011).
Wan et al., "Differential Gene Expression Patterns in Chicken Cardiomyocytes during Hydrogen Peroxide-Induced Apoptosis," PLoS One I 1(1):e0147950 (2016).
Warin, "Embryonic Development," Ceva Animal Health Asia Pacific Newsletter, issue 7 (2006).
Watkins et al., "Water Sanitation: Evaluation of Products," Avian Advice 6(1) (2004).
Watkins et al., "Broiler Water Consumption," Avian Advice 11(2) (2009).
Wells et al., "Disinfection of eggshells using ultraviolet light and hydrogen peroxide independently and in combination," Poult Sci. 89(11):2499-505 (2010).
Wells et al., "Hatchability of Broiler Breeder Eggs Sanitized with a Combination of Ultraviolet Light and Hydrogen Peroxide," International Herewith Journal of Poultry Science 10(4):320-324 (2011).

(56) References Cited

OTHER PUBLICATIONS

Whistler et al., "Biocidal Activity of Ozone Versus Formaldehyde Against Poultry Pathogens Inoculated in a Prototype Setter," Poultry Science Herewith 68:1068-1073 (1989).
Willemsen et al., "Critical Assessment of Chick Quality Measurements as in Indicator of Posthatch Performance," Poultry Science 87:2358-2366 (2008).
Wilson, "Hatching Egg Sanitation," University of Florida, If As Extension, Herewith p. S22 (2003).
Wineland et al., "Microbiological Monitoring for a Hatchery QA Program," Poultry Science Facts from North Carolina State University at Raleigh/Extension Poultry Science (1992).
Wineland, "Contamination of Hatching Eggs," Poultry Science Facts #21 (1996).
Zhang et al., "A Highly Sensitive and Selective Hydrogen Peroxide Biosensor Based on Gold Nanoparticles and Three-Dimensional Porous Carbonized Herewith Chicken Eggshell Membrane," PLOS One 1-14 (2015).
Zheng et al., "Airborne bacterial reduction by spraying slightly acidic electrolyzed water in a laying-hen house," Journal of the Air & Waste Herewith Management Association 63(10): 1205/1211 (2013).
Choi et al., "Reduction of *Salmonella enterica* on the surface of eggshells by sequential treatment with aqueous chlorine dioxide and drying," Int. J. Food Microbial. 210:84-87 (2015).
Christensen et al., "Investigations into the survival of Mycoplasma gallisepticum, Mycoplasma synoviae and Mycoplasma iowae on materials found in the poultry house environment," Avian Pathol. 23(1):127-43 (1994).
Clark, "Two New Programs: Premises Identification and the National Animal Identification and the National Animal Identification System," Avian Advice, 7(2) (2005).
Cornelison et al., "Effects of Water Acidification on Turkey Performance," Avian Advice, 7(2) (2005).
Cox et al., "Bactericidal Treatment of Hatching Eggs I. Chemical Immersion Treatments and *Salmonella*," J. Applied Poultry Res. 347-350 (1998).
Cox et al., "Bactericidal Treatment of hatching Eggs II. Use of Chemical Applied with Vacuum and a Surfactant to Eliminate *Salmonella* from Hatching Eggs," J. Appl. Poult. Res. 9:530-534 (2000).
Cox et al. "Bactericidal Treatment of Hatching Eggs IV. Hydrogen Peroxide Applied with Vacuum and a Surfactant to Eliminate *Salmonella* from Hatching Eggs," J. Appl. Poult. Res. 9:530-534 (2000).
Cox et al., "*Salmonella* penetration of egg shells and proliferation in broiler hatching eggs—a review," Poult. Sci 79(11):1571-4 (2000).
Cox et al., "Bactericidal Treatment of Hatching Eggs V: Efficiency of Repetitive Immersions in Hydrogen Peroxide or Phenol to Eliminate Salmonella from Hatching Eggs," J. Appl. Poult. Res. 11 (3):328-331 (2002).
Decuypere et al., "The Endocrine Interface of Environmental and Egg Factors Affecting Chick Quality," Poult. Sci 86(5):1037-42 (2007).
Deloach et al., "Northern fowl mite, *Ornithonyssus sylviarum* (Acari: Macronyssidae) ingests large amounts of blood from white leghorn hens," J. Med. Entomol. 18:374-377 (1981).
Elibol et al., "Effect of Egg Weight and Position Relative to Incubator Fan on Broiler Hatchability and Chick Quality," Poultry Science, 1913-1918 (2008).
"Epidemiologic and Other Analyses of HP AI-Affected Poultry Flocks: Jun. 15, 2015 Report," (2015).
Ernst, "Hatching Egg Sanitation: The Key Step in Successful Storage and Production," ANR Publication 8120 (2004) available on the Web at anrcatalog.ucanr.edu/pdf/8120.pdf.
Ernst, "Common Incubation Problems: Causes and Remedies," ANR Publication 8127 (2004).
Fasenko, "Egg Storage and the Embry," Embryo Symposium, 1020-1024 (2001).
French, "Managing the Incubation Environment in Commercial Hatcheries to Meet the Requirements of the Embryo," Proceedings of the International Congress on Bird Reproduction 179-185 (1999).
"Hatchery Production 2015 Summary," USDA ISSN:1949-1976 (2016).
Henderson et al., "On-Farm Egg-Holding Temperatures for Commercial Broiler Breeders," Avidan Advice 8(1):3-6 (2006).
Huff et al., "Bacteriophage: A Replacement for Antibiotics?," Avian Advice 7(2) (2005).
Hughes et al., "Chlorination/ Acidification Affects *Salmonella* Contamination," Avian Advice 11 (2) (2009).
Humphrey et al., "Numbers of *Salmonella enteritidis* in the contents of naturally contaminated hens' eggs," Epidemiol. Infect. 106(3):489-496 (1991).
Humphrey et al., "*Salmonella enteritidis* Phage Type 4 Isolates More Tolerant of Heat, Acid, or Hydrogen Peroxide Also Survive Longer on Surfaces," Applied and Environmental Microbiology 61(8):3161-3164 (1995).
Hsieh et al., "Hydrogen peroxide treatment of eggshell membrane to control porosity," Food Chem. 141(3):2117-2121 (2013).
Ipek et al., "Broiler Chick Quality and Scoring Methods," Journal of Agricultural Faculty of Uludag Unversity, (2013).
Jones et al., "What are Bacteriophages?" Avian Advice 7(2) (2005).
Kahnert et al., "Decontamination with vaporized hydrogen peroxide is effective against *Mycobacterium tuberculosis*," Lett. Appl. Microbial. 40(6):448-52 (2005).
Kim et al., "Inactivation of *Salmonella* on Eggshells by Chlorine Dioxide Gas," Korean J. Food Sci. Anim. Resour. 36(1):100-108 (2016).
McDougald, Protozoa! Infections. In: Diseases of Poultry (ed. SaifYM), Iowa State Press, pp. 973-1026 (2003).
Mitchell et al., "Reducing Airborne Pathogens, Dust and *Salmonella* Transmission in Experimental hatching Cabinets Using an Electrostatic Space Charge System," Poultry Science 81 :49-55 (2002).
Molenaar, "Evaluation of Chick Quality, Which Method Do You Choose?" Hatch Tech B. V. (2011).
Mu et al., "Biphasic regulation of H2O2 on angiogenesis implicated NADPH oxidase," Cell Biol. Int. 34(10):1013-1020 (2010).
Mueller-Doblies et al. "A comparison of the efficacy of different disinfection methods in eliminating *Salmonella* contamination from turkey houses," J. Appl. Microbial. 109(2):471-479 (2010).
Naas et al., "Estimating the Impact of Environmental Conditions on Hatching Results Using Multivariable Analysis," Brazilian Journal of Poultry Science 10(4):215-222 (2008).
Oosterik et al., "Disinfection by hydrogen peroxide nebulization increases susceptibility to avian pathogenic *Escherichia coli*," BMC Res. Notes. 8:378 (2015).
Padron, "Egg dipping in hydrogen peroxide solution to eliminate *Salmonella typhimurium* from eggshell membranes," Avian Dis. 39(3):627-30 (1995).
Park et al., "Inactivation of *Salmonella enterica* in chicken feces on the surface of eggshells by simultaneous treatments with gaseous chlorine dioxide and mild wet heat," Food Microbial. 62:202-206 (2017).
Parkhurst et al., "Incubation and Hatchery Management," Poultry Meat and Egg Production 65-66 (1988).
Parks, "The Relationship Between Saturated Hydrogen Peroxide, Water Vapour and Temperature," Pharmaceutical Technology Europe (2004).
Patterson et al., "A respiratory chain controlled signal transduction cascade in the mitochondrial intermembrane space mediates hydrogen peroxide signaling," PNAS E5679-E5688 (2015).
Payne et al., "Evaluation of Litter Treatments on Salmonella Recovery in Poultry Litter," Avian Advice 7(2) (2005).
Poultry—Production and Value 2015 Summary, USDA ISSN:1949-1073 (2016).
Proudfoot et al., "Care of Hatching Eggs Before Incubation," Agriculture Canada, Publication 1573/E (1990).
Reijrink et al., "Influence of prestorage incubation on embryonic development, hatchability, and chick quality," Poultry Science 88:2649-2660 (2009).

(56) References Cited

OTHER PUBLICATIONS

Reijrink et al., "Influence of egg storage time and preincubation warming profile on embryonic development, hatchability, and chick quality," Poultry Science 89: 1225-1238 (2010).

Reijrink et al., "Influence of air composition during egg storage on egg characteristics, embryonic development, hatchability, and chick quality," Poultry Science 89: 1992-2000 (2010).

Reijrink et al., "Influence of egg warming during storage and hypercapnic incubation on egg characteristics, embryonic development, hatchability, and chick quality," Poultry Science 89:2470-2483 (2010).

Russell, "The Effect of Electrolyzed Oxidative Water Applied Using Electrostatic Spraying on Pathogenic and Indicator Bacteria on the Surface of Eggs," Poultry Science 82:158-162 (2003).

Sander et al., "Effect of hydrogen peroxide disinfection during incubation of chicken eggs on microbial levels and productivity," Avian Dis. 43(2):227-33 (1999).

Sheldon et al., "Hydrogen peroxide as an alternative hatching egg disinfectant," Poult. Sci. 70(5):1092-8 (1991).

\* cited by examiner

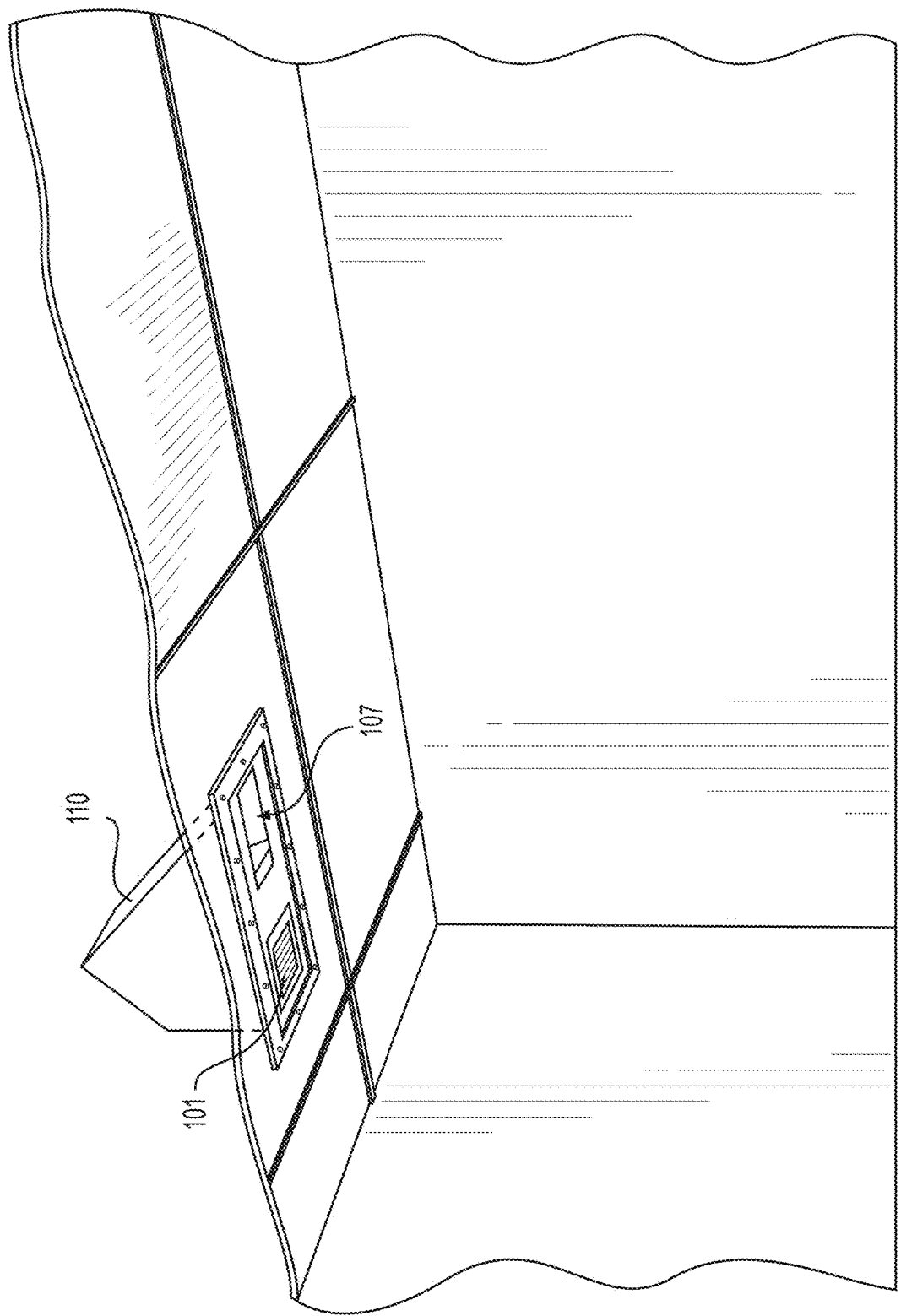

APPLICATION OF DRY HYDROGEN PEROXIDE (DHP) GAS TO METHODS OF POULTRY PRODUCTION

CROSS-REFERENCE TO RELATED PATENT APPLICATIONS

This patent application is a divisional of U.S. patent application Ser. No. 15/866,208, filed Jan. 9, 2018, which claims priority to U.S. Provisional Patent Application No. 62/444,180, filed Jan. 9, 2017, the contents of each of which are herein incorporated in their entirety.

FIELD OF THE INVENTION

The present disclosure relates to methods of poultry production in the presence of Dry Hydrogen Peroxide (DHP).

BACKGROUND OF THE INVENTION

In the U.S. in 2015, the poultry industry produced more than 8.5 billion broilers, nearly 100 billion eggs, and over 200 million turkeys. Poultry production is dispersed among all 50 states and the combined value in 2014 was $44.4 billion. There were 299 hatcheries in the US with capacity of over 900 million eggs per month. During 2015, more than 11 billion broiler eggs were set for incubation in hatcheries to yield about 9.2 billion hatched chicks, a loss of about 15%. Of the 9.3 billion hatched chicks, about 9.1 billion are placed into feeding operations (e.g., 97%). Thus, roughly 20% of the two billion eggs placed into hatcheries either fail to hatch or produce chicks that are of insufficient quality for being placed into feeding operations.

Poultry, primarily chickens but also including significant numbers of turkeys, quail, duck, and pheasant, are raised for a variety of reasons. Most poultry is raised for meat and eggs and is supported by a breeding and egg production backend for the continual replacement of layers and broilers. In addition to food production, poultry is also raised and kept as pets. In addition to providing eggs for hatching broilers and layers, eggs are used for table consumption and, importantly, vaccine production. In each situation, there is a need to reduce pathogens of all sorts.

As shown in FIG. 1, the process can be considered to begin with a primary breeding facility that produces several breeds of chickens (breeder chicks) that are provided to breeder farms. The breeder farms produce fertilized eggs that are provided to hatcheries to produce chicks that are in turn destined to be raised as layers (for egg production) and broilers. These breeder farms also provide eggs for hatching and raising by small private farmers and individuals to raise their own chickens and eggs as well as serve as pets. Egg farms maintain laying hens (as well as some roosters) and primarily produce eggs for table consumption and eggs for hatcheries for production of meat (e.g., broilers). Specialized egg farms produce eggs for vaccine production.

Modern poultry production methods generally are vertically integrated systems that include a feed mill which combines corn, soybean meal, and other ingredients, and provides the meal to the breeder farms, grow-out farms, and laying farms. At each stage of the breeding process, whether for broilers (meat) or for egg laying, the population is expanded from 100 to 150 fold. Often, the facilities and processes downstream of the primary breeders are integrated within a single producer and geographical area. Grow-out farms are often contracted by the integrated producer.

Primary breeder companies maintain flocks of inbred lines and provide breeder chicks to breeder farms (from great-grandparent eggs). A single male and 10 females can produce about 150 great-grandparent stock birds (GGP). The GGP birds are bred to produce about 7,500 grandparent (GP) birds that in turn produce 350,000 or so parent stock birds. Parent stock birds in turn produce about 48,000,000 eggs for broiler production (about 120 fold expansion). Breeder farms produce hatching eggs that are transported to the hatchery. After hatching, chicks are graded and sorted and sent to grow-out farms for the production of broilers. Finally, the broilers are sent to processing plants for slaughter, processing, and packaging.

For egg production, the process is similar though modern laying chickens are bred specifically for egg laying. Specialized breeders maintain pure breeding lines and produce hybrid crosses for grandparent stock production which expands the population 100 fold. The grandparent stock (hybrids) is crossed to produce the parent stock, expanding the population 100 fold again (10,000). The parent stock, which can comprise the contributions of four different lines, is used to produce the laying hens, expanding the population another 100 to 120 fold (1,200,000 laying hens). The million or more laying hens produce 600,000,000 eggs that are collected, cooled, cleaned, candled, graded, and packed.

Current production methods begin with collecting and cleaning fertile eggs from breeding farms. Commercial hens begin laying eggs at about 16 to 20 weeks of age, declining rapidly after 25 weeks. While there are various organic and free-range methods, the vast majority of eggs for consumption are obtained from battery cages. More recently, furnished cages (also known as enriched or modified cages) have been developed to improve the welfare of the egg laying hens.

For broilers, production includes maintenance of pedigree stocks for breeding that are pure lines. The eggs are hatched in special pedigree hatcheries and the progeny are used to generate great-grandparent (GGP) and grandparent generations (GP). The GP generation is then supplied to special GP hatcheries to parent stock (PS). The pure, inbred PS lines are then bred in broiler breeder farms from separate male and female lines to produce hybrid offspring. The hybrid offspring are then used for the production of broilers.

Hatcheries receive eggs from egg farms. Certain methods include inoculation of the eggs with antibiotics (typically gentamycin), though an increasing number of producers have production streams that preclude antibiotic use (e.g., products destined to be labeled "no antibiotic"). Increasingly, governments are adopting laws that preclude the routine use of antibiotics in agriculture. Currently, eggs destined for "organic production" can include eggs inoculated with antibiotics.

Whether producing hens for egg laying or broilers for meat production, the fertilized eggs are cleaned and checked for soundness before being placed in incubators. A number of companies manufacture commercial incubators for the large scale production of chicks, including for example, the Jamesway Incubator Company, Inc. (Ontario, Canada), Chickmaster International (Cresskill, NJ), Natureform Hatcher Technologies (Jacksonville, FL) and Surehatch (Cape Town, South Africa). Incubators can be manufactured to incorporate a PHPG generating system or can be modified to retrofit a PHPG generating system as illustrated in Example 12 below. The incubation periods and conditions vary depending on the species and these conditions are well known in the art.

The hatchery typically includes a receiving room to maintain and collect the eggs prior to incubation (on site egg room, receiving room, egg holding-room). The collection and storage at reduced temperatures arrests embryonic development and permits the accumulation of large numbers of eggs for a synchronized hatch. Typically, eggs are stored at 15° C. to 21° C., more usually between 18° C. and 20° C., for between about 24 and 72 hours. See Bourassa et al., "Elevated Egg Holding-Room Temperature of 74° F. (23° C.) does not Depress Hatchability or Chick Quality," Poultry Science Association, Inc. (2003). Importantly, eggs are stored below the temperature that will arrest further embryonic development known as "physiological zero" and commonly accepted for chickens as between about 18° C. and 20° C.). Eggs are preferably collected every 30 minutes and transferred to the on-site egg room. During collection and on site storage, eggs are added to the room periodically, typically every couple hours. Eggs are moved from receiving rooms to a first incubator, called a setter, that incubates the eggs at about 37° C., and provides for movement of the eggs to ensure proper development.

The incubation period for chickens is 21 days. For chickens, eggs are incubated in setter for about 18 days. Following incubation in the setter incubator, the eggs are moved to a hatching incubator where the final incubation period is completed, about 3 to 4 days. Though the incubation and hatching process can be performed in a single incubator, often the incubation and hatching are separated to minimize contamination and decrease costs. Typically, eggs are first incubated in a "setter" for 18 days. After 18 days, the incubated eggs are moved to a hatching incubator where the final three days of incubation are completed or until the hatching process is complete. The chicks are then ready for sorting and shipping to a grow-out farm for broilers or to an egg laying farm as appropriate. As would be understood to one of skill in the art, the increased temperatures and moisture provide a favorable environment for the growth of bacteria. Accordingly, there is a need for methods to reduce the levels of bacteria in both the setter incubator and the hatching incubator (or the combined incubator).

Hatchability is determined by a complex set of factors including storage time, age of the breeders (e.g., laying hens), as well as the incubation conditions. Among the important incubation conditions are the humidity (between 40% and 60% is preferred), temperature (optimal between 37 and 38° C.), turning conditions (eggs need to be turned during setting incubation period), and the gaseous environment (oxygen and carbon dioxide levels). Typically, an optimal breeder farm and hatchery produces about 85 healthy chicks from each 100 eggs set. Yields can commonly be 81% to 82% and can be as low as 70% to 75%. Given the large numbers involved (11 billion eggs set per year), even a small change in hatchability is significant.

After hatching, the chicks are sorted into first-quality chicks ("QI chicks") and second-quality chicks' ("Q2 chicks"). First-quality chicks are boxed and shipped to grow-out farms (broiler farms) where they are raised for meat. Significant losses occur through the hatching stage including dead chicks, second quality chicks, pipped eggs, infertile eggs. Methods of distinguishing QI and Q2 chicks are known in the art. See van de Ven et al., "Significance of chick quality score in broiler production," Animal 6(10): 1677-1683 (2012); Tona et al., "Effects of egg storage time on spread of hatch, chick quality and chick juvenile growth," Poult. Sci. 82(5):736-41 (2003); and Decuypere and Bruggeman, "The endocrine interface of environmental and egg factors affecting chick quality," Poult. Sci 86(5):1037-42 (2007).

Broiler farms receive chicks from the hatcheries and raise the chicks for meat in "grow-out houses" that are carefully controlled for temperature and humidity. There are about 70,000 grow-out houses located at about 17,000 farms. A typical grow-out house is about 12 to 15 meters wide by 120 to 180 meters long with 2.5 meter high walls. The average area of a grow-out house in the U.S. is about 1600 meters$^2$ (m$^2$), though more recent structures are about 1850 m$^2$. An average grow-out house produces approximately 113,000 birds and 600,000 pounds of meat per year. Like the setting and hatching incubators, the conditions of the grow-out house are critical to the health of the growing birds. Using modern methods, a 2.25 kg bird is produced in about 6 to 7 weeks. Once the growing cycle is complete, the birds are collected for shipment to a processing plant. Processing plants slaughter the broilers, bleed, de-feather and clean the carcass for shipping. Processing can further include chilling and cutting the meat to produce chicken parts.

Further losses occur during the feeding operations which take about 6 weeks from placing to market. Mortality peaks within 3 to 4 days of placement and then declines to a relatively steady level at days 9 or 10. At about day 30, mortality rates begin to rise and peak from between days 40 and 45 until harvest. It has been observed that flocks having high mortality levels in the first week tend to have higher mortality levels at weeks 7 and 8. Thus, methods and conditions that lead to reduced initial mortality are likely to reduce late mortality as well. See Tabler et al., "Mortality Patterns Associated with Commercial Broiler Production," Avian Advice, 6(1):1-3 (2004).

The causes of poultry mortality and morbidity are varied. Modern commercial poultry production methods often include intensive breeding, hatching, shipping, housing, and processing steps that favor the spread of bacterial, mycobacterial, fungal, parasitic, and viral diseases. In addition to mortality and morbidity, insects also contribute to decreased production.

Modern poultry production methods increase the susceptibility to diseases, including bacterial, viral, and parasitic diseases, due to the intensive nature of the methods. Chickens and other poultry are raised in close proximity to each other and have ample opportunity for direct transmission of diseases. The immune system of birds is different from mammals and may be a contributing factor. For example, it is known that the chicken immune system does not fully develop until well after hatching. In contrast to mammals, birds have hollow bones and thus do not have marrow for producing immune cells. Rather, immune cells are produced in a specialized organ, the bursa. In chickens, the bursa does not fully develop until the chick is about six weeks old, leaving newly hatched chicks particularly vulnerable to infection.

While free range and alternative methods exist, the vast majority of broilers are floor raised indoors on litter such as wood shavings, peanut shells, and rice hulls in buildings called grow-out houses. The housing is climate controlled and provides for feed and water, controlled temperature and moisture, and protects the chicks from predators. Chicks typically reach slaughter weight at about 5 to 9 weeks of age and average about 9 pounds. A typical grow-out house consists of about 20,000 birds.

Given the large number of birds, the presence of the litter, and of course the droppings, the grow-out house faces a number of health challenges. In addition to various insects, parasites, bacteria, and viruses, the droppings and litter produce large amounts of ammonia that are damaging to the chicken's respiratory systems and eyes and can result in hock burns to the legs. Accordingly, grow-out houses are supplied with large amounts of fresh air to remove the ammonia. Improved methods of control in grow-out houses are desirable, including methods that reduce the numbers of insects, parasites, bacteria, and viruses.

The impact of poultry diseases extends beyond the effects on the efficiency and cost of production of poultry products, which are significant. Bacterial diseases by bacteria that are naturally carried by poultry exert an enormous health cost on people. Accordingly, food safety is a priority concern for the poultry industry.

*Salmonella, Campylobacter, Listeria, Escherichia coli* and *Enterococcus* are significant causes of disease. The USDA reports that, in 2015, foodborne pathogens resulted in over $10 billion/year in medical costs. As shown in Table 1, *Salmonella* alone results in $3.7 billion in medical costs. The importance of these bacteria and their link to poultry has generated significant attention to mitigation methods.

contamination which contributes to human infection and mortality. As noted above, *Salmonella* as a foodborne illness is costing $3.7 billion/year. Chickens are well known carriers and sources of *Salmonella* infection and the disease is endemic. Indeed, no method has been identified to eliminate *Salmonella* from chicken production, in part because *Salmonella* naturally contaminates healthy chickens. See Humphrey et al., "Numbers of *Salmonella enteritidis* in the contents of naturally contaminated hens' eggs," *Epidemiol. Infect.* 106(3):489-496 (1991). In addition, *Salmonella* is known to be capable of penetrating egg shells and becoming inaccessible to control methods. See Cox et al., "*Salmonella* penetration of egg shells and proliferation in broiler hatching eggs—a review," *Poult. Sci* 79(11):1571-4 (2000). Cox et al. report that entry of salmonellae can occur through vertical transmission (transmission from an infected hen) and by horizontal transmission after the egg is laid. Current methods rely on injection of antibiotics (usually gentamycin) to reduce bacteria in eggs, but this approach is increasingly disfavored due to linkage to growing antibiotic resistance in bacteria

TABLE 1

Foodborne Illness Medical Costs (2015)

| Disease | Cost | Total | Hospitalizatio | Deaths |
|---|---|---|---|---|
| *Salmonella* | $3.7 billion | 1,027,561 | 19.336 | 378 |
| *Toxoplasma gondii* | $3.3 billion | 86.686 | 4,428 | 343 |
| *Listeria monocytogenes* | $2.8 billion | 1.591 | 1.173 | 306 |
| Norovirus | $2.3 billion | 5,461,731 | 14,663 | 149 |
| *Camvvlobacter* | $1.9 billion | 845,024 | 8,463 | 76 |
| *Clostridium perfringens* | $343 million | 965,958 | 438 | 26 |
| *Vibrio vulnificus* | $320 million | 96 | 93 | 36 |
| *Yersinia enterocolitica* | $278 million | 97,656 | 480 | 29 |
| *E. coli* 0157 | $271 million | 63,153 | 2,138 | 30 |
| *Vibrio* (non-cholera species) | $142 million | 17,564 | 83 | |

See Cost Estimates of Foodborne Illnesses available on the Web at ers.usda.gov/data-products/cost-estimates-of-foodborne-illnesses/

Given the impact of disease on production and human health, the poultry industry and individual operators develop and implement biosecurity plans to prevent the spread of poultry diseases. Biosecurity focuses on preventing the introduction of diseases to a facility and preventing transmission within a facility. Among the priorities are the separation of "clean" and "dirty" areas, provision and use of personal protection equipment (PPE), vector control (insects, worms, rodents, wild birds, pets), equipment control, mortality management, materials management (manure, litter), and feed and material intake control.

Current methods for controlling bacteria attack the problem at different stages of the production process. At the breeder farm or at the hatcher, various methods have been developed to reduce shell surface contamination. At each stage of the production process (Primary Breeder, Breeder Farm, Hatchery, Egg Production), there is an "egg preparation" step that typically involves collecting the eggs soon after laying, washing (dry or wet), fumigation or disinfection, and antibiotic injection to reduce contamination. At the hatchery, combatting bacterial infections have historically relied on antibiotics, though this strategy has increasingly come under scrutiny as it has been theorized the extensive use of antibiotics in agricultural production has contributed to the spread of antibiotic resistance. There exists a need to reduce and eliminate antibiotic use, preferably using organic, non-toxic methods.

The reduction of shell surface contamination has received considerable attention, particularly with regard to bacterial Among the methods in use for the reduction of shell surface contamination include fumigation, spray sanitizing methods, UV light irradiation, and egg washing. Fumigation with formaldehyde has been used but has been on the decline due to its potential human toxicity. Several commercial products are available for hatching egg sanitation. See Spray Sanitizing Hatching Eggs from the North Carolina Cooperative Extension Service available on the Web at www.ces.ncsu.edu/depts/poulsci/tech_manuals/spray_sanitizing.html; and Ernst, "Hatching Egg Sanitation: The Key Step in Successful Storage and Production," ANR Publication 8120 (2004) available on the Web at anrcatalog.ucanr.edu/pdf/8120.pdf.

Among the methods for sanitizing eggs as well as equipment, hydrogen peroxide ($H_2O_2$) has shown some promise when eggs are dipped or sprayed with solutions of between 1% and 5%. As a well-known sterilizing agent, hydrogen peroxide has been used to address a number of significant problems in poultry production. Typically, the application of hydrogen peroxide is through the direct application of a solution of hydrogen peroxide (with or without stabilizing agents) by either spraying or dipping. Hydrogen peroxide solutions of 1% or greater are used either alone or in combination with other treatments (e.g., heat or ultraviolet light).

Sheldon and Brake reports that 5% (vol/vol) of $H_2O_2$ is required to disinfect shell surfaces. They further report that a first treatment with 2% and a second treatment with 5%

$H_2O_2$ can improve hatchability. See Sheldon and Brake, "Hydrogen peroxide as an alternative hatching egg disinfectant," *Poult. Sci.* 70(5):1092-8 (1991). Padron reported that dipping eggs in 6% $H_2O_2$ solution twice reduced the number of *Salmonella* in eggshell membranes by 95% and reduced the numbers of positive eggs by 55% with no adverse effect on hatchability. See Padron, "Egg dipping in hydrogen peroxide solution to eliminate *Salmonella typhimurium* from eggshell membranes," *Avian Dis.* 39(3):627-30 (1995). Bailey et al., report that treatment of broiler eggs with hydrogen peroxide (2.5% fogged) did not significantly reduce, or improve, hatchability. Bailey et al., "Effect of Hatching Cabinet Sanitation Treatments on *Salmonella* Cross-Contamination and Hatchability of Broiler Eggs," *Poult Sci.* 75(2):191-6 (1996). Sander et al., "Effect of hydrogen peroxide disinfection during incubation of chicken eggs on microbial levels and productivity," *Avian Dis.* 43(2):227-33 (1999). Cox et al. reported that "hatchability and livability were unaffected by the most effective of the tested treatments." Cox et al. "Bactericidal Treatment of Hatching Eggs IV. Hydrogen Peroxide Applied with Vacuum and a Surfactant to Eliminate *Salmonella* from Hatching Eggs," *J Appl. Poult. Res.* 9:530-534 (2000). Cox et al. further report that multiple immersions of hatching eggs further decreased *Salmonella* with no adverse effect on hatchability. Notably, no improvement to hatchability was reported. Cox et al. studied the use of $H_2O_2$ (1.4% solution) applied with a vacuum and a surfactant to reduce *Salmonella* and reported that after treatment, 30% of the treated eggs remained contaminated. Cox et al., "Bactericidal Treatment of Hatching Eggs V: Efficiency of Repetitive Immersions in Hydrogen Peroxide or Phenol to Eliminate *Salmonella* from Hatching Eggs,"*J Appl. Poult. Res.* 11(3):328-331 (2002). Wells et al. report the combined disinfection of eggshells using ultraviolet light and hydrogen peroxide (3% solution) to achieve up to a 3 log reduction in bacterial counts (cfu/egg). No effects on hatchability or mortality were provided. See Wells et al., "Disinfection of eggshells using ultraviolet light and hydrogen peroxide independently and in combination," *Poult Sci.* 89(11):2499-505 (2010). While decreasing bacterial levels, at least temporarily, has not had an adverse effect on hatchability and mortality, neither has $H_2O_2$ treatment led to an improvement. None of the studies suggest that lower levels of $H_2O_2$ would be effective.

The application and use of $H_2O_2$ solutions to poultry production is not without problems however. First, vapor peroxide is highly corrosive and damages the incubator and other equipment in the area, even after a single use. The hatcheries don't like using it for that reason. Second, the aqueous and vapor peroxide treatments simply shock the bacteria on the eggs, reducing the log count, but not fully eliminating the bacteria; thus, once the eggs are placed in incubation (e.g., optimal growth conditions) the bacteria can quickly regrow to pre-treatment levels. Third, vapor or liquid hydrogen peroxide may harm the integrity of the eggshells, which are calcium carbonate, making them more permeable to bacteria that regrow on the eggs after treatment. Thus, the regrown bacteria may potentially have more impact through compromised eggshells. Fourth, a single droplet of vaporized or nebulized hydrogen peroxide can have $10^8$ to $10^9$ molecules of $H_2O_2$ per cubic micron. Such levels are toxic and cannot be used in occupied areas. For at least these reasons, eggs destined for hatching are not treated with hydrogen peroxide solutions.

There are a number of alternatives to hydrogen peroxide available. Mueller-Doblies et al., report that "disinfectants containing a mixture of formaldehyde, glutaraldehyde and QAC perform significantly better under field conditions than oxidizing products and should therefore be the first choice for disinfection of turkey premises where *Salmonella* is present." Mueller-Doblies et al. "A comparison of the efficacy of different disinfection methods in eliminating *Salmonella* contamination from turkey houses," *J Appl. Microbiol.* 109(2):471-479 (2010) ("[D] is infectants containing a mixture of formaldehyde, glutaraldehyde and QAC perform significantly better under field conditions than oxidizing products and should therefore be the first choice for disinfection of turkey premises where *Salmonella* is present"). Another approach is the application of chlorine dioxide either alone or with heat. This approach, like the use of aerosolized $H_2O_2$, formaldehyde, and glutaraldehyde is toxic and cannot be used in occupied areas. See, Kim et al., "Inactivation of *Salmonella* on Eggshells by Chlorine Dioxide Gas," *Korean J Food Sci. Anim. Resour.* 36(1):100-108 (2016); Park et al., "Inactivation of *Salmonella enterica* in chicken feces on the surface of eggshells by simultaneous treatments with gaseous chlorine dioxide and mild wet heat," *Food Microbial.* 62:202-206 (2017); and Choi et al., "Reduction of *Salmonella enterica* on the surface of eggshells by sequential treatment with aqueous chlorine dioxide and drying," *Int. J Food Microbial.* 210:84-87 (2015).

In addition, it has been shown that $H_2O_2$ treatments can have negative effects. Nebulized (e.g., vaporized) hydrogen peroxide is known to increase the susceptibility of chickens to avian pathogenic *Escherichia coli* (APEC), a cause of colibacillosis in chickens at all ages. Nebulized hydrogen peroxide is a mist comprising droplets of hydrogen peroxide at the indicated concentration and commercial nebulizers can prepare droplets of about 1 to 5 micrometers (µm) in diameter. See European Patent Publication No. EP 2 644 282. As provided by Oosterik et al., the "worsening effect [of increased bacterial lesions] after nebulization is probably due to the caustic effect of $H_2O_2$ radicals on (ciliated) epithelial cells . . . " Oosterik et al., "Disinfection by hydrogen peroxide nebulization increases susceptibility to avian pathogenic *Escherichia coli,"BMC Res. Notes.* 8:378 (2015). A droplet of vaporized $H_2O_2$ contains 100,000,000 to 1,000,000,000 molecules of $H_2O_2$ compared to the 5 to 25 molecules of DHP per cubic micron of air. Thus, the literature teaches the cautious application of hydrogen peroxide when applied to living cells as it can have significant negative consequences.

In addition to being a well-known sterilant, hydrogen peroxide is also known to be involved in cellular homeostasis and part of an inductive signaling process. For example, Patterson et al. report that hydrogen peroxide-regulated homeostasis involves the tyrosine-protein kinase lyn and the tyrosine-protein kinase syk. Both lyn and syk are known to be involved in signaling in mouse and chicken cells and in particular hematopoietic and nonhematopoietic cells and are proto-oncogenes. Hydrogen peroxide is also known to induce programmed cell death (apoptosis) in many cell types and organisms. See Wan et al, "Differential Gene Expression Patterns in Chicken Cardiomyocytes during Hydrogen Peroxide-Induced Apoptosis," *PLoS One* 11(1): e0147950 (2016). Hydrogen peroxide is also known to play an important role in angiogenesis. At low concentrations, $H_2O_2$ stimulates proliferation and migration and inhibits at higher concentrations. At higher concentrations, $H_2O_2$ induces new vessel formation; while at even higher concentrations, it induces apoptosis. See Mu et al., "Biphasic regulation of $H_2O_2$ on angiogenesis implicated NADPH oxidase," *Cell Biol. Int.* 34(10):1013-1020 (2010). In addition to effects on cells, hydrogen peroxide is also known to affect the porosity of eggshell membranes. See Hsieh et al., "Hydrogen peroxide treatment of eggshell membrane to control porosity," *Food Chem.* 141(3):2117-2121 (2013). Thus, the application of DHP gas to poultry and more particularly to eggs during development could result in significant, and unpredictable, changes in poultry development and health.

Another important use of eggs, primarily chicken, is for the production of vaccines, typically influenza. Vaccine producers receive eggs from specialized egg farms and incubate the eggs for a short period. Given the sensitive nature of vaccine production, even a single poultry pathogen can cause the ruination of an entire batch of vaccine eggs, causing upwards of a million dollars and six weeks in loss. The delay in vaccine production in turn can result in deaths due to delays in flu vaccination.

For vaccine production in particular, there is a need for reduced levels of contamination. Vaccine production facilities typically receive eggs from smaller farms with lower contamination levels. These eggs are incubated in the same types of incubators used in hatcheries, but on a smaller scale. Each small batch of eggs (tens of thousands) is worth millions of dollars and one contaminated egg can ruin an entire batch. Thus, there is a need to further reduce pathogen contamination of eggs for vaccine production.

In view of these significant losses, even small increases in incubation to placement efficiency can result in significant savings and increased profitability for hatcheries.

Aqueous hydrogen peroxide ($H_2O_2$) is a strong oxidant and has well known antimicrobial and antiseptic properties, as well as activity against organic compounds. $H_2O_2$ also has activity against volatile organic compounds (VOCs) oxidizing them and hydrolyzing them and breaking them down. Hydrogen peroxide hydrolyzes, among other things, formaldehyde, carbon disulfide, carbohydrates, organophosphorus and nitrogen compounds, and many other more complex organic molecules. $H_2O_2$ is produced commercially in large quantities as either a colorless liquid or as an aqueous solution, generally from about 3% to 90%. See Merck Index, 101 Edition at 4705 to 4707. It has recently been shown that $H_2O_2$ can be produced as a purified hydrogen peroxide gas (PHPG) that is free of ozone, plasma species, or organic species.

PHPG is a non-hydrated gaseous form of $H_2O_2$ that is distinct from liquid forms of hydrogen peroxide, including hydrated aerosols and vaporized forms. PHPG is generated in situ from ambient water vapor and cannot be produced from a solution of hydrogen peroxide. Aerosolized and vaporized forms of hydrogen peroxide solution have significantly higher concentrations of $H_2O_2$, typically comprising greater than $1 \times 10^6$ molecules per cubic micron compared to air containing PHPG that contains between 5 and 25 molecules per cubic micron. Hydrogen peroxide aerosols and vapors are prepared from aqueous solutions of hydrogen peroxide and also differ from PHPG as the aerosols are hydrated and, regardless of the size of the droplet, settle under the force of gravity. Vaporized forms condense and settle. Aerosolized forms of hydrogen peroxide are effective antimicrobial agents; however, they are generally considered toxic and wholly unsuitable for use in occupied spaces. See for example, Kahnert et al., "Decontamination with vaporized hydrogen peroxide is effective against *Mycobacterium tuberculosis*," *Lett. Appl. Microbiol.* 40(6):448-52 (2005). The application of vaporized hydrogen peroxide has been limited by concerns of explosive vapors, hazardous reactions, corrosivity, and worker safety. See Agalloco et al., "Overcoming Limitations of Vaporized Hydrogen Peroxide," *Pharmaceutical Technology*, 37(9):1-7 (2013). Further, spaces treated with aerosolized forms, typically at concentrations of between 150 and 700 ppm, remain unsuitable for occupation until the $H_2O_2$ has been reduced by degradation to water and oxygen and the $H_2O_2$. The use of PHPG solves the problem of toxicity of aerosolized $H_2O_2$ (e.g., vaporized and liquid forms of $H_2O_2$) and can provide continuous safe antimicrobial and oxidative activity.

PHPG is non-hydrated and behaves essentially as an ideal gas. In this form, PHPG behaves largely as an ideal gas and is capable of diffusing freely throughout an environment to attain an average concentration of about 25 molecules per cubic micron of air. As a gas, PHPG is capable of penetrating most porous materials, essentially diffusing freely to occupy any space that is not airtight. The gaseous form of hydrogen peroxide doesn't settle, deposit, or condense when present at concentrations at least up to 10 ppm. PHPG is completely "green" and leaves no residue as it breaks down the water and oxygen. PHPG cannot be prepared from an aqueous solution even if the vaporized form is a so-called "dried" form.

Importantly, and in contrast to vaporized and aerosolized forms of $H_2O_2$, environments containing up to 1 ppm $H_2O_2$ have been designated as safe for continuous human occupation under current Occupational Safety and Health Administration (OSHA), National Institute for Occupational Safety and Health (NIOSH), or American Conference of industrial Hygienists (ACGIH) standards. It is believed that 10 ppm is also safe for human occupation, though not yet recognized by the regulatory authorities. It is further anticipated that up to 50 ppm of PHPG is safe, but that level has not been tested. With the advent of PHPG generating devices, appropriate studies can now be performed. The ability to produce effective amounts of PHPG and the safety of PHPG when present as a dry hydrogen peroxide (DHP) gas combined with its effectiveness as an antimicrobial agent, suggests a myriad of potentially useful applications remain to be discovered.

U.S. Pat. No. 8,168,122 issued May 1, 2012, and U.S. Pat. No. 8,685,329 issued Apr. 1, 2014, both to Lee, disclose methods and devices to prepare PHPG for microbial control and/or disinfection/remediation of an environment (e.g., solid surfaces). International Patent Application No. PCT/US2014/038652, published as International Patent Publication No. WO 2014/186805, discloses the effectiveness and use of PHPG for the control of arthropods, including insects and arachnids. International Patent Application No. PCT/US2014/051914, published Feb. 26, 2015, as International Patent Publication No. WO2015/026958, discloses the beneficial effects of PHPG on respiratory health, including increased resistance to infection and increased hypothiocyanate ions in mammalian lungs. International Patent Application No. PCT/US2015/029276, published Nov. 12, 2015, as International Patent Publication No. WO 2015/171633, discloses improved PHPG generating devices. International Patent Application No. PCT/US2016/028457, published Oct. 27, 2016, as International Patent Publication No. WO 2016/172223, discloses an application of DHP to clean rooms. International Patent Application No. PCT/US2016/029847, published Nov. 3, 2016, as International Patent Publication No. WO 2016/176486, discloses methods of use of DHP in agricultural production, transport, and storage. The contents of each of the foregoing applications are incorporated herein by reference in their entireties.

While not limited, the present specification provides for the first time the effects of PHPG/DHP treatment on eggs and poultry. In previous studies, PHPG/DHP was demonstrated to be effective on solid surfaces. In other studies DHP was shown to be beneficial and therapeutic to people and yet toxic to arthropods; thus, it was unclear how DHP would affect egg and chick development.

It is provided here that porous, gas permeable egg shells can be effectively treated with DHP and embryos undergo normal development. It is further provided that eggs can be safely and effectively treated at laying and safely transferred to climate controlled on site egg rooms. The present application provides that the continuous treatment of eggs through the setting and hatching stages is safe and results in improvements to chick health. Notable improvements include, but are not limited to, increased hatchability, decreased post hatching mortality, improved food conversion ratio, reduced cull rates, and increased weight at hatching. Prior to the present disclosure, it was unclear whether DHP would be effective against microbes on the surface and presumably within pores. More importantly, prior to the present disclosure, the safety of DHP on the developing embryos was uncertain. Here we show that DHP is not only safe for extended application to poultry eggs but also significantly improves the quality of the egg including, for example, reducing bacterial loads, reducing the number of rotten eggs, decreasing 1 week mortality, and decreasing overall mortality. In addition, application of DHP during the laying, storing, incubating, and hatching stages decreases deformities and increases hatch rates.

As disclosed, the poultry production process consists of numerous steps that provide for exposure of the poultry to pathogens. Not to be limited by theory or example, DPH treatment provides for reduced contamination at egg laying, reduced bacterial loads and growth during on-site storage, prevention of contamination of compromised eggs (e.g., eggs with microcracks), reduced seven day mortality, decreased cull rates, reduced rates of condemnation, and reduced on-farm mortality. The safety and efficacy of hydrogen peroxide gas allows for each step in the process to be targeted separately and as part of an overall mitigation strategy to reduce viral and bacterial pathogens, to reduce parasitic pathogens, and to reduce the various insect vectors that transmit pathogens.

SUMMARY OF THE INVENTION

The present specification provides for, and includes, a method for improving poultry eggs comprising placing poultry eggs into a poultry space, providing dry hydrogen peroxide (DHP) at a concentration of between 0.001 parts per million (ppm) and 10 ppm to the poultry space, and maintaining the poultry eggs in the poultry space for a storage period. The present specification provides for, and includes, a method for improving poultry eggs comprising placing poultry eggs into a poultry space, providing dry hydrogen peroxide (DHP) at a concentration of 10 ppm or less to the poultry space, and maintaining the poultry eggs in the poultry space for a storage period.

In an aspect, the present specification provides for a poultry space comprising dry hydrogen peroxide gas (DHPG) at a concentration of between 0.001 ppm and 10 ppm.

In a further aspect, the present specification provides for a method of killing coccidial oocysts of the phylum Apicomplexa in litter comprising treating the litter with dry hydrogen peroxide gas (DHPG) at a concentration of at least 0.001 ppm.

In a further aspect, the present specification provides for a method of reducing damage to poultry production facilities from insect infestation comprising providing a poultry production facility with dry hydrogen peroxide gas (DHPG) at a concentration of at least 0.001 ppm. In a further aspect, the present specification provides for a method of reducing damage to poultry production facilities from insect infestation comprising providing a poultry production facility with dry hydrogen peroxide gas (DHPG) at a concentration of less than 10.0 ppm. In a further aspect, the present specification provides for a method for reducing disease in a poultry production flock comprising providing a poultry production facility with dry hydrogen peroxide gas (DHPG) at a concentration of at least 0.01 ppm to the flock. In a further aspect, the present specification provides for a method for reducing disease in a poultry production flock comprising providing a poultry production facility with dry hydrogen peroxide gas (DHPG) at a concentration of less than 10.0 ppm.

In a further aspect, the present specification provides for a method for reducing odors emanating from a poultry production facility comprising providing a poultry production facility with dry hydrogen peroxide gas (DHPG) at a concentration of at least 0.01 ppm. In a further aspect, the present specification provides for a method for reducing odors emanating from a poultry production facility comprising providing a poultry production facility with dry hydrogen peroxide gas (DHPG) at a concentration of less than 10.0 ppm.

In a further aspect, the present specification provides for a method for preventing the spread of a communicable disease in a poultry facility comprising identifying a poultry production facility having an introduced communicable disease and providing the poultry production facility with a PHPG generating device and generating dry hydrogen peroxide (DHP) gas at a concentration of at least 0.01 ppm. In a further aspect, the present specification provides for a method for preventing the spread of a communicable disease in a poultry facility comprising identifying a poultry production facility having an introduced communicable disease and providing the poultry production facility with a PHPG generating device and generating dry hydrogen peroxide (DHP) gas at a concentration of less than 10.0 ppm.

In a further aspect, the present specification provides for a kit comprising one or more portable DHP generating devices for use in a rapid response to an infectious disease outbreak on a poultry farm.

In a further aspect, the present specification provides for a method for treating an emergent disease at a poultry facility comprising providing the poultry facility with an excess of PHPG generating devices and generating dry hydrogen peroxide (DHP) gas at a concentration of at least 0.1 ppm.

In an aspect, the present specification provides for a method for reducing the risk of omphalitis comprising incubating poultry eggs in the presence of Dilute Hydrogen Peroxide (DHP) gas during pre-incubation storage or during hatching incubation.

In an aspect, the present specification provides for a method for decreasing the microbial load of a poultry egg comprising collecting eggs from a plurality of hens, transferring the eggs to an egg room having a temperature below physiological zero and having up to 10 parts-per-million DHP gas, storing the eggs prior to incubation, and removing the eggs after a time period for transfer to an incubator.

In a further aspect, the present specification provides for incubators for poultry eggs comprising an enclosure; a temperature control system; and an air circulation system including a 5DHP gas generating system.

In a further aspect, the present specification provides for a storage room for poultry eggs comprising a temperature below physiological zero and up to 5 parts-per-million (ppm) of DHP gas.

In an aspect, the present specification provides for Dilute Hydrogen Peroxide (DHP) gas treated eggs comprising poultry eggs treated with up to 10 ppm DHP gas at a temperature below physiological zero for a storage period prior to incubation.

In an aspect, the present specification provides for improved chicks hatched from DHP gas treated poultry eggs, wherein the DHP gas treated poultry eggs have been treated with up to 10 ppm DHP gas at a temperature below physiological zero for a storage period prior to incubation.

In an aspect, the present specification provides for improved chicks hatched from DHP gas treated poultry eggs, wherein the DHP gas treated poultry eggs have been treated with up to 10 ppm DHP gas at a temperature below physiological zero for a storage period prior to incubation and treated during incubation with up to with up to 10 ppm DHP gas.

BRIEF DESCRIPTION OF THE DRAWINGS

The present disclosure is disclosed with reference to the accompanying drawings wherein:

FIGS. 8A-D are diagrams of a non-limiting example of an air recirculation system for a setting or hatching incubator that provides DHP. FIG. 8A presents a cutaway view of a DHP air producing air recirculation system. FIG. 8B presents a side view of a DHP air producing air recirculation system. FIG. 8C presents a view of a DHP air producing air recirculation system from inside a setting or hatching incubator. FIG. 8D presents an external view of a DHP air producing air recirculation system.

DETAILED DESCRIPTION

Figure 1:
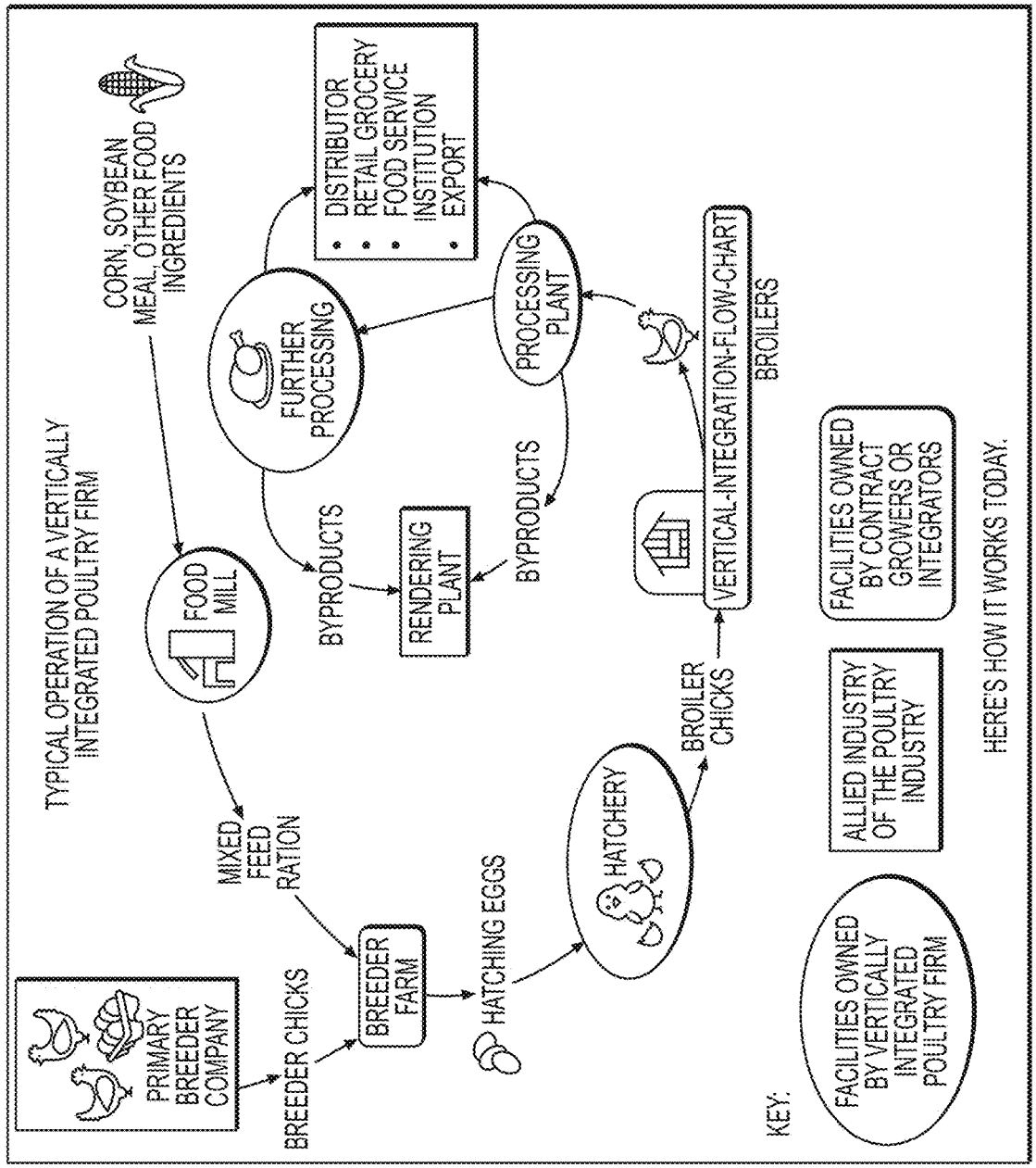
FIG. 1 is a diagram of the steps in the industrial production of poultry.

Unless defined otherwise, technical and scientific terms as used herein have the same meaning as commonly understood by one of ordinary skill in the art. One skilled in the art will recognize many methods can be used in the practice of the present disclosure. Indeed, the present disclosure is in no way limited to the methods and materials described. Any references cited herein are incorporated by reference in their entireties. For purposes of the present disclosure, the following terms are defined below.

The present specification provides for, and includes, a method for improving poultry eggs comprising placing poultry eggs into a poultry space, providing dry hydrogen peroxide (DHP) at a concentration of between 0.001 ppm and 10 ppm to the poultry space, and maintaining the poultry eggs in the poultry space for a time period. The present specification provides for and includes poultry spaces, for example as described below, that have significantly higher levels of DHP. In a certain aspect, the DHP gas level can be up to 10 ppm. In a certain aspect, the DHP level ranges between 0.05 ppm and 10 ppm. In an aspect, the concentration of DHP gas in a poultry space of the present specification is at least 0.08 ppm. In another aspect, the concentration of DHP gas is at least 1.0 ppm. In yet another aspect, the concentration of DHP gas is at least 1.5 ppm. In an aspect, the concentration of DHP gas in a poultry space of the present specification is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas in a poultry space of the present specification is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas in a poultry space of the present specification is between 1.0 ppm and 8.0 ppm, or between 5.0 ppm and 10.0 ppm. In another aspect, the concentration of DHP in a poultry space cycles between higher and lower concentrations of DHP. By way of non-limiting example, the DHP can be maintained at a higher concentration during the overnight hours and a lower concentration during the daytime hours.

As used herein, a DHP gas generating system comprises a source of ultraviolet light and an air-permeable substrate structure having a catalyst on its surface. In an aspect, a DHP gas generating system further comprises an air distribution mechanism for providing an airflow. In another aspect, an air distribution system for providing an airflow is provided separately, for example as part of an HVAC system or as part of an incubator. To generate DHP, the system is configured so the ultraviolet light source illuminates the air-permeable substrate structure and air-flows through the air-permeable substrate structure. DHP generating systems and methods for configuring such systems are known in the art, for example DHP generating devices are described in detail in U.S. Pat. No. 8,168,122 issued May 1, 2012, and International Patent Application No. PCT/US2015/029276, published Nov. 12, 2015, as International Patent Publication No. WO2015/171633.

As used herein, a storage period or time period for DHP gas treatment of a poultry space is at least one hour. In an aspect, DHP is provided throughout the production process including during the laying process (e.g., treating the hens and laying facility), during storage, during incubation (both setting and hatching), and during grow-out. In an aspect, the storage or time period for providing DHP is between 1 and 7 days. In an aspect, the eggs are treated for a storage period of between 1 and 7 days. In another aspect, the eggs are treated for storage period of at least 1 day. In another aspect, the eggs are treated for at least 2 days. In another aspect, the eggs are DHP gas treated during a storage period or time period for at least 3 days. In yet another aspect, the improved eggs are prepared by treating the eggs for at least 4 days. In an aspect, the eggs are exposed to at least 0.001 ppm of DHP gas at a temperature below physiological zero for at least one hour. In an aspect, the eggs are exposed to at least 0.001 ppm of DHP gas at an appropriate incubation temperature for at least one hour. In an aspect, the eggs are exposed to at least 0.001 ppm of DHP gas for at least two hours. In an aspect, the eggs are exposed to at least 0.001 ppm of DHP gas for at least four hours. In an aspect, the eggs are exposed to at least 0.001 ppm of DHP gas for at least eight hours. In an aspect, the eggs are exposed to at least 0.001 ppm of DHP gas at a temperature below physiological zero for at least 12 hours. In an aspect, DHP gas is provided to the eggs, hens, chicks at a concentration of between 0.001 ppm and 10 ppm for a period of at least an hour. In an aspect, DHP gas is provided to the eggs at a concentration of between 0.001 ppm and 10 ppm for a for at least and hour and throughout hatching. As a safe effective treatment, DHP gas may be provided continuously at all stages of the poultry production process.

Catalysts of the present disclosure include, but are not limited to, titanium dioxide, copper, copper oxide, zinc, zinc oxide, iron, iron oxide, or mixtures thereof. Suitable catalysts are provided, for example at Table 2. In some aspects, the catalyst is titanium dioxide in the form of anatase or rutile. In certain aspects, the titanium dioxide is the anatase form. In some aspects, the catalyst is titanium dioxide in the form of rutile. In other aspects, the titanium dioxide catalyst is a mixture of anatase and rutile.

TABLE 2

Catalysts for DHP prodUCflOU

| Photocatalyst | Band-gap energy (electron volts (eV)) |
|---|---|
| Si | 1.1 |
| $WSe_2$ | 1.2 |
| CdS | 2.4 |
| $WO_3$ | 2.4– |
| $V_2O_5$ | 2.7 |
| SiC | 3.0 |
| $TiO_2$ (rutile) | 3.02 |
| $Fe_2O_3$ | 3.1 |
| $TiO_2$ anatase | |
| ZnO | |
| $SRTiO_3$ | |
| $SnO_2$ | 3.5 |
| ZnS | 3.6 |

As provided herein, improving poultry eggs refers to reducing the load of a pathogen (bacterial, viral), increasing hatchability, reducing the number of pipped unhatched eggs, increasing chick quality, improving chick quality scores, reducing chick mortality, or reducing mortality in chicks hatched from the treated eggs and grown in the DHP containing spaces of the present specification. Not to be limited by theory, it is thought that as an ideal gas, DHP is not only able to reduce contamination of the shell surface, but is also able to pass through the shell and act on the interior shell surface and shell membrane.

In an aspect according to the present specification, the method provides for improving poultry eggs comprising a decrease in the number of pathogens on the egg. In an aspect, the pathogen is one or more of the bacteria discussed below, for example but not limited to, *Salmonella* spp., *Enterococcus* spp., *Staphylococcus* spp., *Escherichia* spp., *Streptococci* spp., *Clostridium* spp., or combinations thereof. In an aspect, the bacteria is a *Salmonella* spp. In an aspect, the bacteria is a *Enterococcus* spp. In an aspect, the bacteria is a *Staphylococcus* spp. In an aspect, the bacteria is a *Escherichia* spp. In an aspect, the bacteria is a *Streptococci* spp. In an aspect, the bacteria is a *Clostridium* spp.

In another aspect, the pathogen is one or more viruses as discussed below, for example but not limited to, members of the Orthomyxoviridae (influenza), Picornaviridae, Retroviridae, Herpesviridae, Hepeviridae, Poxviridae, Parvoviridae, Paramyxoviridae, or Reoviridae families. In an aspect, a virus is a member of the Orthomyxoviridae (influenza) family. In an aspect, a virus is a member of the Picornaviridae family. In an aspect, a virus is a member of the Retroviridae family. In an aspect, a virus is a member of the Herpesviridae family. In an aspect a virus is a member of the Hepeviridae family. In an aspect, a virus is a member of the Poxviridae family. In an aspect, a virus is a member of the Parvoviridae family. In an aspect, a virus is a member of the Paramyxoviridae family. In an aspect, a virus is a member of the Reoviridae family.

In an aspect, the pathogen is one or more of the fungi (or fungi spores) as discussed below, for example but not limited to, *Aspergillus* spp., *Candida* spp., *Fusarium* spp., or combinations thereof. In an aspect, the fungus is an *Aspergillus* spp. In an aspect, the fungus is a *Candida* spp. In an aspect, the fungus is a *Fusarium* spp. In another aspect, the pathogen is one or more of the mycobacteria of the genus *Mycoplasma*.

In an aspect according to the present specification, the method provides for improving poultry eggs comprising increasing hatchability. In an aspect, hatchability is increased 0.5% or more when the eggs are placed in a poultry space having DHP at a concentration of between 0.01 ppm and 10 ppm. In another aspect, hatchability is increased by 1.0% or more. In another aspect, hatchability is increased by 1.5% or more. In an aspect, hatchability is increased by 2.0% or more.

In an aspect according to the present specification, the method provides for improving poultry eggs comprising reducing the number of pipped unhatched eggs when the eggs are placed in a poultry space having DHP at a concentration of between 0.01 ppm and 10 ppm. As used herein, the percentage of eggs that are pipped unhatched eggs is the percentage of pipped unhatched eggs when compared to the total number of eggs placed in incubation. In an aspect, the percentage of pipped unhatched eggs is reduced by at least 0.5%. In another aspect, the percentage of pipped unhatched eggs is reduced by at least 1.0%. In yet other aspects, the percentage of pipped unhatched eggs is reduced by at least 1.5%. In further aspects the percentage of pipped unhatched eggs is reduced by at least 2.0%. In additional aspects, the percentage of pipped unhatched eggs is reduced by between 0.5% and 2%.

In an aspect according to the present specification, the method provides for improving poultry eggs comprising increasing chick quality. In an aspect, a chick hatched from a treated egg has increased quality when examined at one day old. In an aspect, the percentage of chicks that are First Quality (QI) is increased by at least 1%. The identification and determination of QI chicks is known in the art. See Tona et al., "Effects of egg storage time on spread of hatch, chick quality and chick juvenile growth," *Poult Sci.* 82(5): 736-41 (2003); Decuypere and Bruggeman, "The endocrine interface of environmental and egg factors affecting chick quality," *Poult. Sci* 86(5):1037-42 (2007); and van de Ven et al., "Significance of chick quality score in broiler production," *Animal* 6(10):1677-1683 (2012). A QI chick is a one day old chick that is clean, dry and free from dirt and contamination, has clear and bright eyes, and is free of deformities with a completely sealed and clean navel and no yolk sacs or dried membranes protruding from the navel area. A QI chick should be alert and interested in its environment, respond to sound, exhibit a normal conformation of legs, exhibit no hock, exhibit no swelling, exhibit no skin lesions, and it should have a well-formed beak and soft but straight toes.

In an aspect according to the present specification, a treated poultry egg has an improved Pasgar© score. Boerjan, "Programs for single stage incubation and chick quality," *Avian Poult. Biol. Rev.* 13:237-238 (2002). Using the Pasgar©, the quality of each chick is evaluated based on five criteria: (1) navel condition (black button or leaky navel); (2) yolk sac (large size of the residual yolk sac); (3) red hocks (red or swollen hocks); (4) abnormal beak (red beak or nostrils contaminated with albumen); and (5) low alertness. For each of the five criteria, one point is subtracted from 10, with chicks scoring 10 being free of any abnormality and 5 being the lowest score. Use of the Pasgar© score is well known in the art. Typically, at least 44 chicks from a hatching are assessed.

In another aspect according to the present specification, a poultry egg has an improved Tona score. See Tona et al., "Effects of Egg Storage Time on Spread of Hatch, Chick Quality, and Chick Juvenile Growth," *Poultry Science* 82:736-741 (2003). The Tona score evaluates eight different parameters to determine chick quality: 1. activity; 2. down and appearance; 3. retracted yolk; 4. eyes; 5. legs; 6. naval area; 7. remaining membrane; and 8. remaining yolk. These parameters are allocated to different scores according to their importance within a total score of 100. Typically, at least 44 chicks from a hatching are assessed.

TABLE 3

| Categories of Q2 Chicks (from van de Ven (2012)) | |
| --- | --- |
| Physical anomaly | Chicks showing physical anomalies, such as an open skull, crossed beak, four legs |
| Abnormal down | Wet, sticky or short white down |
| Leg deformation | Cripple chicks resulting from leg deformity, or from being trapped in an egg tray |
| Weak appearance | Small or unstable chicks |
| Low-quality score | Either multiple criteria were scored based on Pasgar ® score, indicating low chick quality without a clear single abnormality, or no obvious reason could be identified for classifying as second grade |
| Dead before examination | Chicks that emerged from the egg, but died before examination of the chicks took place |

In an aspect according to the present specification, the method provides for improving poultry eggs comprising providing 0.01 ppm DHP during setting incubation. In an aspect, the method provides for a setting incubation period in the presence of at least 0.01 ppm DHP for a least 1 week. In another aspect, the method provides for a setting incubation period in the presence of at least 0.01 ppm DHP for at least 2 weeks. In another aspect, the method provides for a setting incubation period in the presence of at least 0.01 ppm DHP for at least 16 days. In a certain aspect, the level of DHP provided during setting incubation is at least 1.0 ppm. In another aspect, the level of DHP provided during setting incubation is at least 1.5 ppm. In another aspect, the level of DHP provided during setting incubation is at least 2.0 ppm. In another aspect, the level of DHP provided during setting incubation is less than 10.0 ppm. In an aspect, the amount of DHP provided during setting incubation is less than 100 molecules $H_2O_2$ per cubic micron of air.

In an aspect according to the present specification, the method provides for improving poultry eggs comprising providing 0.01 ppm DHP during hatching incubation. In an aspect, the method provides for a setting incubation period in the presence of at least 0.01 ppm DHP during the entire hatching incubation period (up to 4 days). In another aspect, the method provides for a hatching in the presence of at least 0.01 ppm DHP for at least one day of the hatching period. In another aspect, the method provides for a hatching incubation period in the presence of at least 0.01 ppm DHP for at 2 days. In a certain aspect, the DHP gas level can be up to 50 ppm. In another aspect, the DHP gas level can be up to 10 ppm. In a certain aspect, the DHP level ranges between 0.01 and 10 ppm. In an aspect, the concentration of DHP gas during hatching incubation of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas during hatching incubation of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas during hatching incubation of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas during hatching incubation of the present disclosure is between 1.0 ppm and 8.0 ppm, or between 5.0 ppm and 10.0 ppm. In another aspect, the concentration of DHP during hatching incubation cycles between higher and lower concentrations of DHP. In an aspect, the amount of DHP provided during setting incubation is less than 100 molecules $H_2O_2$ per cubic micron of air.

Also included and provided for by the present specification is the treatment of newly hatched chicks with at least 0.01 ppm DHP for one or more days. In an aspect, treatment of newly hatch chicks with at least 0.01 ppm DHP leads to a reduction in post-hatching mortality. In a certain aspect, the DHP gas level can be up to 50 ppm. In another aspect, the DHP gas level can be up to 10 ppm. In a certain aspect, the DHP level ranges between 0.01 and 10 ppm. In an aspect, the concentration of DHP gas provided to newly hatched chicks of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas provided to newly hatched chicks of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to newly hatched chicks of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to newly hatched chicks of the present disclosure is between 1.0 ppm and 8.0 ppm, or between 5.0 ppm and 10.0 ppm. In another aspect, the concentration of DHP during hatching incubation cycles between higher and lower concentrations of DHP. In another aspect, treatment of newly hatched chicks results in a reduction of bacterial levels on the fur/feathers by at least 10 fold. In an aspect, the present specification provides for a reduction of bacteria on the beak of a chick by at least 10 fold.

The present specification provides for, and includes, methods for incubating eggs comprising obtaining eggs for hatching, placing the eggs into an incubator capable of producing dry hydrogen peroxide (DHP) gas at a concentration of between 0.001 parts per million (ppm) and 10 ppm, and incubating the eggs for between 1 and 18 days (e.g., setting incubation). In an aspect, the method further includes a second incubation period comprising between 1 to 5 days, or until hatching is complete, in the presence of DHP gas at a concentration of between 0.001 ppm and 10 ppm (e.g., hatching incubation). In an aspect, both the setting and hatching incubations are completed in a single incubator. In another aspect, the setting and hatching incubations are performed in separate incubators. The method may further include a pre-incubation treatment of the eggs comprising storing the eggs at a temperature below physiological zero in the presence of dilute hydrogen peroxide (DHP) gas at a concentration between 0.001 and 5 parts-per-million (ppm) of DHP gas for between 1 and 7 days prior to incubation. In an aspect, the DHP gas is provided at a concentration of at least 0.01 ppm during setting incubation, hatching incubation, storage or combinations thereof. In an aspect, the DHP gas is provided at a concentration of at least 0.05 ppm during setting incubation, hatching incubation, storage or combinations thereof. Suitable incubator comprising integrated DHP gas generating devices are described in detail below.

The methods for incubating eggs may further include preparation of the setting or hatching incubators comprising washing and cleaning the interiors of the incubators, for example to clean up after a prior incubation. In an aspect, the methods for incubating eggs includes changing the air-permeable substrate structure. In an aspect, the methods may further include pre-treating the incubator with DHP gas prior to loading the eggs for incubation. Thus, bacteria and pathogens in the interior of the incubator are reduced. In an aspect the incubator is pre-warmed and pre-treated with DHP gas prior loading the eggs for incubation. In an aspect, the method further includes monitoring DHP gas levels or the status of the air-permeable substrate structure and replacing the air-permeable substrate structure to ensure efficient production of DHP gas during the approximately month long production cycle.

The present specification provides for, and includes, a method for improving poultry comprising placing birds into a poultry space, providing dry hydrogen peroxide (DHP) at a concentration of between 0.01 ppm and 50 ppm to the poultry space, and maintaining the poultry eggs in the poultry space for a storage period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to a poultry space of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas provided to a poultry space of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to a poultry space of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to a poultry space of the present disclosure is between 1.0 ppm and 8.0 ppm, or between 5.0 ppm and 10.0 ppm. In another aspect, the concentration of DHP during hatching incubation cycles between higher and lower concentrations of DHP. In an aspect, the method provides for the reduction of poultry disease. Non-limiting examples of poultry diseases reduced by the treatment of eggs, chicks, or poultry spaces with dry hydrogen peroxide (DHP) at a concentration of between 0.01 ppm and 50 ppm are presented in Table 3. In an aspect, the improved poultry have a reduction in parasitic disease. In another aspect, the method provides for a reduction of transmission of an infectious poultry disease. In an aspect, the infectious poultry disease is a virus. In another aspect, the infectious poultry disease is a bacteria.

The present specification provides for, and includes, storage rooms for poultry eggs having a concentration of DHP gas of up to 5 ppm and a temperature that is maintained below physiological zero. In an aspect, the storage room has at least 0.001 ppm of DHP gas. In an aspect, the storage room of the present specification has a detectable level of DHP gas. Storage rooms according to the present specification have between 0.001 ppm DHP gas and 10 ppm DHP gas. As used herein, the term "physiological zero" refers to the temperature wherein embryonic development slows down and is essentially arrested. Physiological zero is the temperature that is low enough to maintain embryonic cell activity at a greatly reduced but reversible level. At physiological zero, development is arrested but can continue once the temperature increases again. The term physiological zero is known to hatchery managers and those of skill in the art to not be restricted to a specific temperature but a range of temperatures, typically between 12° C. and 21° C., depending on the context of the egg handling and storage length (see Boerjan, "A practical interpretation of 'physiological zero' in hatchery management," Pas Reform Incubation Guide 5.2 or 6.0 (Apr. 8, 2016)). Physiological zero further depends on the age of the flock where young flocks (25 to 30 weeks) are stored at 20° C., flocks from 35 to 50 weeks are stored at 21.1° C., and older flocks (>55 weeks) stored at about 24° C. (See, Henderson et al., "On-Farm Egg-Holding Temperatures for Commercial Broiler Breeders," Avidan Advice 8(1):3-6 (2006), More usually, physiological zero is thought to be between 20° C. and 21° C. (Proudfoot et al., "Care of Hatching Eggs Before Incubation," Agriculture Canada, Publication 1573/E (1990)). In some reports, physiological zero is reported as below 25° C. (Warin, S., "Embryonic Development," Ceva Animal Health Asia Pacific Newsletter, issue 7 (2006)). As is evident, the meaning of the term "physiological zero" is well known in the art. In an aspect, the physiological temperature is 24° C. or less. In another aspect the temperature of the storage room is maintained between 16° C. and 18° C. In some aspects, the temperature of the storage room is maintained above 10° C.

A storage room according to the present specification can further comprise a humidifier or dehumidifier to maintain a level of humidity known in the art to be required to maintain egg viability. In an aspect, the storage room is maintained at a humidity of between 60% and 90%. In an aspect, the storage room is maintained at a humidity of between 80% and 88%. In an aspect, the storage room is maintained at a humidity of between 75% and 80%. In another aspect, the storage room is maintained at a humidity of between 40% to 90%. In an aspect, the storage room is maintained at a humidity of between 75% to 82%. In yet another aspect, the storage room is maintained at a humidity of between 75% and 85%. In some aspects, the relative humidity of the storage room is between 80% and 85%, particularly when intended for storage of eggs for longer periods.

The present specification provides for, and includes, incubators for poultry eggs comprising an enclosure, a temperature control system, an air circulation system, and at least one DHP gas generating device. An incubator of the present specification can be a single-stage or multi-stage incubator and can be free standing or comprising a room. In an aspect, an incubator of the present specification can be designed and manufactured to include one or more DHP generating devices. In another aspect, an incubator can be a conventional incubator retrofitted with one or more DHP generating devices, for example as illustrated in FIG. 8 and Example 9. Incubators of the present specification are provided with a sufficient DHP generating capacity to maintain DHP gas at up to 5 ppm under varying conditions. In another aspect, the incubators are capable of maintaining DHP gas at a level between 0.01 ppm and 5 ppm. The amount of DHP gas needed to maintain levels varies with the conditions that include, but are not limited to, the number of eggs in the incubator, the outside temperature, the relative humidity, and the amount of air circulation required to maintain adequate levels of oxygen and levels of carbon dioxide not to exceed 0.09%. Preferably, sufficient air is circulated to maintain carbon dioxide levels below 0.04%. An incubator of the present specification can be free standing and comprise an enclosure or may be part of a fixed facility as a room. Typically, incubators of the present specification are free-standing single or multi-stage incubators. In an aspect, an incubator of the present disclosure is configured for the incubation of chicken eggs, turkey eggs, quail eggs, duck eggs, and goose eggs. In an aspect, an incubator of the present disclosure is configured for the incubation of chicken eggs. In an aspect, an incubator of the present disclosure is configured for the incubation of turkey eggs.

An incubator of the present disclosure may further include a temperature control system. The temperature control systems can include heating elements, cooling elements, or both, controlled by an environmental control unit. As provided herein, incubators can include heating and cooling elements, temperature sensors, and a communication device capable of sending and receiving data from a remote controller.

An incubator of the present disclosure can further include an air circulation system. The air circulation system provides for an even distribution of heat, for example, to optimize embryonic development. An air circulation system further includes providing oxygen to the developing embryos and removing carbon dioxide. In an aspect, the air circulation system includes a clean air plenum to introduce air during the incubation period. As the embryos develop, the requirements for oxygen and for the removal of carbon dioxide increase. Accordingly, the air circulation system can further include one or more sensors for oxygen, carbon dioxide, or both. In an aspect, the sensors are in communication with a local or remote environmental control unit to adjust the air flow and the intake of air through a clear air plenum to maintain optimal incubation parameters. In an aspect, the environment control system can increase or decrease the amount of DHP generated to maintain desired levels of DHP gas during the incubation period. In an aspect, the incubator includes additional DHP gas generating devices that can be used to supplement DHP gas levels as required, for example during hatching when biological activity and thus sinks (e.g., places or reactions where DHP is used up) of DHP gas are increased. As provided herein, the air circulation system can comprise one or more fans to circulate the air throughout the incubator. In an aspect, multiple fans are included to increase air flow while maintaining energy efficiency. In a certain aspect, the airflow of the air circulation system is a laminar flow air system. In an aspect, the fans are variable control fans controlled by the temperature control system (locally or remotely).

Incubators of the present disclosure include incubators having an egg turning system. In an aspect, incubators equipped with a DHP gas generating system can include either a fixed or removable egg turning system. In another aspect, the incubators of the present disclosure further include a humidity control system comprising a humidifier, dehumidifier, or both. In an aspect, control of the humidity by the environmental control unit provides optimal humidity for the production of DHP gas and for the development of the embryo. In an aspect, a humidity control system is capable of maintaining a relative humidity of up to 90%. In an aspect, the humidity control system is capable of maintaining a relative humidity of up to 80%. In another aspect, the humidity control system is capable of maintaining the relative humidity between 40 to 75%. In yet other aspects, the humidity control system is capable of maintaining the relative humidity between 50% and 65%.

The present specification provides for, and includes, a method for increasing the feed conversion ratio (FCR) in poultry production comprising placing birds into a poultry space, providing dry hydrogen peroxide (DHP) at a concentration of between 0.01 ppm and 50 ppm to the poultry space, and maintaining the poultry eggs in the poultry space for a period. The feed conversion ratio (FCR) or feed conversion rate is a measure of an animal's efficiency in converting feed mass into increases of the desired output. The broiler/feed ratio is the number of pounds of broiler grower feed equal in value to 1 pound of broiler, live weight. Egg/feed ratio is the number of pounds of laying feed equal in value to one dozen market eggs. Turkey/feed ratio is the number of pounds of turkey grower feed equal in value to 1 pound of turkey, live weight. As used herein, the FCR is calculated based on the mixed feed provided to the poultry during growth and is not inclusive of insects, worms and other foods ("non-feedmill foods") that poultry can encounter in a poultry space. Not to be limited by theory, it is thought that the improved health of the birds (e.g., reduced bacterial, parasite and other pathogen loads) provides for an improved environment for bird growth. For example, mites are known to significantly reduce egg laying, egg weight, and egg quality. See Soares, et al., "Reduced productivity among confined laying hens infested by *Allopsoroptoides galli* (Mironov, 2013)," *Poult. Sci.* 95(4):819-22 (2016); and Vezzoli et al., "The effect of northern fowl mite (Omithonyssus sylviarum) infestation on hen physiology, physical condition, and egg quality," *Poult. Sci.* 95(5):1042-9 (2016). Also not to be limited by theory, it is thought that DHP gas results in decreased numbers of darkling beetles (and other non-feedmill foods) being ingested by the growing birds. It is well known, for example, that feeding on mealworms (e.g., darkling beetle larva) and darkling beetles lowers bird nutrition because the larva and beetles have low digestibility and the birds fill up with them rather than their feed. Thus, in addition to transmission of disease and diversion of feed as food for the pest insects, insect infestations (and darkling beetles and larva in particular) are thought to directly reduce production performance.

The present specification provides for methods of improving the feed conversion ratio (FCR) in a poultry flock by providing DHP gas at a concentration of at least 0.01 ppm. In an aspect, the FCR in a chicken flock grown in a grow-out house (e.g., at a broiler farm) in the presence of DHP gas is less than 1.5 during the first 21 days of rearing. In an aspect, the FCR in a chicken flock grown in a grow-out house (e.g., at a broiler farm) in the presence of DHP gas is less than 1.45 during the first 21 days of rearing. In an aspect, the FCR in a chicken flock grown in a grow-out house (e.g., at a broiler farm) in the presence of DHP gas is less than 1.42 during the first 21 days of rearing. The present methods further provide for improvements in FCR during later stages of broiler productions. In an aspect, the FCR in a chicken flock grown in a grow-out house (e.g., at a broiler farm) in the presence of DHP gas is less than 1.9 during days 21 to 43 of rearing. In an aspect, the FCR in a chicken flock grown in a grow-out house (e.g., at a broiler farm) in the presence of DHP gas is less than 1.85 during days 21 to 43 of rearing.

In an aspect according to the present specification, the methods include providing the DHP gas at up to 50 ppm to a grow-out house to increase the feed conversion ratio by 5% relative to the FCR in the absence of DHP gas. As provided herein, the improvement in FCR is determined relative to a flock of poultry of the same breed, same feed and grown under industry standard conditions but not exposed to DHP gas at any stage of production (e.g., no DHP during storage, incubation, rearing, etc.). In another aspect, the DHP gas level can be up to 10 ppm to increase the FCR by 5%. In a certain aspect, the DHP level ranges between 0.01 and 10 ppm. In an aspect, the concentration of DHP gas provided to a poultry space of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas provided to a poultry space of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to a poultry space of the present disclosure is between 1.0 ppm and 8.0 ppm, or between 5.0 ppm and 10.0 ppm.

In an aspect, the method provides for an increase in feed conversion of 6% or more when poultry are grown in the presence of DHP gas. In an aspect, the feed conversion ratio is increased by 7% or more, when poultry are grown in the presence of DHP gas. In another aspect, the feed conversion ratio is increased by 8% or more, when poultry are grown in the presence of DHP gas. In another aspect, the feed conversion ratio is increased by 9% or more, when poultry are grown in the presence of DHP gas. In another aspect, the feed conversion ratio is increased by 10% or more, when poultry are grown in the presence of DHP gas.

The present specification provides for methods of improving the feed conversion ratio (FCR) in an egg laying poultry flock by providing DHP gas at a concentration of at least 0.01 ppm. In an aspect, the FCR in a chicken flock grown in an egg-laying house in the presence of DHP gas is less than 2.00 during the laying period (e.g., about 18 to 90 weeks).

The present specification provides for methods of improving the feed conversion ratio (FCR) in an egg laying poultry flock by providing DHP gas at a concentration of at least 0.01 ppm wherein the feed conversion ratio is reduced by at least 5%.

The present specification provides for, and includes, improved eggs and chicks. As illustrated below, treatment with hydrogen peroxide results in enduring changes to eggs and hatched chickens that are evident from results demonstrating improved hatchability compared to equivalent non-DHP treated eggs. As shown in Example 15, treatment with DHP during on site storage of results in, but is not limited to, increased hatch weight and increased hatchability. As provided in Example 15, treatment with DHP during on site storage of results in, but is not limited to improved 7 day mortality. Surprisingly, these improvements are evident though DHP treatment was not continued during incubation. Not to be limited by theory, it is thought that a decreased bacterial and pathogen burden at the earliest stages of development improves the overall health of the egg. Alternatively, the DHP treatment may directly affect the health of the developing embryo. Thus, notably the improvement persists long after the initial treatment thought the eggs are subjected to ideal conditions for bacterial growth during incubation. Eggs treated during the on-site storage period are superior to untreated eggs.

The specification provides for an includes Dilute Hydrogen Peroxide (DHP) gas treated eggs comprising poultry eggs treated with up to 10 ppm DHP gas at a temperature below physiological zero for a storage period prior to incubation. In an aspect, the eggs are exposed to at least 0.001 ppm of DHP gas at a temperature below physiological zero for between 1 and 7 days. In an aspect, the eggs are treated for a storage period of between 1 and 7 days. In another aspect, the eggs are treated for storage period of at least 1 day. In another aspect, the eggs are treated for at least 2 days. In another aspect, the eggs are DHP gas treated during on-site storage for at least 3 days. In yet another aspect, the improved eggs are prepared by treating the eggs for at least 4 days. In an aspect, the eggs are exposed to at least 0.001 ppm of DHP gas at a temperature below physiological zero for at least one hour. In an aspect, the eggs are exposed to at least 0.001 ppm of DHP gas at a temperature below physiological zero for at least two hours. In an aspect, the eggs are exposed to at least 0.001 ppm of DHP gas at a temperature below physiological zero for at least four hours. In an aspect, the eggs are exposed to at least 0.001 ppm of DHP gas at a temperature below physiological zero for at least eight hours. In an aspect, the eggs are exposed to at least 0.001 ppm of DHP gas at a temperature below physiological zero for at least 12 hours. Additional details on the conditions to prepare improved eggs of the present disclosure are discussed above.

In an aspect, the improved eggs of the present disclosure have improved hatchability relative to non-DHP treated eggs. In an aspect, DHP treated eggs have an increased hatchability of 0.5% relative to non-DHP treated eggs. In another aspect, DHP treated eggs have an increased hatchability of 1.0% relative to non-DHP treated eggs. In another aspect, DHP treated eggs have an increased hatchability of 1.5% relative to non-DHP treated eggs. In another aspect, DHP treated eggs have an increased hatchability of 1.7% relative to non-DHP treated eggs.

Also provided for, and included, in the present specification, are DHP gas treated eggs having improved fertile hatchability relative to non-DHP treated eggs. In an aspect, the fertile hatchability is at least 0.5% greater than non-DHP treated eggs. In another aspect, the fertile hatchability is at least 1.0% greater than non-DHP treated eggs. In an aspect, the fertile hatchability is at least 1.5% greater than non-DHP treated eggs.

The improved eggs of the present disclosure have a reduced chick cull rate relative to eggs that have not been treated during on-site storage prior to incubation. In an aspect, the cull rate is reduced by at least 1% relative to the cull rate of non-DHP treated eggs.

The present disclosure further includes, and provides for, DHP gas treated poultry eggs having a reduced level of contaminated eggs at transfer. Notably, as provided in Example 15, eggs having micro-cracks did not become infected during the incubation period. This is significant because contaminated eggs if present during incubation can explode (e.g., "boomers") that can contaminate the entire clutch of eggs in an incubator. As shown in Table 6, despite the presence of cracked eggs (and eggs that may not have observable cracks), none of the eggs become contaminated. In contrast, non-treated eggs are observed in the non-treated samples. In an aspect, the number of contaminated eggs is reduced for DHP gas treated poultry eggs. In an aspect, the number of contaminated eggs after incubation is reduced for DHP gas treated poultry eggs. In an aspect, contaminated eggs among DHP gas treated poultry eggs are reduced at least 5% relative to non-DHP treated eggs.

The specification further includes, and provides for, improved healthier chicks having decreased seven day mortality when raised on a grow out farm under standard commercial conditions compared to chicks obtained from non-DHP gas treated eggs. In an aspect, the improved chicks are hatched from eggs that have been treated only during on site storage as provided in the present specification. In an aspect, the improved chicks are treated with DHP gas according the methods of the present specification during on-site storage and during incubation. In an aspect, the improved chicks have a decreased seven (7) day mortality compared to non-DHP gas treated eggs. In an aspect, the improved, chicks have an improved food conversion ratio. In an aspect, the food conversion ratio (FCR) is at least 1.0% greater than the FCR for chicks hatched from untreated eggs. In an aspect, the FCR is at least 2.5% greater than chick hatched from untreated eggs. In yet another aspect, DHP treatment provides for chicks having at least 5% greater FCR compared to chicks that have not been treated. The chicks hatched from DHP treated eggs are healthier and have a decreased level of condemnation compared to untreated eggs. In an aspect, the number of ante-mortem condemnations is reduced. In another aspect, the number of post-mortem condemnations is reduced.

The improved chicks of the present specification have reduced levels of bacteria when measured by oropharyngeal swabbing. In another aspect, the improved chicks hatched from DHP treated eggs have decreased levels of bacteria when measured by cloacal swabbing. In a further aspect, the improved chicks of the present disclosure have decreased levels of bacteria when a sample is obtained by oropharyngeal or cloacal swab when compared to a chicks hatched from non-DHP treated eggs.

DHP treatment of eggs during on-site storage results in improved, healthier chicks compared to chicks hatched from non-DHP treated eggs. In an aspect the chicks are improved by treatment of the eggs during storage with DHP gas at a concentration between 0.001 and 10 ppm. In another aspect, the chicks are improved by treating the eggs during on-site storage and during incubation with DHP gas at a concentration between 0.001 and 10 ppm. In an aspect, the on farm mortality of chicks hatched from treated eggs is reduced. In an aspect, on farm mortality after one week is reduced by at least 1% compared to chicks hatched from non-DHP treated eggs. In an aspect, on farm mortality after one week is reduced by at least 2% compared to chicks hatched from non-DHP treated eggs. In an aspect, on farm mortality after one week is reduced by at least 3% compared to chicks hatched from non-DHP treated eggs.

The improved chicks according to the present specification includes chicks having an improved food conversion ratio compared to chicks obtained from non-DHP gas treated eggs. Ina aspect the improved FCR is at least 5% greater than the FCR when compared to non-DHP treated eggs. Also included and provided for are chicks that have decreased levels of either ante- or post-mortem condemnation. As used herein, "poultry eggs" include all types of poultry, including but not limited to, chickens, turkeys, quails, ducks, and geese. As used herein, the term "poultry" or "birds" refers to chicks, pullets, broilers, layers, hens, roosters, capons, and broilers. It will be appreciated by one of ordinary skill in the art, that the methods and devices of the present specification can be applied to a single egg or bird, modern production methods include large numbers. For example, the average capacity of a hatchery is about 2,750,000 per year, and the average capacity of an incubator is 10,000.

As used herein, the term "poultry space" refers to any one of a space used for holding, raising, hatching or otherwise accommodating poultry at various stages of the poultry life cycle. Poultry spaces include, but are not limited to, an egg room (or receiving area), an incubator (setting, hatching, or combination), a grow-out house, a laying house, and a coop. As provided herein, a poultry space includes spaces found at a primary breeder facility, a breeder farm, a hatchery, and a small farm. Also included, and provided for, are poultry spaces wherein poultry are kept as pets. In an aspect, a poultry space is a pullet house. In another aspect, a poultry space is a lay house. In another aspect, a poultry space is a lay house egg/ante room. In yet another aspect, a poultry space is a hatchery. In another aspect, a poultry space is an egg room. In an aspect, a poultry space is an incubator and hatchery room. In an aspect according to the present specification, a poultry space includes a packing room (egg, chick, pullet, adult, etc.). In an aspect, a poultry space is a chick holding room. In an aspect, the poultry space is a breeder house. Other poultry spaces include various containers and rooms for storing, shipping, or raising poultry. As provided herein, any poultry space can be provided with DHP at a concentration of at least 0.01 ppm and is thus provided the benefits of DHP with regard to improving poultry health. DHP containing poultry spaces also provide protection from introduction of poultry diseases by preventing or repelling various arthropods that can be disease vectors as well as killing any adventitious bacteria, viruses, and fungi. By continuously providing DHP, poultry spaces can be made resistant to the intentional introduction of poultry pathogens.

The present disclosure provides for and includes a modified egg room (egg receiving area) comprising dry hydrogen peroxide (DHP) at a concentration of between 0.01 ppm and 50 ppm. In an aspect, the egg room is provided DHP at a concentration of less than 10 ppm. The present disclosure provides for a method of decreasing the number of contaminated eggs (e.g., "ROTS") comprising providing DHP to eggs in an egg room (e.g., receiving room) prior to moving the stored eggs to a hatching incubator.

The present disclosure provides for and includes a modified setting incubator comprising a DHP generator capable of maintaining dry hydrogen peroxide (DHP) at a concentration of between 0.01 ppm and 50 ppm. In a certain aspect, the DHP gas level in a modified setting incubator can be up to 50 ppm. In another aspect, the DHP gas level in a modified setting incubator can be up to 10 ppm. In a certain aspect, the DHP level ranges between 0.01 and 10 ppm. In an aspect, the concentration of DHP gas in a modified setting incubator of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas in a modified setting incubator of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas in a modified setting incubator of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas in a modified setting incubator of the present disclosure is between 1.0 ppm and 8.0 ppm, or between 5.0 ppm and 10.0 ppm. In another aspect, the concentration of DHP during hatching incubation cycles between higher and lower concentrations of DHP.

The present disclosure provides for and includes a modified hatching incubator comprising a DHP generator capable of maintaining dry hydrogen peroxide (DHP) at a concentration of between 0.01 ppm and 50 ppm. In a certain aspect, the DHP gas level in a modified hatching incubator can be up to 50 ppm. In another aspect, the DHP gas level in a modified hatching incubator can be up to 10 ppm. In a certain aspect, the DHP level ranges between 0.01 and 10 ppm. In an aspect, the concentration of DHP gas in a modified hatching incubator of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas in a modified hatching incubator of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas in a modified hatching incubator of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas in a modified hatching incubator of the present disclosure is between 1.0 ppm and 8.0 ppm, or between 5.0 ppm and 10.0 ppm. In another aspect, the concentration of DHP during hatching incubation cycles between higher and lower concentrations of DHP.

The present disclosure provides for and includes a modified grow-out house comprising a DHP generator capable of maintaining dry hydrogen peroxide (DHP) at a concentration of between 0.01 ppm and 50 ppm. In a certain aspect, the DHP gas level in a modified grow-out house can be up to 50 ppm. In another aspect, the DHP gas level in a modified grow-out house can be up to 10 ppm. In a certain aspect, the DHP level ranges between 0.01 and 10 ppm. In an aspect, the concentration of DHP gas in a modified grow-out house of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas in a modified grow-out house of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas in a modified grow-out house of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas in a modified grow-out house of the present disclosure is between 1.0 ppm and 8.0 ppm, or between 5.0 ppm and 10.0 ppm. In another aspect, the concentration of DHP during hatching incubation cycles between higher and lower concentrations of DHP.

The present disclosure provides for and includes a modified egg-laying house comprising a DHP generator capable of maintaining dry hydrogen peroxide (DHP) at a concentration of between 0.01 ppm and 50 ppm. In a certain aspect, the DHP gas level in a modified egg-laying house can be up to 50 ppm. In another aspect, the DHP gas level in a modified egg-laying house can be up to 10 ppm. In a certain aspect, the DHP level ranges between 0.01 and 10 ppm. In an aspect, the concentration of DHP gas in a modified egg-laying house of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas in a modified egg-laying house of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas in a modified egg-laying house of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas in a modified egg-laying house of the present disclosure is between 1.0 ppm and 8.0 ppm, or between 5.0 ppm and 10.0 ppm. In another aspect, the concentration of DHP during hatching incubation cycles between higher and lower concentrations of DHP.

DHP directly helps with the reduction of, or prevention of transmission of, diseases by lowering the amount of disease organism in the environment, both in the air and on environmental surfaces. DHP has the advantage over other methods of doing so continually. Thus, a complete eradication is not required and the reduced pathogen load results in overall improved health. Importantly, DHP gas can prevent the spread of infectious diseases. In an aspect, DHP gas can be provided to mitigate or reduce the effects of infectious disease that is purposely introduced to a poultry facility.

DHP devices can be installed on a stand-alone basis or in the HVAC system. Non-limiting examples of suitable stand-alone and HVAC devices are described in International Patent Publication No. WO 2010/093796 and International Patent Publication No. WO 2015/171633. It will be appreciated that a DHP generating device can be incorporated into additional devices by providing a source of UV light, an air permeable substrate structure ("sail") having a catalyst on its surface and an air distribution mechanism that provides a flow of air through the air-permeable substrate structure when illuminated with a UV light. For example, an HVAC device as described can be incorporated into a stand-alone device by attaching a section of HVAC duct and a fan to the device. This duct/device/fan combination can then be placed into any suitable space. In an aspect, the duct/device/fan combination further includes a high capacity filter. It will also be appreciated that an HVAC device (or duct/device/fan combination) can be installed separate from an HVAC system. That is, multiple duct/device/fan combinations can be installed, each with their own duct and fan to increase the levels of DHP provided or to provide sufficient levels to maintain DHP at a level of at least 0.01 ppm even in very large spaces. For example, a grow-out house comprising 8500 $m^3$ can be prepared by incorporating 30 HVAC type units of the current design. It is anticipated that improved designs will reduce the number of devices necessary to maintain the desired levels of DHP gas.

The present disclosure provides for and includes additional modifications to a poultry facility to improve protected areas and reduce contamination. Using an "Envelope Concept," a protected area is defined, then steps to control conditions that could dilute the DHP within the envelope are taken. In an aspect, a protected area is an egg room that is modified to include curtains to reduce the exchange of air with the outside, non-protected area. In another aspect, protected areas are fitted with a vestibule to further isolate the protected area. In an aspect, the vestibule can be maintained at a positive pressure to prevent potentially contaminated air from entering. Protected areas can also be further modified to remove non-essential items such as pallets, empty cardboard boxes and crates that can be a source of contamination or reduce the air flow throughout the poultry space.

As used herein, purified hydrogen peroxide gas (PHPG) and dry hydrogen peroxide (DHP) gas are used interchangeably. PHPG and DHP have also been referred to as "dilute hydrogen peroxide." Purified hydrogen peroxide gas as used herein is non-hydrated (e.g., dry), substantially free of ozone, plasma species, and organic species. Also as used herein, the level of PHPG in a poultry space is determined as the steady state level of PHPG in a poultry space. Poultry spaces according to the present disclosure comprising DHP gas are poultry spaces having a steady state concentration of DHP gas of at least 0.01 ppm for a period of at least 15 minutes. In an aspect, the poultry space is maintained at a level of between 0.01 ppm and 50 ppm. Notably, during normal use, PHPG is used up as it reacts with organic compounds, reacts with microorganisms, or otherwise degrades and thus must be continually replaced. In practice, it is anticipated that the poultry spaces according to the present disclosure, are maintained in a DHP gas containing state by the constant production of PHPG via one or more devices as part of the heating ventilation and air conditioning (HVAC) system or supplied by one or more stand-alone PHPG producing devices. In a certain aspect, an incubator (e.g., setting, hatching or combination) can have an integrated PHPG producing device. In other aspects, the room containing the incubators is supplied with PHPG. Poultry spaces having integrated PHPG producing devices provide for easy movement of the poultry spaces between rooms and buildings. Notably, given the safety of PHPG, a poultry space can be provided merely by placing a container in an occupied building being treated with PHPG. A poultry space having DHP gas is a space that is provided PHPG at a level of at least 0.01 ppm. In a certain aspect, DHP gas is PHPG provided to a poultry space at a level of between 0.01 ppm and 1.0 ppm. In another aspect, DHP gas is PHPG provided to a poultry space at a level of up to 10.0 ppm. Unless indicated, a DHP poultry space is a poultry space provided with DHP such that the space, when empty maintains a level of DHP of at least 0.01 ppm.

As used herein, the term "substantially free of ozone" means an amount of ozone below about 0.015 ppm ozone. In an aspect, "substantially free of ozone" means that the amount of ozone produced by the device is below or near the level of detection (LOD) using conventional detection means. Ozone detectors are known in the art and have detection thresholds in the parts per billion using point ionization detection. A suitable ozone detector is the Honeywell Analytics Midas® gas detector capable of detecting 0.036 ppm to 0.7 ppm ozone.

As used herein, substantially free of hydration means that the hydrogen peroxide gas is at least 99% free of water molecules bonded by electrostatic attraction and London Forces.

Also as used herein, a PHPG that is substantially free of plasma species means hydrogen peroxide gas that is at least 99% free of hydroxide ion, hydroxide radical, hydronium ion, and hydrogen radical.

As used herein the term "poultry disease" refers to one or more diseases of poultry caused by bacteria, viruses, fungi, *mycoplasma*, and parasites. Table 3 lists many of the common diseases of poultry and provides examples of known disease agents. Table 3, while extensive, is not comprehensive and the present specification provides for and includes poultry diseases that result in lower productivity and health of the affected birds. The present specification provides for reducing or preventing poultry diseases comprising providing dry hydrogen peroxide (DHP) at a concentration of between 0.01 ppm and 50 ppm. In an aspect, the specification provides for reducing the transmission of an airborne disease by providing dry hydrogen peroxide (DHP) at a concentration of between 0.01 ppm and 50 ppm. In a certain aspect, the DHP gas level for reducing one or more poultry diseases can be up to 50 ppm. In another aspect, the DHP gas level for reducing one or more poultry diseases can be up to 10 ppm. In a certain aspect, the DHP gas level for reducing one or more poultry diseases ranges between 0.01 ppm and 10 ppm. In an aspect, the DHP gas level for reducing one or more poultry diseases according to the present disclosure is at least 0.08 ppm. In another aspect, the concentration of DHP gas for reducing one or more poultry diseases is at least 1.0 ppm. In yet another aspect, the concentration of DHP gas for reducing one or more poultry diseases is at least 1.5 ppm. In an aspect, the concentration of DHP gas for reducing one or more poultry diseases of the present disclosure is at least 2.0 ppm. In another aspect, the concentration of DHP gas for reducing one or more poultry diseases is at least 3.0 ppm. In an aspect, the concentration of DHP gas is at least 4.0 ppm. In an aspect, the concentration of DHP gas is at least 5.0 ppm. In another aspect, the concentration of DHP gas for reducing one or more poultry diseases of the present disclosure is at least 6.0 ppm. In an aspect, the concentration of DHP gas is less than 10 ppm. In an aspect, the concentration of DHP gas for reducing one or more poultry diseases is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas for reducing one or more poultry diseases is between 0.08 ppm and 2.0 ppm. In yet another aspect, the concentration of DHP gas is between 1.0 ppm and 3.0 ppm. In an aspect, the concentration of DHP gas for reducing one or more poultry diseases of the present disclosure is between 1.0 ppm and 8.0 ppm, or between 5.0 ppm and 10.0 ppm.

In an aspect, transmission of an airborne disease can be prevented. In an aspect, the prevented airborne disease can be naturally occurring through the adventitious introduction of an airborne pathogen. In another aspect, airborne pathogen can be purposely introduced to a poultry facility through a criminal act. Thus, the present specification provides for the mitigation or reduction of pathogen caused disease purposely and illegally introduced, for example as an act of terrorism. In other aspects, DHP gas can be provided continuously to a production facility to reduce the damages should there be an introduction of a pathogen into a poultry production facility. By providing DHP gas continually, the risk of damages through either an intentional or a non-intentional act will be greatly diminished.

TABLE 4

Poultry Diseases

| Disease | Type | Disease Agent |
|---|---|---|
| Amyloidosis | Bacterial | *Enterococcus faecalis* and *Mycoplasma synoviae* |
| Anatipestifer Disease, New Duck Syndrome, Duck Septicaemia | Bacterial | Riemerella anatipestifer, syn Pasteurella, or Moraxella a |

TABLE 4-continued

| Poultry Diseases | | |
|---|---|---|
| Disease | Type | Disease Agent |
| Arizona infection, Arizonosis | Bacterial | *Salmonella enterica* subsp. *arizonae* (*S. arizonae*); [vertical] |
| Beak Necrosis | Bacterial | Gram-positive |
| Botulism | Bacterial | *Clostridium botulinum* |
| Breast Blister | Bacterial | *Staphylococcus* spp. |
| *Campylobacter* Infection | Bacterial | *Campylobacter* spp. |
| *Chlamydiosis*, Psittacosis, Ornithosis | Bacterial | *Chlamydia psittaci* |
| Colisepticemia | Bacterial | *Escherichia coli* |
| Dysbacteriosis, Non-specific Bacterial Enteritis | Bacterial | |
| Endocarditis | Bacterial | *Staphylococci, Streptococci, Erysipelothrix* |
| Epiphysiolysis | Bacterial | Complex, bacterial only one factor |
| Erysipelas | Bacterial | *Erysipelothrix insidiosa* (*E. rhusiopathiae*) |
| Femoral Head Necrosis—FHN | Bacterial | *Staphylococci, E. coli, Streptococci* |
| Fowl Cholera, Pasteurellosis | Bacterial | *Pasteurella multocida* |
| Gangrenous Dermatitis, Necrotic Dermatitis | Bacterial | *Clostridium septicum, Staphylococcus aureus, Clostridium noyvi I oedematiens* |
| Infectious Coryza | Bacterial | *Haemophilus paragallinarum* |
| Necrotic Enteritis | Bacterial | *Clostridium perfringens* |
| Ornithobacterium Infection, ORT | Bacterial | *Ornithobacterium rhinotracheale* |
| Pseudotuberculosis | Bacterial | *Yersinia pseudotuberculosis* |
| *Salmonella Gallinarum*, Fowl Typhoid | Bacterial | *Salmonella Gallinarum* |
| *Salmonella Pullorum*, Pullorum Disease, 'Bacillary White Diarrhoea' | Bacterial | *Salmonella Pullorum*; [vertical] |
| Salmonellosis, Paratyphoid Infections | Bacterial | *S. Derby, S. Newport, S. Montevideo, S. Anatum, S. Bredeney* |
| Salmonellosis, S. Enteritidis and S. Typhimurium infections | Bacterial | *Salmonella enteritidis; S. Typhimurium;* [vertical] |
| Spirochaetosis | Bacterial | *Borrelia anserina* |
| Staphylococcosis, Staphylococcal Arthritis, Bumble Foot | Bacterial | *Staphylococcus; S. aureus* |
| Streptococcus bovis Septicaemia | Bacterial | *Streptococcus bovis* |
| Turkey Coryza | Bacterial | *Bordetella avium* |
| Ulcerative Enteritis, Quail disease | Bacterial | *Clostridium colinum* |
| Vibrionic Hepatitis, Avian Infectious Hepatitis | Bacterial | *Vibrio* |
| Yolk Sac Infection, Omphallitis | Bacterial | *E. coli, Staphylococci, Proteus* spp., *Pseudomonas* |
| Haemorrhagic Disease, Aplastic Anaemia, Haemorrhagic Anaemia | Unknown (complex) | Mycotoxin and viral |
| Intussusception | Parasite | Coccidiosis, worms, enteritis |
| PEMS and Spiking Mortality of Turkeys | Unknown (complex) | Bacterial and viral |
| Pullet disease, Bluecomb, Avian Monocytosis | Unknown (complex) | Toxin and Viral |
| Respiratory Disease Complex | Unknown (complex) | Dust, ammonia, (Infectious Bronchitis, Avian pneumovirus, Lentogenic Newcastle disease virus, vaccinal and field strains; Ornithobacterium rhinotracheale, E. coli |
| Salpingitis | Unknown (complex) | Mycoplasma and bacteria |
| Spiking Mortality of Chickens | Unknown (complex) | Possible viral component |
| Twisted leg | Unknown (complex) | Genetics, nutrition, environment |
| Spradle leg or Splay leg | Unknown (complex) | |
| Aspergillosis | Fungal | Aspergillus fumigatus |
| Candidiasis, Moniliasis, Thrush | Fungal | Candida albicans |
| Dactylariosis | Fungal | Dactylaria gallopava |
| Favus | Fungal | Trichophyton gallinae |
| Mycotoxicosis | Fungal | From mold toxins: Aspergillus, Fusarium, |
| Mycoplasma gallisepticum infection, | Mycobacterial | Mycoplasma gallisepticum |
| Mycoplasma immitans infection | Mycobacterial | Mycoplasma immitans |
| Mycoplasma iowae infection, M.i. | Mycobacterial | Mycoplasma iowae |
| Mycoplasma meleagridis infection, M.m. | Mycobacterial | Mycoplasma meleagridis |
| Mycoplasma synoviae infection, M.s. Infectious Synovitis | Mycobacterial | Mycoplasma synoviae |
| Tuberculosis | Mycobacterial | *Mycobacterium avium* |
| Bedbug Infestation | Parasite | Cimex lectularius |
| Biting Lice | Parasite | *Menocanthus* spp.; *Menocanthus stramineus* |
| Blackfly Infestation | Parasite | Simuliidae |
| Caecal | Parasite | Eimeria tenella |

TABLE 4-continued

| Poultry Diseases | | |
|---|---|---|
| Disease | Type | Disease Agent |
| Caecal Worm | Parasite | Heterakis gallinae |
| Capillariasis - Haiiworm Infection | Parasite | *Capillaria* spp.; C. obsignata; C. contorta |
| Cropworms | Parasite | *Capillaria* spp. and Gongylonema ingluvicola |
| Duodenum | Parasite | E praecox |
| Gape | Parasite | Syngamus trachea |
| Gizzard worms - Chickens | Parasite | Cheilospirura, Streptocara, and Histiocephalus |
| Gizzard worms - Geese | Parasite | Amidostomum anseris |
| Hexamitiasis | Parasite | Hexamita meleagridis |
| Ileorectal | Parasite | E brunetti |
| Kidney | Parasite | Eimeria truncata |
| Leukocytozoonosis | Parasite | *Leucocytozoon* species |
| Mid-intestinal | Parasite | Emaxima |
| Mid-intestinal | Parasite | E necatrix |
| Proventricular Worms | Parasite | Dispharynx, Tetrameres and Cyrnea |
| Red Mite and Northern Fowl Mite | Parasite | Dermanyssus gallinae; Omithonyssus bursae |
| Small intestine | Parasite | E mitis |
| Small intestine | Parasite | E. anseris |
| Upper Intestinal | Parasite | E acervulina |
| Coccidiosis | Parasite (direct) | *Eimeria* spp. |
| Cryptosporidiosis | Parasite (direct) | *Cryptosporidium* spp.; *Cryptosporidium baileyi*; C. meleagridis |
| Histamonosis, Histomoniasis, Blackhead | Parasite (direct) | Histomonas melagridis |
| Roundworm, large - Ascaridia | Parasite (indirect) | A. galli; A. dissimilis; A. columbae |
| Deplumimg and Scaly Leg Mites | Parasitic | *Knemidocoptes* spp |
| Tapeworms, Cestodes | Parasitic | Cestodes |
| Ticks | Parasitic | Argas persicus |
| Trichomoniasis, Canker, Frounce | Parasitic (direct) | Trichomonas gallinae |
| Avian Encephalomyelitis Egg Drop | Viral | Picomaviridae; tremovirus |
| Avian Encephalomyelitis, Epidemic Tremors | Viral | Picomaviridae |
| Avian Influenza-Highly Pathogenic (HPAI), Fowl Plague | Viral | Influenza; HSN 1 |
| Avian Leukosis (Serotype J), Myelocytomatosis | Viral | Avian sarcoma leukosis virus; Alpharetrovirus |
| Avian Leukosis, Lymphoid Leukosis, Leukosis/Sarkoma Group | Viral | Avian sarcoma leukosis virus |
| Avian Rhinotracheitis 'Swollen Head Syndrome' | Viral | Avian pneumovirus (APV) |
| Big Liver and Spleen Disease | Viral | Avian Hepevirus |
| Chicken Anaemia | Viral | Chicken Anaemia Virus or CAV [vertical] |
| Duck Viral Hepatitis | Viral | Picomavirus |
| Duck Virus Enteritis, Duck Plague | Viral | Herpesvirus |
| Egg Drop Syndrome 76 | Viral | Adenovirus BC14, 127 [vertical] |
| Equine Encephalitis (EEE, WEE, VEE) | Viral | Alphavirus |
| Fowl Pox, Pox, Avian Pox | Viral | Poxviridae |
| Goose Parvovirus (Derzsy's Disease) | Viral | Parvoviridae |
| Haemorrhagic Enteritis | Viral | Adenovirus (Type II) |
| Hydropericardium-Hepatitis Syndrome, Angara Disease | Viral | Adenovirus |
| Inclusion Body Hepatitis | Viral | Adenovirus |
| Infectious Bronchitis, IB | Viral | Coronavirus |
| Infectious Bronchitis, IB - 793b Variant Sudden Death Syndrome in Broiler Parents | Viral | Coronavirus |
| Infectious Bronchitis, IB Egg-layers | Viral | Coronavirus |
| Infectious Bursal Disease, IBD, Gumboro | Viral | Bimaviridae |
| Infectious Laryngotracheitis, ILT | Viral | Herpesvirus |
| Lymphoproliferative Disease (LPD) | Viral | Type C retrovirus |
| Malabsorption Syndrome, Runting/Stunting | Viral | Enteroviruses, Enterovirus-like particles, Reoviruses, Rotavirus etc. |
| Marek's disease | Viral | Herpes |
| Newcastle Disease (Paramyxovirus 1) | Viral | Paramyxovirus 1 |
| Paramyxovirus 2 - Yucaipa Disease | Viral | Paramyxovirus PMV-2 |
| Paramyxovirus-3 | Viral | Paramyxovirus PMV-3 |
| Paramyxovirus-6 | Viral | Paramyxovirus PMV-6 |
| Respiratory Adenovirus Infection, 'Mild Respiratory Disease' | Viral | Adenovirus |
| Reticuloendotheliosis, Lymphoid Tumour Disease | Viral | Retroviridae |
| Rotavirus Infection | Viral | Reoviridae |

TABLE 4-continued

Poultry Diseases

| Disease | Type | Disease Agent |
| --- | --- | --- |
| Transmissible Enteritis, Bluecomb | Viral | Coronaviruses |
| Turkey Rhinotracheitis (Adult) | Viral | Paramyxoviridae |
| Turkey Rhinotracheitis (in rear) | Viral | Paramyxoviridae |
| Turkey Viral Hepatitis | Viral | Unidentified |
| Viral Arthritis | Viral | reovirus |

Health and safety of poultry is a primary concern of the poultry industry, not only to the birds themselves, but as a source of infection and disease to humans and other animals. As noted above, despite the efforts and the application of many different compounds and methods, the problem of bacterial contamination and infection of poultry remains. The present specification provides for, and includes, methods for the reduction of bacteria in poultry including, eggs, chickens, adults, and poultry spaces. Exemplary types of bacteria that are reduced in poultry are provided above in Table 3. Bacteria that are reduced by the present methods include but are not limited to Bordetella avium, Borrelia anserina, Campylobacter spp., Chlamydia psittaci, Clostridium spp. (C. botulinum, C. cilium, C. noyvi, C. oedematiens, C. peifringens, C. septicum), Enterococcus faecalis, Erysipelothrix spp. (E. insidiosa or E. rhusiopathiae), Escherichia coli, Haemophilus paragallinarum, Mycoplasma synoviae, Ornithobacterium rhinotracheale, Pasteurella multocida, Proteus spp., Pseudomonas spp., S. typhimurium, Salmonella spp. (S. anatum, S. bredeney, S. derby, S. enterica subsp. arizonae (S. arizonae), S. enteritidis, S. gallinarum, S. montevideo, S. newport, S. pullorum, Staphylococci spp. (S. aureus), Streptococci spp. (S. bovis), Vibrio, and Yersinia pseudotuberculosis. In an aspect, the bacteria are reduced in poultry spaces or on eggs, chicks, pullets, or adults by at least 5 fold over untreated poultry spaces or eggs, chicks, pullets, or adults. In an aspect, the bacteria are reduced in poultry spaces or on eggs, chicks, pullets, or adults by at least 10 fold over untreated poultry spaces or eggs, chicks, pullets, or adults. In an aspect, the bacteria are reduced in poultry spaces or on eggs, chicks, pullets, or adults by at least 100 fold over untreated poultry spaces or eggs, chicks, pullets, or adults. In an aspect, the bacteria are reduced in poultry spaces or on eggs, chicks, pullets, or adults by at least $10^3$ fold over untreated poultry spaces or eggs, chicks, pullets, or adults. In an aspect, the poultry spaces, eggs, chicks, pullets, or adults are treated with at least 0.01 ppm DHP continuously. In an aspect, the poultry spaces, eggs, chicks, pullets, or adults are treated with at least 0.01 ppm DHP for at least 1 hour daily. In another aspect, the poultry spaces, eggs, chicks, pullets, or adults are treated with at least 0.01 ppm DHP for at least 2 hours daily. In yet another aspect, the poultry spaces, eggs, chicks, pullets, or adults are treated with at least 0.01 ppm DHP for at least 4 hours daily. In another aspect, the poultry spaces, eggs, chicks, pullets, or adults are treated with at least 0.01 ppm DHP for at least 8 hours daily. In yet another aspect, the poultry spaces, eggs, chicks, pullets, or adults are treated with at least 0.01 ppm DHP for at least 12 hours daily. In another aspect, the poultry spaces, eggs, chicks, pullets, or adults are treated with at least 0.01 ppm DHP continuously. In a certain aspect, the bacteria is a species of the genus Salmonella.

In an aspect, the present specification provides for, and includes, a method of reducing the bacterial contamination of poultry eggs comprising providing DHP at a concentration of at least 0.01 ppm during pre-incubation storage. In another aspect, the present specification provides for a method of reducing the bacterial contamination of poultry eggs comprising providing DHP at a concentration of at least 0.01 ppm during setting incubation. In another aspect, the present specification provides for a method of reducing the bacterial contamination of poultry eggs comprising providing DHP at a concentration of at least 0.01 ppm during hatching incubation. The present specification also provides for reducing the contamination of hatching incubators comprising provided DHP at a concentration of at least 0.01 ppm after the chicks are removed. In an aspect, the level of DHP provided to reduce the bacterial contamination of poultry eggs during hatching incubation is at least 0.001 ppm. In an aspect, the level of DHP provided to reduce the bacterial contamination of poultry eggs during hatching incubation is at least 1.0 ppm. In another aspect, the level of DHP provided to reduce the bacterial contamination of poultry eggs during hatching incubation is at least 1.5 ppm. In another aspect, the level of DHP provided to reduce the bacterial contamination of poultry eggs during hatching incubation is at least 2.0 ppm. In another aspect, the level of DHP provided to reduce the bacterial contamination of poultry eggs during hatching incubation is less than 10.0 ppm. In an aspect, the amount of DHP provided to reduce the bacterial contamination of poultry eggs during hatching incubation or during setting incubation is less than 100 molecules $H_2O_2$ per cubic micron of air. In a certain aspect, the bacteria is a species of the genus Salmonella Campylobacter, Listeria, Escherichia coli or Enterococcus.

In another aspect, the present specification provides for and includes a method of reducing the transmission of bacteria to newly hatched poultry chicks during hatching incubation comprising providing DHP at a concentration of at least 0.01 ppm during hatching incubation. In an aspect, the method includes reducing the level of bacterial contamination of "fluff" during the hatching process, thereby reducing the transmission between chicks. In an aspect, the level of DHP provided to the transmission of bacteria to newly hatched poultry chicks during hatching incubation is at least 1.0 ppm. In another aspect, the level of DHP provided to the transmission of bacteria to newly hatched poultry chicks during hatching incubation is at least 1.5 ppm. In another aspect, the level of DHP provided to the transmission of bacteria to newly hatched poultry chicks during hatching incubation is at least 2.0 ppm. In another aspect, the level of DHP provided to the transmission of bacteria to newly hatched poultry chicks during hatching incubation is less than 10.0 ppm. In an aspect, the amount of DHP provided to the transmission of bacteria to newly hatched poultry chicks during hatching incubation is less than 100 molecules $H_2O_2$ per cubic micron of air.

In another aspect, the present specification provides for and includes a method of reducing the transmission of Salmonella to newly hatched poultry chicks during hatching incubation comprising providing DHP at a concentration of at least 0.01 ppm during hatching incubation. In an aspect, the method includes reducing the level of Salmonella contamination of "fluff" during the hatching process, thereby reducing the transmission between chicks. In an aspect, the level of DHP provided to the transmission of Salmonella to newly hatched poultry chicks during hatching incubation is at least 1.0 ppm. In another aspect, the level of DHP provided to the transmission of Salmonella to newly hatched poultry chicks during hatching incubation is at least 1.5 ppm. In another aspect, the level of DHP provided to the transmission of Salmonella to newly hatched poultry chicks during hatching incubation is at least 2.0 ppm. In another aspect, the level of DHP provided to the transmission of Salmonella to newly hatched poultry chicks during hatching incubation is less than 10.0 ppm. In an aspect, the amount of DHP provided to the transmission of Salmonella to newly hatched poultry chicks during hatching incubation is less than 100 molecules $H_2O_2$ per cubic micron of air.

In another aspect, the present specification provides for and includes a method of reducing the transmission of Campylobacter to newly hatched poultry chicks during hatching incubation comprising providing DHP at a concentration of at least 0.01 ppm during hatching incubation. In an aspect, the method includes reducing the level of Campylobacter contamination of "fluff" during the hatching process, thereby reducing the transmission between chicks. In an aspect, the level of DHP provided to the transmission of Campylobacter to newly hatched poultry chicks during hatching incubation is at least 1.0 ppm. In another aspect, the level of DHP provided to the transmission of Campylobacter to newly hatched poultry chicks during hatching incubation is at least 1.5 ppm. In another aspect, the level of DHP provided to the transmission of Campylobacter to newly hatched poultry chicks during hatching incubation is at least 2.0 ppm. In another aspect, the level of DHP provided to the transmission of Campylobacter to newly hatched poultry chicks during hatching incubation is less than 10.0 ppm. In an aspect, the amount of DHP provided to the transmission of Campylobacter to newly hatched poultry chicks during hatching incubation is less than 100 molecules $H_2O_2$ per cubic micron of air.

In another aspect, the present specification provides for and includes a method of reducing the transmission of Listeria to newly hatched poultry chicks during hatching incubation comprising providing DHP at a concentration of at least 0.01 ppm during hatching incubation. In an aspect, the method includes reducing the level of Listeria contamination of "fluff" during the hatching process, thereby reducing the transmission between chicks. In an aspect, the level of DHP provided to the transmission of Listeria to newly hatched poultry chicks during hatching incubation is at least 1.0 ppm. In another aspect, the level of DHP provided to the transmission of Listeria to newly hatched poultry chicks during hatching incubation is at least 1.5 ppm. In another aspect, the level of DHP provided to the transmission of Listeria to newly hatched poultry chicks during hatching incubation is at least 2.0 ppm. In another aspect, the level of DHP provided to the transmission of Listeria to newly hatched poultry chicks during hatching incubation is less than 10.0 ppm. In an aspect, the amount of DHP provided to the transmission of Listeria to newly hatched poultry chicks during hatching incubation is less than 100 molecules $H_2O_2$ per cubic micron of air.

In another aspect, the present specification provides for and includes a method of reducing the transmission of Escherichia coli to newly hatched poultry chicks during hatching incubation comprising providing DHP at a concentration of at least 0.01 ppm during hatching incubation. In an aspect, the method includes reducing the level of Escherichia coli contamination of "fluff" during the hatching process, thereby reducing the transmission between chicks. In an aspect, the level of DHP provided to the transmission of Escherichia coli to newly hatched poultry chicks during hatching incubation is at least 1.0 ppm. In another aspect, the level of DHP provided to the transmission of Escherichia coli to newly hatched poultry chicks during hatching incubation is at least 1.5 ppm. In another aspect, the level of DHP provided to the transmission of Escherichia coli to newly hatched poultry chicks during hatching incubation is at least 2.0 ppm. In another aspect, the level of DHP provided to the transmission of Escherichia coli to newly hatched poultry chicks during hatching incubation is less than 10.0 ppm. In an aspect, the amount of DHP provided to the transmission of Escherichia coli to newly hatched poultry chicks during hatching incubation is less than 100 molecules $H_2O$ 2 per cubic micron of air.

The present specification provides for and includes preventing the transmission of viral diseases in poultry. In an aspect, the viral disease is selected from Adenoviridae (adenovirus, Adenovirus (Type II), Adenovirus BC14), Bimaviridae (Avibimavirus, infectious bursal disease virus), Circoviridae (Chicken Anaemia Virus (CAV)), Coronavirus (infectious bronchitis), Hepeviridae (Avian hepevirus, Turkey Viral Hepatitis), Herpesviridae (Mardivirus, Marek's, Gallid herpesvirus 1, Infectious Laryngotracheitis (ILT)), Influenza (H5N1), Paramyxoviridae (Avian pneumovirus (APV), PMV-1, PMV-2, PMV-3, PMV-6), Parvoviridae (chicken parvovirus (ChPV), goose parvovirus (Derzsy's)), Picornaviridae (Enterovirus, enterovirus-like particles, tremovirus), Poxviridae (foul pox, avipoxvirus), Reoviridae (viral arthritis, rotavirus), or Retroviridae (alpharetrovirus, Avian sarcoma leukosis virus (ASLV), Retrovirus (Type C)). Specific viral diseases in poultry are discussed above at Table 4. In a certain aspect, the present methods provide for the elimination of airborne viruses.

The present specification provides for and includes preventing the transmission of Influenza (orthomyxovirus A) by providing a poultry space having poultry with DHP at a level of at least 0.01 ppm. In an aspect, the Influenza virus is orthomyxovirus A serotype H5. In another aspect, the virus is orthomyxovirus A serotype H7. In an aspect, the poultry space is maintained at a DHP level of at least 0.1 ppm. In another aspect, the poultry space is maintained at a DHP level of at least 0.5 ppm. In yet other aspects, the transmission of influenza is prevented by providing DHP to a poultry space at between 0.01 ppm and 10.0 ppm. In a certain aspect, the DHP is provided to prevent initial infection.

Also included and provided for by the present specification is the treatment of a poultry flock infected with influenza virus comprising providing the flock after infection with a poultry space having at least 0.01 ppm DHP. In an aspect, the treatment can be in response to a bioterrorism attack. In another aspect, the treatment can be in response to an accidental infection of the flock with influenza or in response to the introduction of the virus from a wild bird. The present specification further provides for and includes providing a poultry flock infected with the influenza virus with a poultry space having at least 0.01 ppm DHP gas. In another aspect, a poultry flock infected with the influenza virus is provided a poultry space having at least 0.1 ppm DHP gas. In another aspect, a poultry flock infected with the influenza virus is provided a poultry space having at least 0.5 ppm DHP gas. In another aspect, a poultry flock infected with the influenza virus is provided a poultry space having at least 1.0 ppm DHP gas. In a certain aspect, the DHP gas level can be up to 50 ppm. In another aspect, the DHP gas level can be up to 10 ppm. In a certain aspect, the DHP level ranges between 0.01 and 10 ppm. In an aspect, the concentration of DHP gas provided to a flock after infection is at least 0.08 ppm. In yet another aspect, the concentration of DHP gas is at least 1.5 ppm. In an aspect, the concentration of DHP gas provided to a flock after infection is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to a flock after infection is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to a flock after infection is between 1.0 ppm and 8.0 ppm, or between 5.0 ppm and 10.0 ppm. In another aspect, the concentration of DHP during hatching incubation cycles between higher and lower concentrations of DHP.

As influenza is particularly devastating for a poultry flock, the present specification provides for a rapid response kit comprising one or more PHPG generating devices. Thus, a recently infected flock can be treated quickly to reduce the spread of the disease. Also provided for is the treatment of fomites, vehicles, and people that are exposed to an inflected flock to prevent the spread of the virus to other flocks.

The present specification provides for and includes treating a poultry flock infected with Influenza A serotype H5N1 comprising identifying a poultry flock infected with Influenza A serotype H5N1, providing an enclosed space housing the infected poultry flock with DHP at a level of at least 0.01 ppm. In an aspect, the level of DHP is at least 0.5 ppm. In another aspect, the level of DHP is between 0.1 ppm and 10 ppm.

Another poultry disease that causes significant losses is the pathogenic avian *Mycoplasma* spp. (*M. gallisepticum, M synoviae, M. meleagridis* and *M iowae*). The present specification provides for and includes methods for reducing the transmission of *Mycoplasma* spp. comprising placing poultry eggs into a poultry space, providing dry hydrogen peroxide (DHP) at a concentration of between 0.01 ppm and 10 ppm to said poultry space, maintaining said poultry eggs in said poultry space for a storage period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce the transmission of *Mycoplasma* spp. is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce the transmission of *Mycoplasma* spp. is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce the transmission of *Mycoplasma* spp. is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to reduce the transmission of *Mycoplasma* spp. is between 1.0 ppm and 8.0 ppm, or between 5.0 ppm and 10.0 ppm.

In another aspect, the present specification provides for and includes reducing the levels of *Mycoplasma* spp. in a poultry space prior to introducing live poultry (eggs or birds). It has been established that *Mycoplasma* can survive for extended periods in the environment including on human skin, clothing, fomites, and in the shavings that are often provided as litter in poultry facilities. See, Christensen et al., "Investigations into the survival of *Mycoplasma gallisepticum, Mycoplasma synoviae* and *Mycoplasma iowae* on materials found in the poultry house environment," *Avian Pathol.* 23(1):127-43 (1994). Thus, the application of DHP gas to facilities can be used to eliminate *Mycoplasma* from poultry spaces. As provided herein, the poultry space can be treated with DHP gas at between 0.01 ppm and 10 ppm for a period prior to the instruction of poultry. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce the levels of *Mycoplasma* spp. is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce the levels of *Mycoplasma* spp. is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce the levels of *Mycoplasma* spp. of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to reduce the levels of *Mycoplasma* spp. is between 1.0 ppm and 8.0 ppm, or between 5.0 ppm and 10.0 ppm. As provided herein, the space to be treated can be treated for at least 1 day prior to introducing live poultry. In another aspect, the poultry space is treated for at least 2 days prior to introducing live poultry. In yet another aspect, the poultry space is treated for at least 5 days prior to introducing live poultry. In another aspect, the poultry space is treated for at least 7 days prior to introducing live poultry. In some aspects, the poultry space is treated for 2 weeks prior to introducing live poultry. The amount of time necessary to reduce or eliminate *Mycoplasma* can be determined through empirical testing.

Fungi can cause losses to poultry and can be difficult to reduce or eradicate. The mold toxins are responsible for mycotoxicosis, so the removal or mitigation of the toxins is also important when improving the health of the poultry flock. Non-limiting examples of molds that cause disease in poultry are *Aspergillus fumigatus, Candida albicans, Dactylaria gallopava*, and *Trichophyton gallinae*. The present specification provides for and includes methods for reducing the transmission of Aspergillosis, Candidiasis, Moniliasis, dactylariosis or mycotoxicosis comprising placing poultry eggs into a poultry space, providing dry hydrogen peroxide (DHP) at a concentration of between 0.01 ppm and 10 ppm to said poultry space, maintaining said poultry eggs in said poultry space for a period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce the transmission of *Aspergillus fumigatus, Candida albicans, Dactylaria gallopava*, or *Trichophyton gallinae* is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce the transmission of *Aspergillus fumigatus, Candida albicans, Dactylaria gallopava*, or *Trichophyton gallinae* is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce the transmission of *Aspergillus fumigatus, Candida albicans, Dactylaria gallopava*, or *Trichophyton gallinae* is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to reduce the transmission of *Aspergillus fumigatus, Candida albicans, Dactylaria gallopava*, or *Trichophyton gallinae* is between 1.0 ppm and 8.0 ppm, or between 5.0 ppm and 10.0 ppm.

In another aspect, the present specification provides for and includes reducing the levels of *Aspergillus fumigatus, Candida albicans, Dactylaria gallopava*, or *Trichophyton gallinae* in a poultry space prior to introducing live poultry (eggs or birds). It has been established that fungi can survive for extended periods in various environments so a primary defense to transmission is the elimination of molds and spores from the environment prior to introducing live poultry. Thus, the application of DHP gas to facilities can be used to eliminate *Aspergillus fumigatus, Candida albicans, Dactylaria gallopava*, or *Trichophyton gallinae* from poultry spaces. As provided herein, the poultry space can be treated with DHP gas at between 0.01 ppm and 10 ppm for a period prior to the instruction of poultry. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce the levels of *Aspergillus fumigatus, Candida albicans, Dactylaria gallopava*, or *Trichophyton gallinae* is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce the levels of *Aspergillus fumigatus, Candida albicans, Dactylaria gallopava*, or *Trichophyton gallinae* is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce the levels of *Aspergillus fumigatus, Candida albicans, Dactylaria gallopava*, or *Trichophyton gallinae* is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to reduce the levels of *Aspergillus fumigatus, Candida albicans, Dactylaria gallopava*, or *Trichophyton gallinae* is between 1.0 ppm and 8.0 ppm, or between 5.0 ppm and 10.0 ppm. As provided herein, the space to be treated can be treated for at least 1 day prior to introducing live poultry. In another aspect, the poultry space is treated for at least 2 days prior to introducing live poultry. In yet another aspect, the poultry space is treated for at least 5 days prior to introducing live poultry. In another aspect, the poultry space is treated for at least 7 days prior to introducing live poultry. In some aspects, the poultry space is treated for 2 weeks prior to introducing live poultry. The amount of time necessary to reduce or eliminate *Aspergillus fumigatus, Candida albicans, Dactylaria gallopava*, or *Trichophyton gallinae* can be determined through empirical testing.

Among the parasites, coccidiosis caused by protozoa belonging to the phylum Apicomplexa is one of the more important diseases worldwide and responsible for considerable losses in production. Additional information is available on the internet at www.poultryhub.org/health/disease/types-of-disease/coccidiosis. Briefly, in chickens, coccidiosis is caused by seven species of the genus *Eimeria: E. acervulina, E. brunetti, E. maxima, E. mitis, E. necatrix, E. praecox* and *E. tenella*. Sporulated oocysts are ingested from contaminated litter and invade the intestinal wall of the intestinal tract where they undergo several cycles of replication. The resulting oocysts are shed in the faeces where, under appropriate conditions, the oocysts sporulate to complete the cycle. See McDougald, LR (2003) Protozoal Infections. In: Diseases of Poultry (ed. SaifYM), Iowa State Press, pp. 973-1026; Trees, AJ (2002) Parasitic Diseases. In: Poultry Diseases (eds Jordan, F; Pattison, M; Alexander, D; Faragher, T), W.B. Saunders, pp. 405-436.

There exists a need to treat the litter to prevent the infective cycle. Currently, there are no effective methods that are capable of eliminating *Eimeria* from poultry production, and control methods rely on farm management to minimize oocyst levels in the litter and chemical methods to provide prophylaxis. There are live attenuated vaccines available. U.S. Patent Publication No. 2004/0175391, published Sep. 9, 2004 (hereby incorporated by reference in its entirety), provides methods and compositions for the control of coccidiosis. There is a further need to provide for methods of treatment that are compatible with the presence of poultry and that are environmentally friendly (e.g., leave no residue).

The present specification provides for and includes methods to eliminate coccidiosis from a poultry facility comprising providing DHP at a concentration of at least 0.01 ppm and maintaining the DHP at 0.01 ppm for a week prior to the introduction of birds.

The application of DHP to the treatment or prevention of coccidiosis can further comprise treatments with one or more known coccidiosis treatments (acoccidiostat). As provided herein, DHP treatment of coccidiosis (or for other reasons) can be combined with a coccidiostat known in the art. Any useful anticoccidial agent can be used in the compositions and methods of the present disclosure. Coccidiostats (and the approved USDA level for poultry in parentheses) include amprolium (0.0125-0.025%); amprolium (0.0125%) with ethopabate (0.0004-0.004%); arsanilic acid or sodium arsanilate (0.04%); buquinolate (0.00825%), chlortetracycline (0.022%), clopidol or meticlorpindol (0.0125-0.025%); decoquinate (0.003%); dibutyltin dilaurate (butynorate (0.0375% for turkeys); dinitolmide (zoalene) (0.004-0.0125%); furzaolidone (0.0055-0.011%); lasalocid (0.0075-0.0125%); monensin (0.01-0.0121%); nicarbazin (0.0125%); nitrofurazone (0.0055%); nitromide (0.025% with sulfanitran (0.03%) and with roxarsone (0.005%); oxytetracycline (0.022%); robenidine (0.0033%); salinomycin (0.004-0.0066%); sulfadimethoxine (0.0125% with ormetoprim (0.0075%); sulfaquinoxaline (0.015%-0.025%). In "parts per million" (ppm), typical recommended inclusion rates for chick diets are: monensin: 100-120 ppm; salinomycin: 60 ppm; narasin: 70 ppm; and lasalocid: 90 ppm. In the case of salinomycin, a final concentration of between 44 and 66 ppm has been found to be efficacious (see Example 1). Preferred ionophore coccidiostats are salinomycin and lasalocid.

The present specification provides for, and includes, a method to reduce the transmission of *Histomonas* (histomoniasis) to poultry in a poultry production facility. *Histomonas melagridis* is a protozoan parasite of turkeys, and occasionally chickens, pheasants, and game birds, that acts together with facultative bacteria to produce the condition of Blackhead. Histomoniasis has high morbidity and mortality in turkeys. Chickens, while relatively resistant, are susceptible and significant disease has been seen in breeding chickens and free-range layers. Transmission of the parasite is through the ingestion of ova when birds eat Heterakis worms or as larvae in earthworms. Transmission also occurs through ingestion of faeces and there is an incubation period of 15-20 days. Outside of the host, the parasite is easily destroyed, thus providing an opportunity to reduce or largely eliminate the parasite from poultry spaces.

The present specification provides for, and includes, a method for reducing the transmission of *Histomonas* comprising placing poultry eggs into a poultry space, providing dry hydrogen peroxide (DHP) at a concentration of between 0.01 ppm and 10 ppm to said poultry space, maintaining said poultry eggs in said poultry space for a period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce the transmission of *Histomonas* is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce the transmission of *Histomonas* is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce the transmission of *Histomonas* is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to reduce the transmission of *Histomonas* is between 1.0 ppm and 8.0 ppm, or between 5.0 ppm and 10.0 ppm.

In another aspect, the present specification provides for and includes reducing the levels of *Histomonas* in a poultry space prior to introducing live poultry (eggs or birds). It has been established that fungi can survive for extended periods in various environments, so a primary defense to transmission is the elimination of molds and spores from the environment prior to introducing live poultry. Thus, the application of DHP gas to facilities can be used to eliminate *Histomonas* from poultry spaces. As provided herein, the poultry space can be treated with DHP gas at between 0.01 ppm and 10 ppm for a period prior to the instruction of poultry. As provided herein, the space to be treated can be treated for at least 1 day prior to introducing live poultry. In another aspect, the poultry space is treated for at least 2 days prior to introducing live poultry. In yet another aspect, the poultry space is treated for at least 5 days prior to introducing live poultry. In another aspect, the poultry space is treated for at least 7 days prior to introducing live poultry. In some aspects, the poultry space is treated for 2 weeks prior to introducing live poultry. The amount of time necessary to reduce or eliminate *Histomonas* can be determined through empirical testing.

The present specification provides for, and includes, methods and devices for treating poultry diseases that are caused by poultry parasites. In a certain aspect, the poultry parasite is a worm that causes helminthiasis in a poultry host. Helminthiasis can be caused by parasitic worms that have either a direct or an indirect life cycle. Parasites that have an indirect life cycle spend part of their lives in an intermediate host. Parasites that have direct life cycles are those that complete their life cycle without passage through an intermediate host (notably, some direct life cycle parasites can pass through multiple hosts). Non-limiting examples of parasitic worms capable of causing helminthiasis in poultry are provided in Table 4 along with non-limiting examples of intermediate hosts as appropriate to the life cycle.

In an aspect, the poultry disease is caused by a parasite that has an indirect life cycle. Intermediate hosts include insects and arthropods such as mosquitos, mites, lice, bedbugs, or flies. In a certain aspect, the intermediate hosts themselves are causative agents of poultry diseases. In another aspect, the poultry disease is caused by a parasite that has a direct life cycle. The present disclosure provides for and includes a method of treating a poultry space to kill the eggs, larva or hosts of a helminth comprising providing to the poultry space PHPG sufficient to maintain the PHPG at a level of at least 0.01 ppm. In an aspect, the level of PHPG provided to treat a helminth infestation is at least 0.5 ppm. In an aspect, the level of PHPG provided to treat a helminth infestation is at least 1.0 ppm. In aspects of the present specification, the level of PHPG provided to treat a poultry space to kill the eggs, larva or hosts of a helminth is less than 10.0 ppm.

TABLE 5

Common Helminths of Poultry

| Parasite | Host | Intermediate Host or Life Cycle | Organ infected | Pathogenicity |
|---|---|---|---|---|
| Nematodes (Roundworm) | | | | |
| *Amidostomum anseri* | Duck, goose, pigeon | Direct | Gizzard | Severe |
| *Ascaridia dissimilis* | Turkey | Direct | Small intestine | Moderate |
| *Ascaridia galli* | Chicken, turkey, duck, quail | Direct | Small imestine | Moderate |
| *Cyathostoma hamulosa* | Chicken, turkey, game birds | Grasshoppers, beetles | Gizzard | Moderate |
| *Cyathostoma bronchialis* | Turkey, duck | Direct or earthworm | Trachea | Severe |
| *Cvrnea colini* | Turkey, game birds | Cockroaches | Proventriculus | Mild |
| *Dispharynx nasuta* | Chicken, turkey, game birds, pigeon | Sowbugs | Proventriculus | Moderate to severe |
| *Gongylonema inglyvicola* | Chicken, game birds | Beetles, cockroaches | Crop, esophar "lis, proventriculus | Mild |
| *Heterakis gallinarwn* | Chicken, turkey, duck, game birds | Direct | Ceca | Mild, but transmits agent of histomoniasis |
| *Heterakis isolonche* | Quail duck pheasant | Direct | Ceca | |
| *Onlithostrongylus quadriradiatus* | Pigeon, dove | Direct | Small intestine | |
| *Oxyspirura mansoni* | Chicken, turkey, guinea fowl, quail | Cockroaches | Eye | Moderate |
| *Stronglyoides avium* | Chicken, turkey, quail, goose | Direct | Ceca | Moderate |
| *Subulura brumpti* | Chicken, turkey, duck, game birds | Earwigs, grasshoppers, beetles, cockroaches | Ceca | Mild |
| *Syngamus trachea* | Chicken, turkey, pheasant, quail | None or earthworm | Trachea | Severe |
| *Tetrameres americana* | Chicken, turkey, duck, game birds, pigeon | Grasshoppers, cockroaches | Proventriculus | Moderate to severe |
| *Trichosrrong*: 1, *fus tenuis* | Chicken, turkey, duck, game birds, pigeon | Direct | Ceca | |
| Cestodes (Tapeworms) | | | | |
| *Chowwtaenia ilfundibulwn* | Chicken | House files | Upper intestine | Moderate |
| *DaFainea* | Chicken | Slugs, snails | Duodenum | Severe |
| *Aletmliasthes* | Turkey | Grasshoppers | Intestine | Unknown |
| *Raillietina cestici!lus* | Chicken | Beetles | Duodenum, jejunum | Mild |
| *Raillietina echinobothrida* | Chicken | Ants | Lower intestine | Severe, nodules |
| *Raillietina* | Chicken | Ants | Lower intestine | Severe |
| Nematomorpha (Hairworm) | | | | |
| *Capillaria caudinflata* | Chicken, turkey, duck, game birds, pigeon | Earthworms | Small intestine | Moderate to severe |

TABLE 5-continued

Common Helminths of Poultry

| Parasite | Host | Intermediate Host or Life Cycle | Organ infected | Pathogenicity |
| --- | --- | --- | --- | --- |
| *Capillaria contorta* | Chicken, turkey, duck, | None or earthworms | Mouth, esophagus, crop | Severe |
| *Capillaria obsignata* | Chicken, turkey, goose, pigeon, quail | Direct | Small intestine, ceca | Severe |

Another poultry disease that causes significant losses is the flatworm *Prosthogonimus*, also called the oviduct fluke. *Prosthogonimus* is a genus of flatworm parasites belonging to the trematodes that infect birds. The primary concern for poultry production is *Prosthogonimus macrorchis* though *Prosthogonimus anatinus*, *Prosthogonimus ovatus*, and *Prosthogonimus pellucidus* are also of veterinary concern and can be treated or controlled using the methods of the present specification. The present specification provides for and includes methods for reducing the transmission of *Prosthogonimus* comprising placing poultry eggs into a poultry space, providing dry hydrogen peroxide (DHP) at a concentration of between 0.01 ppm and 10 ppm to said poultry space, maintaining said poultry eggs in said poultry space for a period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce the transmission of *Prosthogonimus* is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce the transmission of *Prosthogonimus* is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce the transmission of *Prosthogonimus* is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided to reduce the transmission of *Prosthogonimus* is between 1.0 ppm and 8.0 ppm, or between 5.0 ppm and 10.0 ppm.

Also provided for and included in the present specification is the prevention and treatment of poultry of tapeworm infestations. Tapeworms are an example of a parasite having an indirect life cycle. Adult tapeworms live in the bowel of the bird and pass packets of eggs in the droppings that need to be eaten by an insect to become infective. The eggs hatch in the insect and are transmitted when the birds eat the insects carrying the tapeworm larvae. Thus, DHP containing spaces provide for the prevention and reduction of tapeworms by blocking the transmission of the eggs to the intermediate host and from the intermediate host to the bird.

It is believed that adult tapeworms, existing in the poultry bowel, will not be affected by the presence of DHP. Not to be limited by theory, it is thought that the tapeworm eggs present in the droppings will be killed by DHP. This will break the necessary transmission of the eggs to the insect host. Also not being limited by theory, it is thought that the insect hosts are susceptible to DHP. As provided by International Patent Publication No. WO 2014/186805, PHPG is effective at killing many arthropods and is also a very strong repellant. Thus, in addition to its arthrocidal activity, DHP will repel insect intermediates and thereby prevent or reduce the transmission of tapeworm larva to the poultry. Thus, complete eradication of tapeworms from a poultry space would include treatment of the poultry with one or more drugs to eradicate the adult parasite and DHP treatment to eradicate the eggs and intermediate hosts. In an aspect, the tapeworm treatment includes treating the poultry with praziquantel. Thus, the present methods provide for and include combined methods for the eradication of tapeworms from a poultry population.

The present specification provides for and includes methods and devices for treating tapeworms, an indirect lifecycle parasite. In an aspect, the methods of the present specification provide for breaking the transmission cycle. For example, the application of DHP to a poultry space provides for the reduction of arthropod hosts and carriers including, for example, ants, beetles, copod crustaceans, freshwater crustaceans, earthworms, grasshoppers, houseflies, leeches, slugs, snails, and stable flies. In a certain aspect, the DHP in a poultry space kills the arthropod vectors of a parasitic disease. In another aspect, the DHP drives the arthropod vectors of a parasitic disease from the poultry space, thus breaking the cycle of transmission between the poultry and non-poultry hosts.

The present specification provides for and includes methods for treating poultry diseases that further include incorporation of one or more traditional control methods. In an aspect, the methods can include treatments of roundworms using chemical agents. In an aspect, the chemical agents useful in the present methods include piperazine, hygromycin B, coumaphos, thiabendazole, and combinations thereof. In an aspect, the chemical agents are provided by means and at levels known in the art, including for example, by providing the agent in drinking water, injection, spraying, mixing with food, etc.

The present specification provides for and includes methods for improving poultry health and reducing disease comprising controlling insects. Suitable methods have been described in International Patent Application No. PCT/US2014/038652, published as International Patent Publication No. WO 2014/186805. The present specification provides for and includes eliminating flying insects from a poultry site and thereby reducing disease transmission. Importantly, as insects are often carriers of disease, the elimination of flying insects from the wild can prevent the introduction of diseases onto clean facilities. Among the unexpected findings discussed below in Example 3, it is observed flying insects were virtually eliminated from the facility. This occurred within the first couple days of applying DHP to the poultry space. Thus the application of DHP to the hatchery had the unexpected benefit of reducing the flying vectors of disease.

The present specification provides for and includes methods for improving growth and development in chickens by eliminating mites and lice. Mites can cause significant mortality and reduced productivity. Mites can also make the poultry susceptible to other parasites and diseases. See Strother, "Poultry pest management," Publ. No. ARN-483. Alabama Cooperative Extension System. Auburn University (2008). Birds with heavy infestations of mites can have greatly reduced productivity. See DeLoach et al., "Northern fowl mite, Ornithonyssus sylviarum, (Acari: Macronyssidae) ingests large amounts of blood from White Leghorn hens," *J Med. Entomol.* 18:374-377 (1981). Accordingly, there is a great need for methods to treat poultry and poultry spaces for mite infestations, particularly in the presence of the birds.

The present specification provides for the treatment of poultry and poultry spaces to reduce or eliminate mites and lice comprising providing dry hydrogen peroxide (DHP) at a concentration of between 0.01 ppm and 10 ppm to a poultry space, and maintaining the poultry space eggs in said poultry space for a storage period. In an aspect, the present specification provides for the reduction or elimination of mites selected from the group consisting of the northern fowl mite (*Ornithonyssus* sylviarum), the red poultry mite (*Dermanyssus gallinae*), and the tropical fowl mite (*Ornithonyssus* bursa). In an aspect, the present specification provides for the reduction or elimination of lice selected from the group consisting of the *Menocanthus stramineus, Menopon gallinea,* and *Holomenopen* spp. Importantly, mites are difficult to detect and eradicate because they often remain hidden. In the present methods however, DHP penetrates all spaces and thus is an effective treatment, yet is safe for the poultry and the workers. Thus, existing mite infestations can be treated and future infestations can be prevented as mites introduced will be killed.

The present specification provides for and includes methods for reducing mite or lice infestations of poultry and poultry spaces comprising placing poultry eggs into a poultry space, providing dry hydrogen peroxide (DHP) at a concentration of between 0.01 ppm and 10 ppm to said poultry space, maintaining said poultry eggs in said poultry space for a period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce mite or lice infestations of poultry and poultry spaces of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce mite or lice infestations of poultry and poultry spaces of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce mite or lice infestations of poultry and poultry spaces of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided mite or lice infestations of poultry and poultry spaces of the present disclosure is between 1.0 ppm and 8.0 ppm, or between 5.0 ppm and 10.0 ppm.

In another aspect, the present specification provides for and includes reducing the levels of mites or lice in a poultry space prior to introducing live poultry (eggs or birds). It has been established that fungi can survive for extended periods in various environments, so a primary defense to transmission is the elimination of molds and spores from the environment prior to introducing live poultry. Thus, the application of DHP gas to facilities can be used to eliminate mites or lice from poultry spaces. As provided herein, the poultry space can be treated with DHP gas at between 0.01 ppm and 10 ppm for a period prior to the introduction of poultry. As provided herein, the space to be treated can be treated for at least 1 day prior to introducing live poultry. In another aspect, the poultry space is treated for at least 2 days prior to introducing live poultry. In yet another aspect, the poultry space is treated for at least 5 days prior to introducing live poultry. In another aspect, the poultry space is treated for at least 7 days prior to introducing live poultry. In some aspects, the poultry space is treated for 2 weeks prior to introducing live poultry. The amount of time necessary to reduce or eliminate mites or lice can be determined through empirical testing.

A common insect found in poultry facilities is the Darkling Beetle (*Alphitobius diaperinus*). Darkling beetles have been a problem in the poultry industry for many years, spreading disease, damaging buildings, and consuming feed. In addition, growing chicks eat the beetles and larva which they are unable to digest, thus reducing the intake of feed during grow-out. In short, darkling beetles are a serious problem that reduces productivity and profits. Application of DHP to poultry spaces causes darkling beetles to migrate out of the chicken house or causes them to burrow into the litter covering the chicken house floor to avoid it. This means that the beetles are less likely to emerge into places where the chicks can eat them and are less likely to thrive, resulting in a decreasing population of beetles over time. By reducing the beetle population, the chicks don't eat them, leaving room in their crops for more feed. Thus, the elimination of darkling beetles will increase the efficiency of the grow-out process.

The present specification provides for and includes methods for reducing darkling beetle infestations of poultry and poultry spaces comprising placing poultry eggs into a poultry space, providing dry hydrogen peroxide (DHP) at a concentration of between 0.01 ppm and 10 ppm to said poultry space, maintaining said poultry eggs in said poultry space for a period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided to reduce darkling beetle infestations of poultry and poultry spaces of the present disclosure is at least 0.08 ppm. In another aspect, the concentration of DHP gas is at least 1.0 ppm. In yet another aspect, the concentration of DHP gas is at least 1.5 ppm. In an aspect, the concentration of DHP gas provided to reduce darkling beetle infestations of poultry and poultry spaces of the present disclosure is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided to reduce darkling beetle infestations of poultry and poultry spaces of the present disclosure is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided darkling beetle infestations of poultry and poultry spaces of the present disclosure is between 1.0 ppm and 8.0 ppm, or between 5.0 ppm and 10.0 ppm.

As used herein, the singular forms "a," "an," and "the" include plural references unless the context clearly dictates otherwise. For example, the term "a bacterium" or "at least one bacterium" may include a plurality of bacteria, including mixtures thereof. In another example, the term "a fungi" or "at least one fungi" may include a plurality of bacteria, including mixtures thereof. Similarly, "a VOC" or "at least one VOC" may include multiple VOCs and mixtures thereof.

As used herein, the term "about" refers to ±10%.

The terms "comprises," "comprising," "includes," "including," "having," and their conjugates, mean "including but not limited to."

The term "consisting of" means "including and limited to."

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein the term "higher" refers to at least about 3%, 5%, 7%, 10%, 15%, 20%, 25%, 30%, 50%, 60%, 70%, 80%, 90%, or even a few folds higher.

As used herein, the terms "improving" and "increasing" refer to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater increase.

As used herein, the term "less" refers to at least about 3%, 5%, 7%, 10%, 15%, 20%, 25%, 30%, 50%, 60%, 70%, 80%, 90%, or even a few folds lower.

As used herein, the terms "reducing" and "decreasing" refer to at least about 2%, at least about 3%, at least about 4%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or greater decrease.

Throughout this application, various embodiments of this disclosure may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number "and" a second indicate number and "ranging/ranges from" a first indicate number "to" a second indicate number are used herein interchangeably and are meant to include the first and second indicated numbers and all the fractional and integral numerals therebetween.

As used herein, the term "method" refers to manners, means, techniques and procedures for accomplishing a given task including, but not limited to, those manners, means, techniques, and procedures either known to, or readily developed from, known manners, means, techniques, and procedures by practitioners of the chemical, pharmacological, biological, biochemical, and medical arts.

The present specification provides for, and includes, methods for reducing transmission of diseases in a poultry production facility by targeting the rooms, equipment, and personnel with DHP to reduce levels of bacterial and viral pathogens. Of particular importance for the infection and reinfection of poultry are fomites. Fomites are nonliving objects or substances capable of carrying infectious organisms, such as germs or parasites, and hence transferring them from one individual to another or from one space to another. Fomites include farm machinery and equipment, storage boxes, shipping containers, coops and tools (shovels, wheelbarrows, brooms, mops, etc.). Fomites also include clothing and personal protection equipment (PPE) used by employees. By treating fomites with DHP, the cycle of infection can be broken, or the probability of transmission can be reduced.

By providing spaces and equipment with DHP at a level of between 0.01 ppm and 10 ppm to an enclosed space at a poultry production facility, the levels of pathogens are reduced and thus the probability of transmission is reduced. In an aspect, a facility can target specific areas for treatment that are identified as sources of cross-contamination. In an aspect, locker rooms and storage rooms can be treated, thereby enhancing existing isolation and transmission prevention procedures. In an aspect, treating locker rooms includes treating the clothing of the employees to reduce transmission.

In an aspect, the method includes treating equipment at a poultry production facility comprising supplying the storage space for equipment with an amount of DHP to maintain the space at a concentration of at least 0.01 ppm. In an aspect the farm machinery is stored in a barn provided with DHP at a level of between 0.01 ppm and 10 ppm. Such treatment will eliminate or reduce pathogens, and disease causing organisms on equipment that comes into routine contact with poultry containing areas of a poultry production facility. Also included and provided for are methods to reduce the transmission of poultry disease by treating support spaces at a production facility by providing DHP to maintain the space at a concentration of at least 0.01 ppm. Suitable support spaces include locker rooms and changing facilities for staff, and break or lunch areas available for staff. Other support spaces suitable for the methods of the present specification include closets and storage areas, as well as any adjacent or attached office spaces. By eliminating or reducing possible sources of pathogens, the flocks can be maintained disease free.

The present specification provides for and includes methods to prevent the transmission of pests, pathogens, and disease by treating poultry spaces with DHP in between occupation by poultry. For example, in the broiler production cycle, the grow-out house's production includes a "flock cycle gap" in which the facility is cleaned and prepped after the broilers are collected and shipped for processing. Such preparation can include chemical cleaning and disinfection, and changing of the litter, among other tasks, and typically removes the grow-out house from production for a period of 6 to 9 days. This period provides an opportunity to treat the poultry spaces to reduce or eliminate pathogens. As the need for air circulation and environmental conditioning are significantly reduced, the effectiveness of DHP on the facility is increased. Even further, without the birds, the levels of VOCs and ammonia are reduced as well, thereby increasing the availability of DHP to inactivate viruses, bacteria, fungi, insects, and toxins. Importantly, as DHP gas can freely diffuse, is non-toxic and leaves no residue, the application of DHP during the flock cycle gap will be superior to other methods. Other poultry spaces have similar gaps in occupation by eggs or birds that provide a cycle gap suitable for application of pathogen remediation methods of the present specification.

In an aspect, a method for preventing the transmission of pests, pathogens, and disease comprises providing DHP gas to a poultry space for at least 1 day of a cycle gap at a concentration of at least 0.01 ppm. In an aspect, the method includes providing DHP gas at a concentration of at least 0.01 ppm for at least 2 days of a cycle gap. In another aspect, the method includes providing DHP gas at a concentration of at least 0.01 ppm for at least 3 days of a cycle gap. In another aspect, the method includes providing DHP gas at a concentration of at least 0.01 ppm for at least 4 days of a cycle gap. In another aspect, the method includes providing DHP gas at a concentration of at least 0.01 ppm for at least 5 days of a cycle gap. In another aspect, the method includes providing DHP gas at a concentration of at least 0.01 ppm for at least 6 days of a cycle gap. In another aspect, the method includes providing DHP gas at a concentration of at least 0.01 ppm for at least 7 days of a cycle gap. In another aspect, the method includes providing DHP gas at a concentration of at least 0.10 ppm for at least 2 days of a cycle gap. In another aspect, the method includes providing DHP gas at a concentration of at least 0.10 ppm for at least 3 days of a cycle gap. In another aspect, the method includes providing DHP gas at a concentration of at least 0.10 ppm for at least 4 days of a cycle gap. In another aspect, the method includes providing DHP gas at a concentration of at least 0.10 ppm for at least 5 days of a cycle gap. In another aspect, the method includes providing DHP gas at a concentration of at least 0.10 ppm for at least 6 days of a cycle gap. In another aspect, the method includes providing DHP gas at a concentration of at least 0.10 ppm for at least 7 days of a cycle gap. In an aspect, the method includes providing DHP gas at a concentration of at least 0.5 ppm for at least 2 days of a cycle gap. In another aspect, the method includes providing DHP gas at a concentration of at least 0.5 ppm for at least 3 days of a cycle gap. In another aspect, the method includes providing DHP gas at a concentration of at least 0.5 ppm for at least 4 days of a cycle gap. In another aspect, the method includes providing DHP gas at a concentration of at least 0.5 ppm for at least 5 days of a cycle gap. In another aspect, the method includes providing DHP gas at a concentration of at least 0.5 ppm for at least 6 days of a cycle gap. In another aspect, the method includes providing DHP gas at a concentration of at least 0.5 ppm for at least 7 days of a cycle gap.

The present specification provides for and includes a method for preventing the transmission of pests, pathogens, and disease comprises providing DHP gas to a poultry space during a cycle gap at a concentration of between 0.01 ppm and 10 ppm to said poultry space, and maintaining said poultry eggs in said poultry space for a period. In a certain aspect, the DHP gas level can be up to 50 ppm. In another aspect, the DHP gas level can be up to 10 ppm. In a certain aspect, the DHP level ranges between 0.01 ppm and 10 ppm. In an aspect, the concentration of DHP gas provided for preventing the transmission of pests, pathogens, and disease is at least 0.08 ppm. In another aspect, the concentration of DHP gas is at least 1.0 ppm. In yet another aspect, the concentration of DHP gas is at least 1.5 ppm. In an aspect, the concentration of DHP gas provided for preventing the transmission of pests, pathogens, and disease is at least 2.0 ppm. In another aspect, the concentration of DHP gas is at least 3.0 ppm. In an aspect, the concentration of DHP gas is at least 4.0 ppm. In an aspect, the concentration of DHP gas is at least 5.0 ppm. In another aspect, the concentration of DHP gas provided for preventing the transmission of pests, pathogens, and disease is at least 6.0 ppm. In an aspect, the concentration of DHP gas is less than 10 ppm. In an aspect, the concentration of DHP gas is less than 9.0 ppm. In another aspect, the concentration of DHP gas is less than 8.0 ppm. In an aspect, the concentration of DHP gas is less than 7.0 ppm. In another aspect, the concentration of DHP gas is between 0.01 ppm and 10.0 ppm. In yet another aspect, the concentration of DHP gas is between 0.01 ppm and 5.0 ppm. In an aspect, the concentration of DHP gas is between 0.08 ppm and 2.0 ppm. In yet another aspect, the concentration of DHP gas is between 1.0 ppm and 3.0 ppm. In an aspect, the concentration of DHP gas provided for preventing the transmission of pests, pathogens, and disease is between 1.0 ppm and 8.0 ppm, or between 5.0 ppm and 10.0 ppm. The period of providing DHP to a poultry space during a cycle gap can be 1 to 9 days. In an aspect, the period is 1 day. In another aspect, the period is 2 days. In another aspect, the period is 3 days. In yet another aspect, the period is 4 days. In some aspects, the period is 5 days. The present specification provides for and includes providing DHP during a cycle gap of 6 days or more.

The present specification provides for and includes methods for treating a poultry facility that has an emergent disease. As used herein, an "emergent disease" is a disease, infection, or pathogen infestation that newly appears at an existing facility. Examples of diseases and pathogens that can be emergent diseases are presented in Table 3. In a certain aspect, the emergent disease is a virus selected from the group consisting of influenza, infectious laryngotracheitis (ILT), Newcastle disease, infectious bronchitis (coronavirus), infectious bursal disease (Bimaviridae), haemorrhagic enteritis (adenovirus), and avian encephalomyelitis (Picornaviridae). Other emergent diseases can be bacterial, including but not limited to, bacterial diseases selected from the group consisting of colibacillosis, fowl cholera, coryza, turkey coryza (Bordetellosis), Pullorum disease, mycoplasmosis, pasteurellosis (ducks), and necrotic enteritis. Parasites, insects, and fungal pathogens can also be emergent diseases. Particularly well suited to a method of treating an emergent disease are diseases that are airborne.

Outbreaks of infectious diseases on poultry farms are particularly devastating. In the United States, avian flu results in the culling of 48 million chickens and turkeys from late 2014 through mid-2015. A recent outbreak of avian flu in Iran, led to the culling of 17 million birds. In the Philippines, 400,000 birds were culled at the first report of an avian flu outbreak. As determined by the U.S. Department of Agriculture, there are multiple routes to the spread of avian flu including direct and indirect contacts between disease sites including movement of trucks, feed, people, and equipment (see USDA Epidemiologic and Other Analyses of HPAI-Affected Poultry Flocks: Jun. 15, 2015 Report). Thus, the availability of kits comprising DHP gas generating devices can significantly reduce losses due to culling and reduce the spread of infection.

The present specification provides for and includes methods for treating a poultry facility that has an emergent disease by providing a rapid response to the outbreak by providing DHP at high levels as quickly as possible. Thus, the present specification provides for kits or rapid response teams that include an excess of DHP generating devices. Thus, a team can enter a facility and set up multiple DHP generating devices to quickly build up DHP to a concentration of 0.2 ppm or higher. In an aspect, the DHP provided for the treatment of an emergent disease is 0.5 ppm or higher. In an aspect, the DHP producing capacity provided to a facility in need of treatment of an emergent disease is at least twice the level needed to maintain the desired DHP level. In an aspect, the DHP producing capacity provided to a facility in need of treatment of an emergent disease is at least 3 times the level needed to maintain the desired DHP level.

The present specification provides for and includes methods for treating a region surrounding a poultry facility that has an emergent disease comprising providing one or more DHP generating devices to other poultry facilities that are within 1 kilometer of a poultry facility having an emergent disease to provide a DHP concentration in the other poultry facility of at least 0.01 ppm. In an aspect, the method includes providing one or more DHP generating devices to other poultry facilities that are within 2 kilometers of a poultry facility having an emergent disease. In an aspect, the method includes providing one or more DHP generating devices to other poultry facilities that are within 3 kilometers of a poultry facility having an emergent disease. In an aspect, the method includes providing one or more DHP generating devices to other poultry facilities that are within 4 kilometers of a poultry facility having an emergent disease. In an aspect, the method includes providing one or more DHP generating devices to other poultry facilities that are within 5 kilometers of a poultry facility having an emergent disease. In an aspect, the method includes providing one or more DHP generating devices to other poultry facilities that are within 7.5 kilometers of a poultry facility having an emergent disease. In an aspect, the method includes providing one or more DHP generating devices to other poultry facilities that are within 10 kilometers of a poultry facility having an emergent disease.

The present specification provides for and includes methods for treating a region surrounding a poultry facility that has an emergent disease and is under a culling order by a government comprising providing one or more DHP generating devices to other poultry facilities that are within 1 kilometer of a poultry facility having an emergent disease to provide a DHP concentration in the other poultry facility of at least 0.01 ppm. In an aspect, the method includes providing one or more DHP generating devices to other poultry facilities that are within 2 kilometers of a poultry facility having an emergent disease. In an aspect, the method includes providing one or more DHP generating devices to other poultry facilities that are within 3 kilometers of a poultry facility having an emergent disease. In an aspect, the method includes providing one or more DHP generating devices to other poultry facilities that are within 4 kilometers of a poultry facility having an emergent disease. In an aspect, the method includes providing one or more DHP generating devices to other poultry facilities that are within 5 kilometers of a poultry facility having an emergent disease. In an aspect, the method includes providing one or more DHP generating devices to other poultry facilities that are within 7.5 kilometers of a poultry facility having an emergent disease. In an aspect, the method includes providing one or more DHP generating devices to other poultry facilities that are within 10 kilometers of a poultry facility having an emergent disease.

Figure 15:
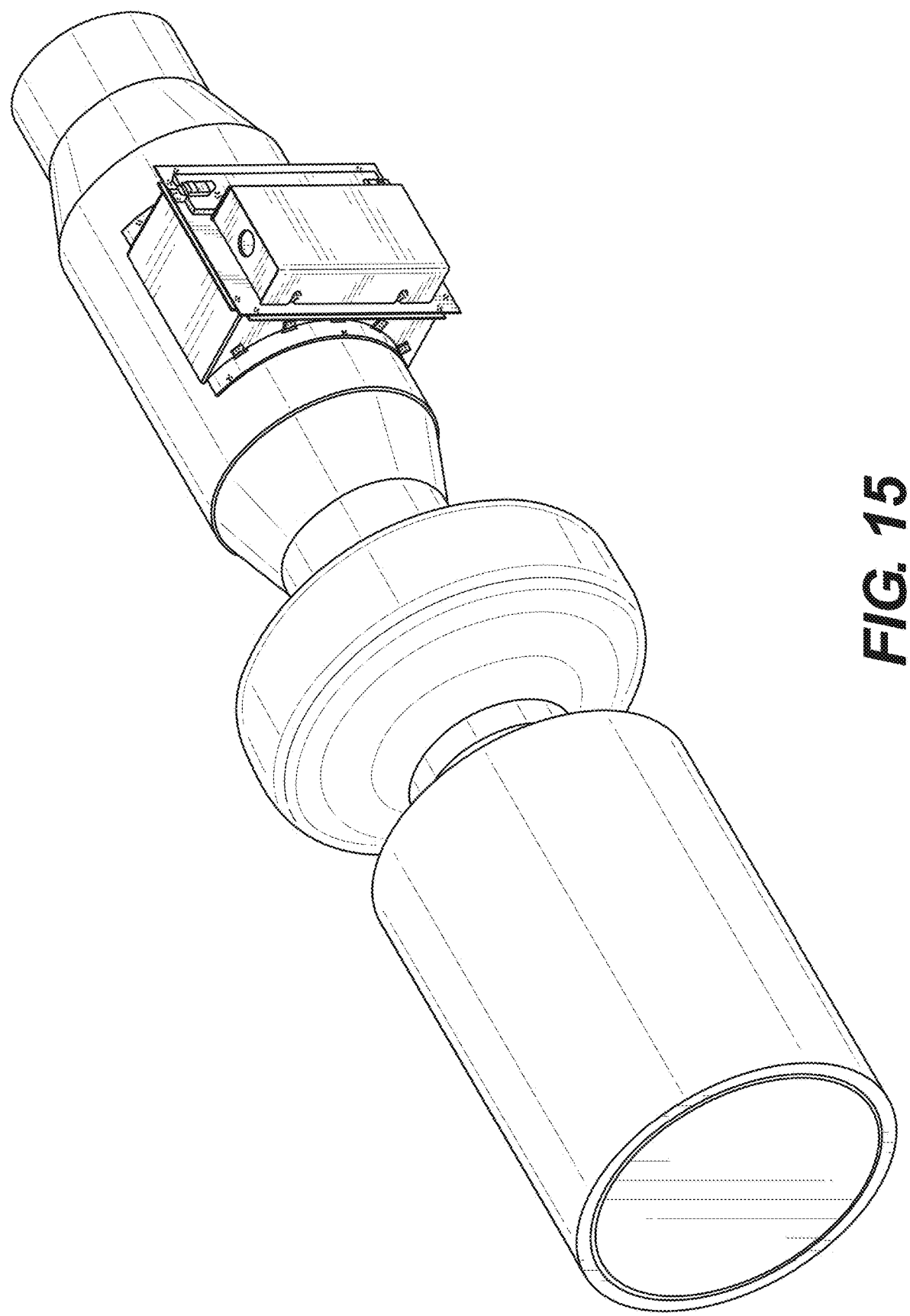
FIG. 15 presents a view of an embodiment for a stand-alone DHP gas generating device.
Figure 16:
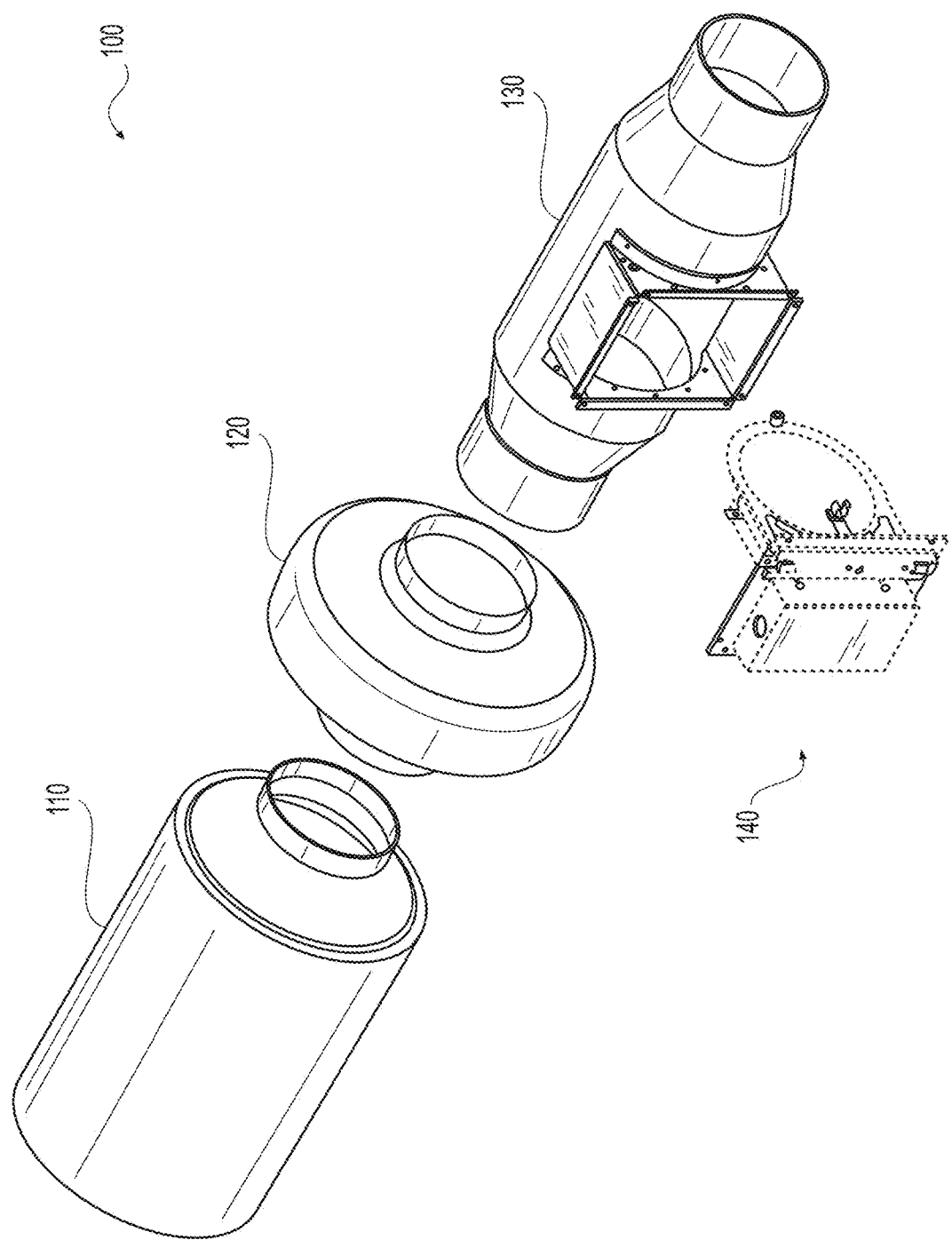
FIG. 16 presents an exploded view of an embodiment of a stand-alone DHP gas generating device having a filter 110, a fan unit 120, an adaptor 130, and a DPH gas generating assembly 140.
Figure 18:
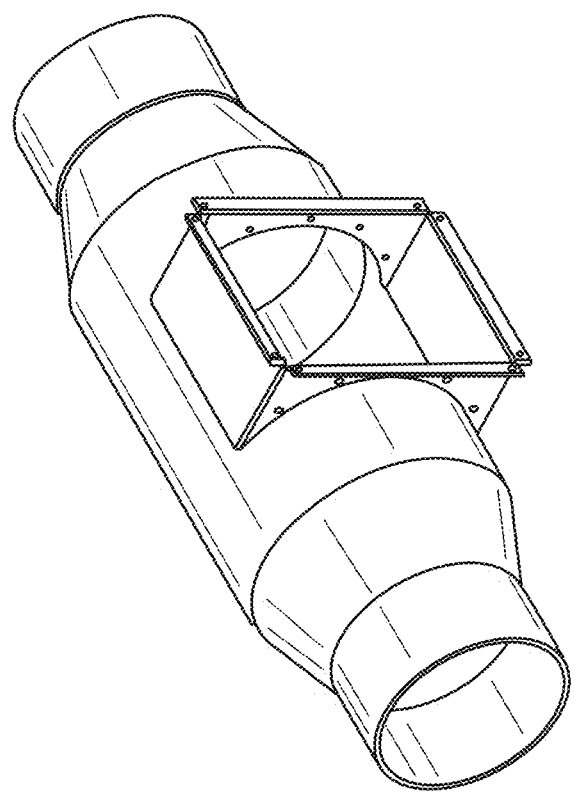
FIG. 18 presents a view of an adapter duct assembly according to an embodiment of the present disclosure.
Figure 17:
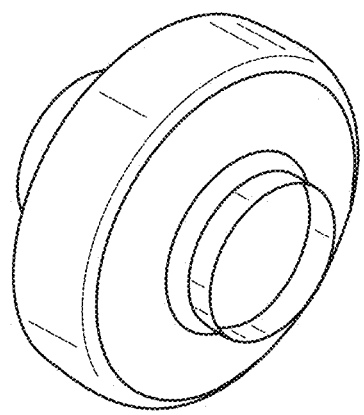
FIG. 17 presents a view of a fan unit according to an embodiment of the present disclosure.
Figure 19A:
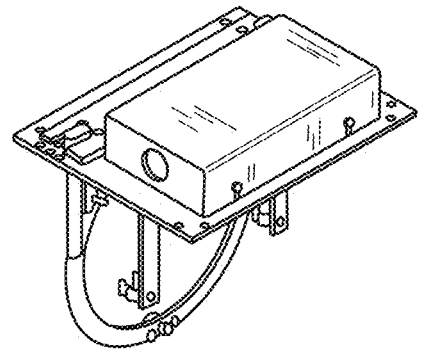
FIGS. 19A-D present views of a DHP gas generating assembly according to an embodiment of the present disclosure.
Figure 19B:
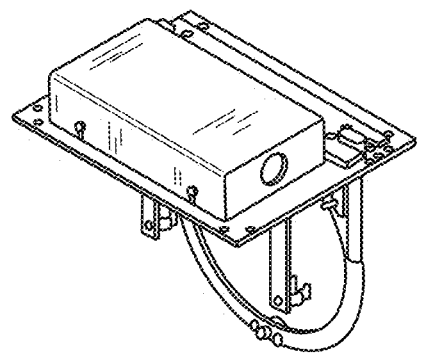
Figure 19C:
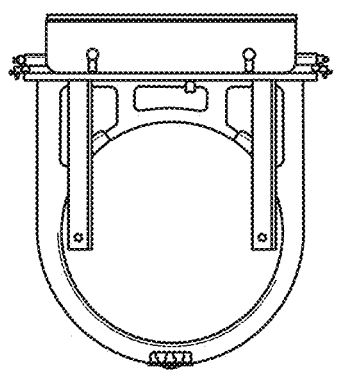
Figure 19D:
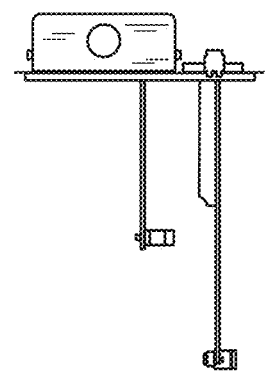

Exemplary portable generating devices for a rapid response kit include, but are no limited to, the stand alone devices shown in FIGS. 10 and 15. As provided herein, a kit for rapid response includes a sufficient number of DHP gas generating devices to quickly raise the level of DHP gas to a concentration of at least 0.01 ppm. In another aspect, the kit provides sufficient DHP gas generating devices to maintain a space at a concentration of at least 0.10 ppm. In another aspect, the kit provides a sufficient number DHP gas generating devices to maintain a space at a concentration of at least 0.5 ppm. In a certain aspect, the kit provides a sufficient number DHP gas generating devices to maintain a space at a concentration of at least 1.0 ppm. For small facilities, a single device is sufficient for rapid response kits of the present specification. For larger facilities, particularly for multi-room facilities and integrated farms such as a primary breeding facility, a breeder farm, or a hatchery, ten or more devices can be stored for use in a rapid response kit for infectious disease. As provided herein, upon identification of an outbreak of disease on a farm, at least one kit is provided to the infected farm and other kits are dispatched to adjacent and nearby farms to prevent and contain the spread. Accordingly, the availability of kits is important for the reduction of infectious disease outbreaks so that trucks, feed, people, and equipment moving between poultry production facilities can be treated together in surrounding farms.

The present specification provides for and includes producing poultry that have improved health. In an aspect, the health is improved due to reduced loads of infective agents. In a further aspect, the present methods improve the health of treated poultry by increasing the function of the bursa during development. The present methods provide for and include decreasing the amount of the disease organism in the environment, decreasing the disease organism load on a flock, decreasing the disease organism load on an individual bird, and combinations of each.

Figure 2:
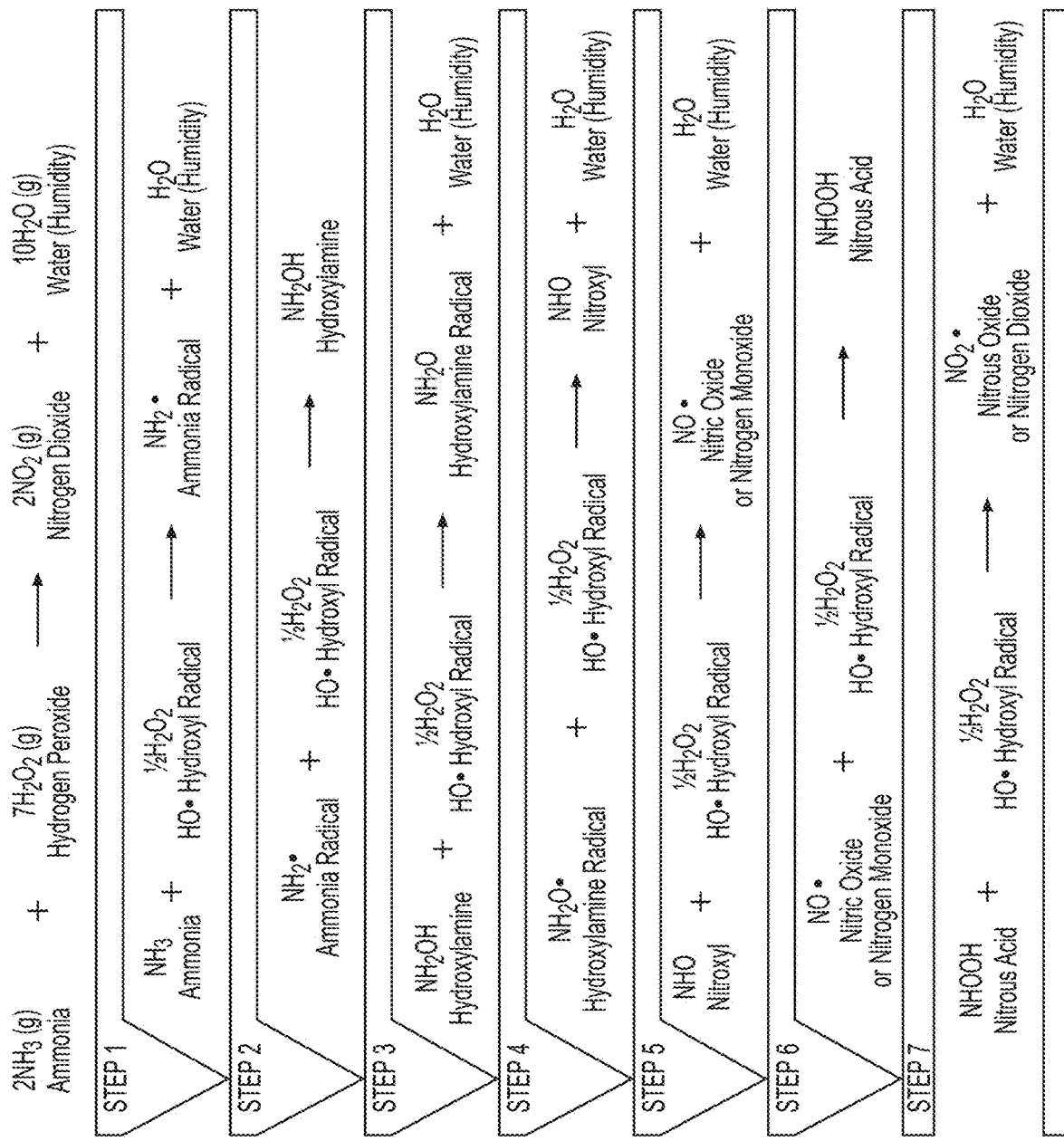
FIG. 2 is a diagram presenting the breakdown of ammonia through reaction with $H_2O_2$
Figure 3:
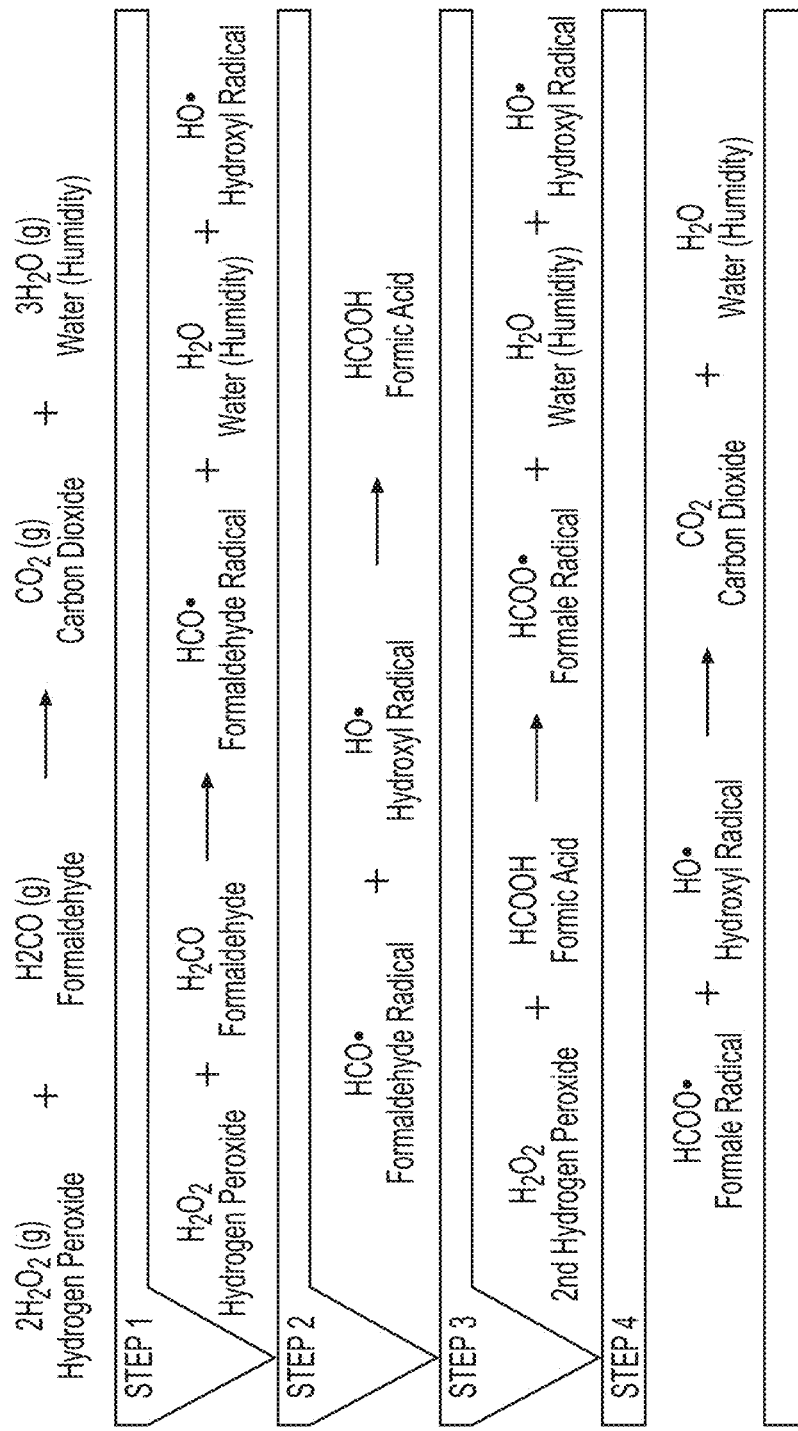
FIG. 3 is a diagram presenting the breakdown of formaldehyde through reaction

The present specification provides for and includes reducing the odors associated with poultry production. Gasses such as ammonia and volatile organic compounds (VOCs) can build up in the farms and be a nuisance to neighbors, a health hazard to employees, and a hazard to the health of the poultry themselves. Among the benefits of DHP, DHP can break down ammonia and VOCs. As show in FIG. 2, ammonia is broken down by $H_2O_2$ to produce nitrogen dioxide ($NO_2$). The seven step reaction is rapid and proceeds without a build-up of intermediate species.

Figure 4:
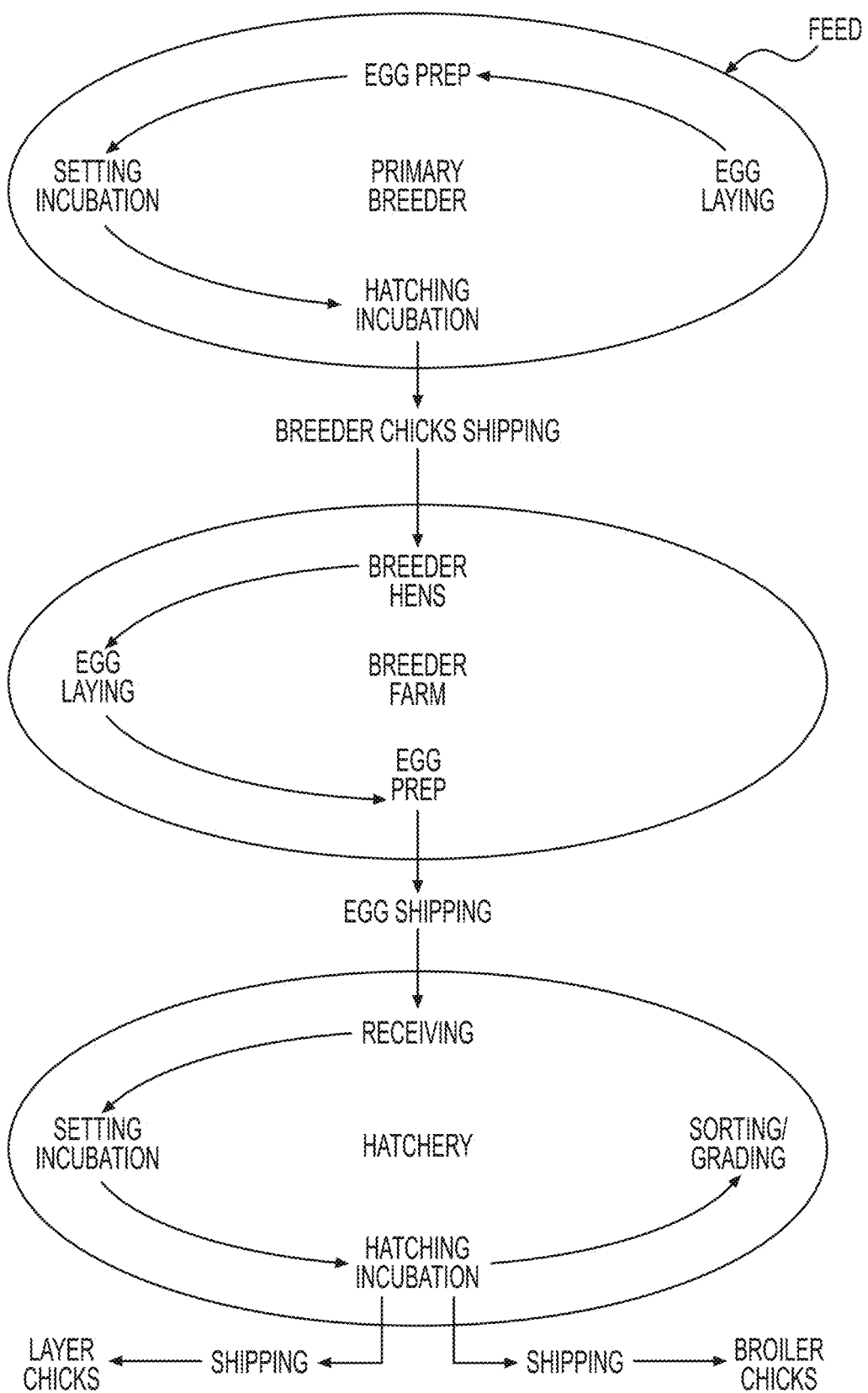
FIG. 4 is a diagram presenting non-limiting examples of steps of the poultry production process that benefit from the application of DHP technology
Figure 5:
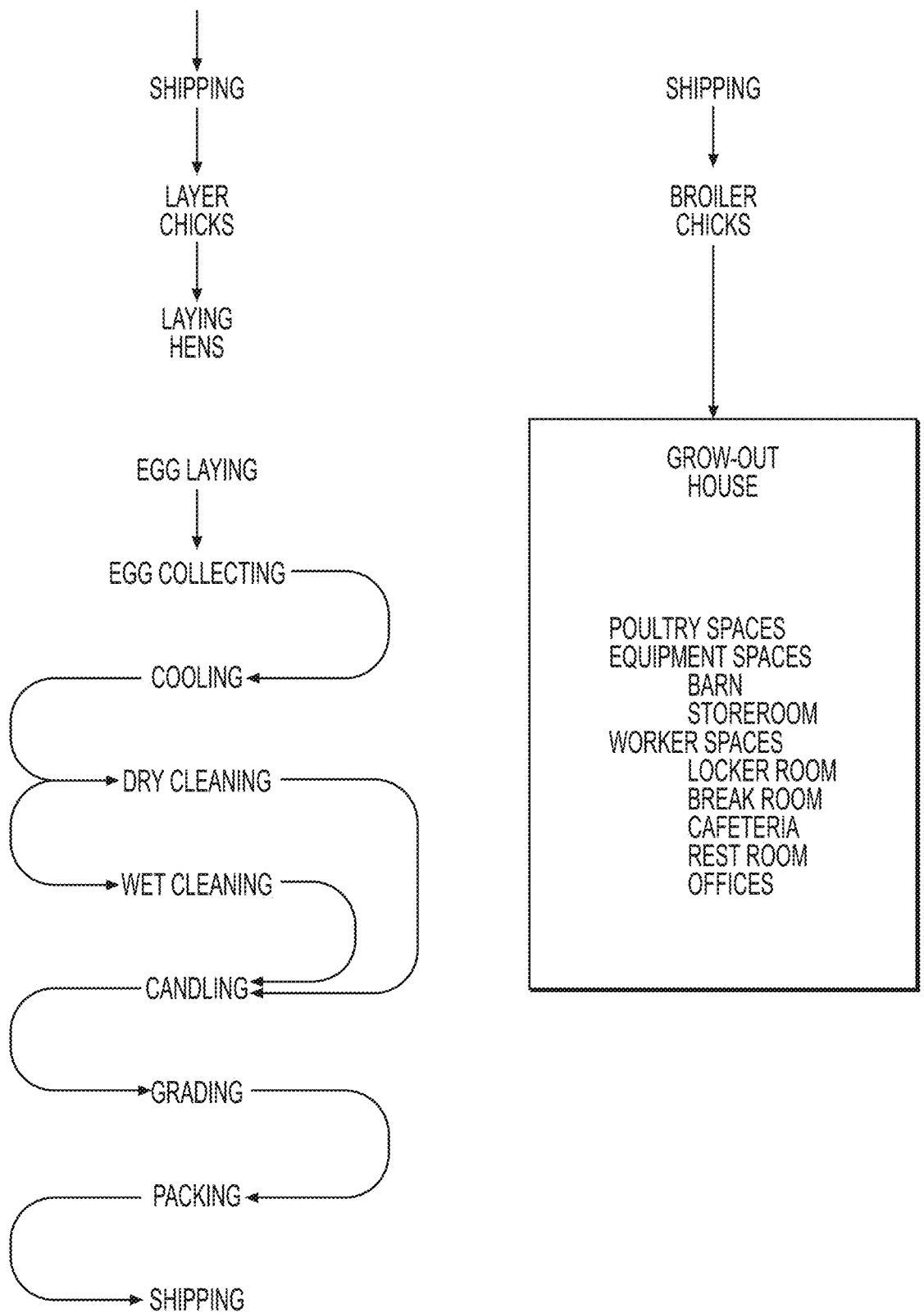
FIG. 5 is another diagram presenting non-limiting examples of the steps of the poultry production process after hatching that benefit from the application of DHP technology.

The present specification provides for and includes methods for reducing antibiotic use in a poultry production process comprising replacing antibiotic use with the treatment of poultry spaces with DHP. In an aspect, each step of the production process includes exposure to DHP gas at up to 10 ppm. As shown in FIG. 4, poultry production comprises three production stages: treatment of primary breeder flocks, treatment of the breeder farm flocks, and treatment at the hatchery. In an aspect, DHP gas treatment continues on the layer chicks and the broiler chicks at the grow out farm. As provided herein, reducing antibiotic use includes treatment of the incoming food. In an aspect, the use of DHP gas in poultry production begins in the laying facilities (primary breeder or breeder farm) such that the laying hens are treated with DHP gas, preferably continuously. In another aspect, methods for reducing antibiotic use include treating the eggs in a storage room prior to transfer to a setting or hatching incubator. In an aspect, methods for reducing antibiotic use includes exposing the eggs to DHP gas as provided herein while in the setting incubator. In another aspect, methods for reducing antibiotic use includes exposing the eggs to DHP gas as provided herein while in the hatching incubator. As shown in the examples, application of DHP gas at each individual stage of production reduces bacterial loads and reduces the need for antibiotics. In an aspect, to further reduce and eliminate the use of antibiotics during the poultry production process, the present specification provides for a continuous application of DHP gas at all stages of production. In an aspect, antibiotic free methods benefit from the application of DHP gas at a single step. The present specification provides for maintaining antibiotic free (ABF) and no antibiotics ever (NAE) flocks by treating the eggs, incubators, storage rooms, hatchings, and egg laying hens with DHP gas. Introduction of bacteria and other pathogens in methods for maintaining ABF and NAE flocks can be further reduced by treating tool rooms, break rooms, locker rooms, and other ancillary facilities with DHP gas to reduce sources of contamination and the introduction of disease into poultry production areas.

The present specification provides for, and includes, methods for reducing the risk of omphalitis comprising incubating poultry eggs in the presence of Dilute Hydrogen Peroxide (DHP) gas during pre-incubation storage or during hatching incubation. In an aspect, the eggs are placed into a storage room having DHP gas and a temperature below physiological zero for a time period. This storage period allows for the synchronization of egg development for eggs collected over a multi-day period. During this initial stage, bacterial counts are reduced. After storage, eggs are removed and transferred to a setting incubator having DHP gas and incubated according to normal procedures. As appropriate (e.g., when the setting and hatching incubators are separate), eggs are transferred to the hatching incubator having DHP gas as provided above. In an aspect, eggs are continuously treated with DHP gas to reduce the risk of omphalitis.

In an aspect, the methods to reduce the risk of omphalitis comprise treating the poultry eggs during on site storage, during setting incubation, and during hatching incubation. In an aspect, the first week mortality is reduced by at least 0.5%. In another aspect, the first week mortality is reduced by at least 1%. In another aspect, the first week mortality is reduced by at least 1.5%. In another aspect, the first week mortality is reduced by at least 2%. On yet other aspects, the first week mortality is reduced by at least 2.5%. In some aspects, the first week mortality is reduced by between 0.5% and 10%. In another aspect, first week mortality is reduced by between 0.5% to 5%.

In an aspect, the methods to reduce the risk of omphalitis comprise treating the poultry eggs during on site storage. In an aspect, the first week mortality is reduced by at least 0.5%. In another aspect, the first week mortality is reduced by at least 1%. In another aspect, the first week mortality is reduced by at least 1.5%. In another aspect, the first week mortality is reduced by at least 2%. On yet another aspect, the first week mortality is reduced by at least 2.5%. In some aspects, the first week mortality is reduced by between 0.5% and 10%. In another aspect, first week mortality is reduced by between 0.5% and 5%.

In an aspect, the methods to reduce the risk of omphalitis comprise treating the poultry eggs during setting incubation and during hatching incubation. In an aspect, the first week mortality is reduced by at least 0.5%. In another aspect, the first week mortality is reduced by at least 1%. In another aspect, the first week mortality is reduced by at least 1.5%. In another aspect, the first week mortality is reduced by at least 2%. On yet other aspects, the first week mortality is reduced by at least 2.5%. In some aspects, the first week mortality is reduced by between 0.5% and 10%. In another aspect, first week mortality is reduced by between 0.5% and 5%.

Vaccine production facilities receive eggs from smaller farms with lower contamination levels. These eggs are incubated in the same types of incubators used in hatcheries, but on a smaller scale. That said, each small batch of eggs (tens of thousands) is worth millions of dollars and one contaminated egg can ruin an entire batch. The present specification provides for and includes treatment of poultry spaces for the production of vaccines.

EMBODIMENTS

Embodiment 1: A method for improving poultry eggs comprising placing poultry eggs into a poultry space, providing dry hydrogen peroxide (DHP) at a concentration of between 0.01 ppm and 10 ppm to said poultry space, and maintaining said poultry eggs in said poultry space for a storage period.

Embodiment 2: The method of embodiment 1, wherein said improvement is an increase in hatchability.

Embodiment 3: The method of embodiment 1 or 2, wherein said improvement is an increase in uniformity.

Embodiment 4: The method of any one of embodiments 1 to 3, wherein said improvement is an increase in the average chick hatching weight.

Embodiment 5: The method of any one of embodiments 1 to 4, wherein said improvement is a reduction in the number of pipped unhatched eggs by 10%.

Embodiment 6: The method of any one of embodiments 1 to 5, wherein said improvement is a decrease in the number of second quality chicks by 10%.

Embodiment 7: The method of any one of embodiments 1 to 6, wherein said improvement is a reduction in the bacterial load of said poultry eggs by 10 fold.

Embodiment 8: The method of any one of embodiments 1 to 7, wherein said improvement is a decrease in 7-day mortality of hatched first quality chicks.

Embodiment 9: The method of any one of embodiments 1 to 8, wherein said storage period is between 1 and 3 days and said poultry space is a lay house or egg storage room.

Embodiment 10: The method of any one of embodiments 1 to 9, wherein said storage period is between 1 and 7 days and said poultry space is a hatchery egg room.

Embodiment 11: The method of any one of embodiments 1 to 10, wherein said storage period is between 1 and 18 days and said poultry space is a setting incubator.

Embodiment 12: The method of any one of embodiments 1 to 11, wherein said storage period is between 1 and 21 days and said poultry space is a combined setting and hatching incubator.

Embodiment 13: The method of any one of embodiments 1 to 12, wherein said storage period is between 1 and 5 days and said poultry space is a hatching incubator.

Embodiment 14: The method of any one of embodiments 1 to 13, wherein said DHP is provided directly to said poultry space.

Embodiment 15: The method of any one of embodiments 1 to 14, wherein said DHP is provided indirectly to said poultry space.

Embodiment 16: The method of embodiment 15, wherein said stored poultry eggs are provided short periods of incubation during egg storage (SPIDES).

Embodiment 17: A poultry space comprising dry hydrogen peroxide gas (DHPG) at a concentration of between 0.01 ppm and 10 ppm.

Embodiment 18: The poultry space of embodiment 17, wherein said poultry space is an egg receiving room, an incubator, a grow-out house, a pullet house, a lay house, a lay house egg/ante room, a hatchery, an egg room, an incubator, a hatchery room, a packing room, a chick holding room, or a breeder house.

Embodiment 19: The poultry space of embodiment 18, wherein said incubator is a setting incubator, a hatching incubator, or a combination setting and hatching incubator.

Embodiment 20: A method of killing coccidial oocysts of the phylum Apicomplexa in poultry litter comprising treating litter with dry hydrogen peroxide gas (DHPG) at a concentration of at least 0.01 ppm.

Embodiment 21: The method of embodiment 20, wherein said coccidial oocysts are oocysts of the genus *Eimeria* selected from the group consisting of *E. acervulina*, *E. brunetti*, *E. maxima*, *E. mitis*, *E. necatrix*, *E. praecox*, *E. tenella*, *Cryptosporidia*, and combinations thereof.

Embodiment 22: The method of embodiment 20 or 21, wherein said DHPG comprises less than 0.015 ppm ozone.

Embodiment 23: The method of any one of embodiments 20 to 22, wherein said treating comprises providing said dry hydrogen peroxide gas (DHPG) at a concentration of at least 0.1 ppm for at least 1 hour per day.

Embodiment 24: The method of any one of embodiments 20 to 23, wherein said treating comprises providing said dry hydrogen peroxide gas (DHPG) at a concentration of at least 0.20 ppm daily for a week.

Embodiment 25: A method of increasing the feed conversion ratio in poultry production comprising providing DHP gas at a concentration of at least 0.01 ppm to a population of growing birds.

Embodiment 26: The method of embodiment 25, wherein said food conversion ratio at day zero to day 21 is 1.42 or less.

Embodiment 27: The method of embodiment 25 or 26, wherein said feed conversion ratio at days 21 to 43 is 1.85 or less.

Embodiment 28: The method of any one of embodiments 25 to 27, wherein the consumption of darkling beetles by said population of growing birds is reduced by 10%.

Embodiment 29: A method of reducing damage to poultry production facilities from insect infestation comprising providing a poultry production facility with dry hydrogen peroxide gas (DHPG) at a concentration of at least 0.01 ppm.

Embodiment 30: The method of embodiment 29, wherein said DHPG is at a concentration of up to 10.0 ppm.

Embodiment 31: The method of embodiment 29 or 30, wherein said DHPG comprises less than 0.015 ppm ozone.

Embodiment 32: The method of any one of embodiments 29 to 31, wherein said dry hydrogen peroxide gas (DHPG) is provided at a concentration of at least 0.1 ppm for at least 1 hour per day.

Embodiment 33: The method of any one of embodiments 29 to 32, wherein said dry hydrogen peroxide gas (DHPG) is provided at a concentration of at least 0.2 ppm daily for a week.

Embodiment 34: The method of any one of embodiments 29 to 33, wherein said poultry production facility is a broiler house.

Embodiment 35: The method of any one of embodiments 29 to 34, wherein said insect is selected from the group consisting of *Alphitobius diaperinus* (darkling beetle), *Cimex lectularius* (bedbug), *Menocanthus stramineus* (biting lice), blackfly, *Knemidocoptes* spp. (depluming and scaly leg mites), *Dermanyssus gallinae* (red mite), *Ornithonyssus bursae* (northern fowl mite), and *Argas persicus* (ticks).

Embodiment 36: A method for reducing disease in a poultry production flock comprising providing a poultry production facility with dry hydrogen peroxide gas (DHPG) at a concentration of at least 0.01 ppm to said flock.

Embodiment 37: The method of embodiment 36, wherein said disease is infection by bacteria selected from the group consisting of *E. coli* (*Coli*-septicaemia), *Salmonella typhimurium*, *Salmonella enteritidis*, *Pasteurella multocida*, *Enterococcus faecalis*, *Bacillus cereus*, *Salmonella Arizonae*, *Staphylococcus aureus*, *Clostridium botulinum*, *Chlamydia psittaci*, and *Camplylobactor* spp.

Embodiment 38: The method of embodiment 36 or 37, wherein said disease is infection by mycobacteria selected from the group consisting of *Mycoplasma gallisepticum* (Chronic Respiratory Disease—Chickens; Infectious Sinusitis—Turkeys), *Mycoplasma immitans*, *Mycoplasma iowae*, *Mycoplasma meleagridis*, *Mycoplasma synoviae* (Infectious Synovitis), and *Mycobacterium tuberculosis* (MTB).

Embodiment 39: The method of any one of embodiments 36 to 38, wherein said disease is a parasitic disease selected from the group consisting of *Heterakis gallinae* (caecal worms), *Capillaria* spp. (*C. obsignata* and *C. contorta*), *Gongylonema ingluvicola* (cropworm), *Cheilospirura* (gizzard worm), *Streptocara* (gizzard worm), *Histiocephalus* (gizzard worm), proventricular worms, roundworms (*Ascaridia*), tapeworms (*Cestodes*), and trichomoniasis.

Embodiment 40: The method of any one of embodiments 36 to 39, wherein said disease is a viral disease selected from the group consisting of amyloidosis (coronavirus), Avian encephalomyelitis virus (egg drop), Avian Influenza-Highly Pathogenic (HPAI), Avian Leukosis, Avian Rhinotracheitis, Avian Hepevirus (Big Liver and Spleen Disease), Fowl Plague, Duck Viral Hepatitis, Duck Virus Enteritis, Avian Pox, goose Parvovirus (Derzsy's Disease), Inclusion Body Hepatitis, Hydropericardium-Hepatitis Syndrome (Angara Disease), Newcastle Disease (Paramyxovirus 1), Paramyxovirus 2—Yucaipa Disease, Paramyxovirus-3, Paramyxovirus-6, Respiratory Adenovirus Infection (Mild Respiratory Disease), Rotavirus, Turkey Viral Hepatitis, Vibrionic Hepatitis (Avian Infectious Hepatitis), Viral Arthritis, Transmissible Enteritis, Bluecomb, and Chicken Anaemia Virus (CAV).

Embodiment 41: The method of any one of embodiments 36 to 40, wherein said disease is a fungal disease selected from the group consisting of *Aspergillus fumigatus*, *Candida albicans*, and *Dactylaria gallopava*.

Embodiment 42: A method for reducing antibiotic use during the production of poultry comprising providing a poultry production facility with dry hydrogen peroxide (DHP) gas at a concentration of at least 0.01 ppm.

Embodiment 43: The method of embodiment 42, wherein said poultry production facility is an egg laying house.

Embodiment 44: The method of embodiment 43 or 42, wherein eggs in said egg laying house are exposed to DHP gas for at least 1 hour.

Embodiment 45: The method of any one of embodiments 42 to 44, wherein said eggs are exposed to DHP gas within 1 hour of being laid.

Embodiment 46: A method for reducing odors emanating from a poultry production facility comprising providing a poultry production facility with dry hydrogen peroxide gas (DHPG) at a concentration of at least 0.01 ppm.

Embodiment 47: The method of embodiment 46, wherein said DHP gas is provided at a concentration of at least 0.1 ppm.

Embodiment 48: The method of embodiment 46 or 47, wherein said DHP gas is provided continuously.

Embodiment 49: The method of any one of embodiments 46 to 48, wherein said odor comprises an amine, a sulfide, a volatile fatty acid, an indole, a skatole, a phenol, a mercaptan, an alcohol, or a carbonyl.

Embodiment 50: The method of any one of embodiments 46 to 49, wherein said odor comprises ammonia, volatile organic compounds, or hydrogen sulfide.

Embodiment 51: The method of any one of embodiments 46 to 50, wherein said odor is reduced by 25%.

Embodiment 52: A method for preventing the spread of a communicable disease in a poultry facility comprising identifying a poultry production facility having an introduced communicable disease and providing said poultry production facility with a PHPG generating device and generating dry hydrogen peroxide (DHP) gas at a concentration of at least 0.01 ppm.

Embodiment 53: The method of embodiment 52, wherein said communicable disease is an airborne transmissible disease.

Embodiment 54: The method of embodiment 52 or 53, wherein said airborne transmissible disease is Influenza A.

Embodiment 55: The method of any one of embodiments 52 to 54, wherein said introduction is an accidental introduction.

Embodiment 56: The method of any one of embodiments 52 to 54, wherein said introduction is an act of bioterrorism.

Embodiment 57: A kit comprising one or more portable DHP generating devices for use in a rapid response to an infectious disease outbreak on a poultry farm.

Embodiment 58: The kit according to embodiment 57, wherein the number of DHP generating devices provides a capacity of at least three times the number of devices necessary to maintain a space at a concentration of at least 0.01 ppm.

Embodiment 59: The kit according to embodiment 57 or 58, wherein the number of DHP generating devices provides a capacity of at least three times the number of devices necessary to maintain a space at a concentration of at least 0.10 ppm.

Embodiment 60: The kit according to embodiment 59, wherein the number of DHP generating devices provides a capacity of at least three times the number of devices necessary to maintain a space at a concentration of at least 0.5 ppm.

Embodiment 61: The kit according to embodiment 60, wherein the number of DHP generating devices provides a capacity of at least three times the number of devices necessary to maintain a space at a concentration of at least 1.0 ppm.

Embodiment 62: A method for treating an emergent disease at a poultry facility comprising providing said poultry facility with an excess of PHPG generating devices and generating dry hydrogen peroxide (DHP) gas at a concentration of at least 0.01 ppm.

Embodiment 63: The method of embodiment 62, wherein said emergent disease is an airborne transmissible disease.

Embodiment 64: The method of embodiment 63, wherein said airborne transmissible disease is selected from the group consisting of Influenza A, Newcastle disease, and infectious bronchitis (coronavirus).

Embodiment 65: The method of any one of embodiments 62 to 64, wherein said emergent disease is introduced accidentally.

Embodiment 66: The method of any one of embodiments 62 to 65, wherein said emergent disease is introduced as an act of bioterrorism.

Embodiment 67: A method for reducing the risk of omphalitis comprising incubating poultry eggs in the presence of Dilute Hydrogen Peroxide (DHP) gas during pre-incubation storage or during hatching incubation.

Embodiment 68: The method of embodiment 67, wherein the first week mortality is reduced by 0.5%.

Embodiment 69: The method of embodiment 67 or 68, wherein chicks hatched from said incubated poultry eggs are not administered antibiotics.

Embodiment 70: The method of any one of embodiments 67 to 69, wherein said eggs are obtained from a 25 to 30 week old hen flock.

Embodiment 71: The method of any one of embodiments 67 to 69, wherein said eggs are obtained from a 30 to 50 week old hen flock.

Embodiment 72: The method of any one of embodiments 67 to 69, wherein said eggs are obtained from a hen flock that is more than 50 weeks old.

Embodiment 73: A method for decreasing the microbial load of a poultry egg comprising collecting eggs from a plurality of hens, transferring the eggs to an egg room having a temperature below physiological zero and having up to 10 parts-per-million DHP gas, storing the eggs prior to incubation, and removing the eggs after a time period for transfer to an incubator.

Embodiment 74: The method of embodiment 73, wherein said time period is between one day and one week.

Embodiment 75: A storage room for poultry eggs comprising a temperature below physiological zero and up to 5 parts-per-million (ppm) of DHP gas.

Embodiment 76: The storage room of embodiment 75, wherein said DHP gas is a detectable level of DHP.

Embodiment 77: The storage room of embodiment 75 or 76, further comprising a relative humidity of between 75% and 88%.

Embodiment 78: The storage room of embodiment 75 or 76, wherein the relative humidity is between 75% and 80%.

Embodiment 79: The storage room of any one of embodiments 75 to 78, wherein said physiological zero temperature is 24° C. or less.

Embodiment 80: The storage room of any one of embodiments 75 to 78, wherein said temperature is maintained between 16° C. and 18° C.

Embodiment 81: The storage room of any one of embodiments 75 to 80, wherein said temperature is above 10° C.

Embodiment 82: An incubator comprising an enclosure; a temperature control system; and an air circulation system including a DHP gas generating system.

Embodiment 83: The incubator of embodiment 81, wherein said DHP gas generating system comprises a source of ultraviolet (UV) light and an air-permeable substrate structure having a catalyst on its surface and configured to generate DHP.

Embodiment 84: The incubator of any one of embodiments 82 or 83, further comprising an environmental control unit.

Embodiment 85: The incubator of any one of embodiments 82 to 84, further comprising an egg turning system.

Embodiment 86: The incubator of any one of embodiments 82 to 85, further comprising a carbon dioxide ($CO_2$) sensing system.

Embodiment 87: The incubator for poultry eggs of any one of embodiments 82 to 86, further comprising a clean air plenum.

Embodiment 88: The incubator for poultry eggs of any one of embodiments 82 to 87, wherein said air circulation system comprises one or more fans.

Embodiment 89: The incubator for poultry eggs of any one of embodiments 82 to 88, wherein said air circulation system is a laminar flow system.

Embodiment 90: The incubator for poultry eggs of any one of embodiments 82 to 89, wherein said fans are variable control fans.

Embodiment 91: The incubator for poultry eggs of any one of embodiments 82 to 90, wherein said enclosure is a cabinet or a room.

Embodiment 92: The incubator for poultry eggs of any one of embodiments 82 to 91, further comprising a humidifier.

Embodiment 93: The incubator for poultry eggs of any one of embodiments 82 to 92, wherein said incubator is a single-stage incubator.

Embodiment 94: The incubator for poultry eggs of any one of embodiments 82 to 93, wherein said incubator is a multi-stage incubator.

Embodiment 95: Dilute Hydrogen Peroxide (DHP) gas treated eggs comprising poultry eggs treated eggs are treated with up to 10 ppm DHP gas at a temperature below physiological zero for a storage period prior to incubation.

Embodiment 96: The DHP gas treated poultry eggs of embodiment 95, wherein said eggs have improved hatchability relative to non-DHP treated eggs.

Embodiment 97: The DHP gas treated poultry eggs of embodiment 95 or 96, wherein chicks hatched from said eggs have increased hatch weight relative to non-DHP treated eggs.

Embodiment 98: The DHP gas treated poultry eggs any one of embodiments 95 to 97, wherein said storage period is at least four days.

Embodiment 99: The DHP gas treated poultry eggs any one of embodiments 95 to 98, wherein said eggs have an improved fertile hatchability percentage that is at least 1% greater than non-DHP treated eggs Embodiment 100: The DHP gas treated poultry eggs any one of embodiments 95 to 99, having a reduced chick cull rate relative to non-DHP treated eggs.

Embodiment 101: The DHP gas treated poultry eggs any one of embodiments 95 to 100, having a reduced level of contaminated eggs at transfer.

Embodiment 102: The DHP gas treated poultry eggs any one of embodiments 95 to 101, wherein said eggs are chicken eggs, turkey eggs, duck eggs, goose eggs, or quail eggs.

Embodiment 103: Improved chicks hatched from DHP gas treated poultry eggs, wherein said DHP gas treated poultry eggs have been treated with up to 10 ppm DHP gas at a temperature below physiological zero for a storage period prior to incubation.

Embodiment 104: The improved chicks of embodiment 103, wherein said chicks have having a decreased seven (7) day mortality when raised on a grow-out farm under standard commercial conditions compared to a chicks obtained from non-DHP gas treated eggs.

Embodiment 105: The improved chicks of embodiment 103 or 104, wherein said chicks have a decreased on-farm mortality compared to chicks obtained from non-DHP gas treated eggs.

Embodiment 106: The improved chicks of any one of embodiments 103 to 105, wherein said chicks have an improved food conversion ratio (FCR) compared to chicks obtained from non-DHP gas treated eggs.

Embodiment 107: The improved chicks of any one of embodiments 103 to 106, wherein said FCR is at least 5% greater than the FCR of chicks obtained from non-DHP gas treated eggs.

Embodiment 108: The improved chicks of any one of embodiments 103 to 107, wherein said chicks have a decreased level of condemnation compared to chicks obtained from non-DHP gas treated eggs.

Embodiment 109: The improved chicks of any one of embodiments 103 to 108, wherein said condemnation is ante-mortem condemnation.

Embodiment 110: The improved chicks of any one of embodiments 103 to 109, wherein said condemnation is post-mortem condemnation.

Embodiment 111: The improved chicks of any one of embodiments 103 to 110, wherein said chicks have a reduced bacterial load by oropharyngeal or cloacal swab compared to chicks obtained from non-DHP gas treated eggs.

Embodiment 112: The improved chicks of any one of embodiments 103 to 111, wherein said eggs are chicken eggs, turkey eggs, duck eggs, or quail eggs.

Embodiment 113: Improved chicks hatched from DHP gas treated poultry eggs, wherein said DHP gas treated poultry eggs have been treated with up to 10 ppm DHP gas at a temperature below physiological zero for a storage period prior to incubation and incubated with up to 10 ppm DHP gas during setting and hatching incubation.

Embodiment 114: The improved chicks of embodiment 113, wherein said chicks have a decreased seven (7) day mortality when raised on a grow-out farm under standard commercial conditions compared to a chicks obtained from non-DHP gas treated eggs Embodiment 115: The improved chicks of embodiment 113 or 114, wherein said chicks have a decreased on-farm mortality compared to chicks obtained from non-DHP gas treated eggs.

Embodiment 116: The improved chicks of any one of embodiments 113 to 115, wherein said chicks have an improved food conversion ratio (FCR) compared to chicks obtained from non-DHP gas treated eggs.

Embodiment 117: The improved chicks of any one of embodiments 113 to 116, wherein said FCR is at least 5% greater than the FCR of chicks obtained from non-DHP gas treated eggs.

Embodiment 118: The improved chicks of any one of embodiments 113 to 117, wherein said chicks have a decreased level of condemnation compared to chicks obtained from non-DHP gas treated eggs.

Embodiment 119: The improved chicks of embodiment 118, wherein said condemnation is ante-mortem condemnation.

Embodiment 120: The improved chicks of embodiment 118, wherein said condemnation is post-mortem condemnation.

Embodiment 121: The improved chicks of any one of embodiments 113 to 120, wherein said chicks have a reduced bacterial load by oropharyngeal or cloacal swab compared to chicks obtained from non-DHP gas treated eggs.

Embodiment 122: The improved chicks of any one of embodiments 113 to 121, wherein said eggs are chicken eggs, turkey eggs, duck eggs, or quail eggs.

Embodiment 123: A method for incubating eggs comprising: a) obtaining eggs for hatching; b) placing said eggs into an incubator capable of producing dry hydrogen peroxide (DHP) gas at a concentration of between 0.001 parts per million (ppm) and 10 ppm; c) a first incubating of said eggs in said incubator for between 1 and 18 days in the presence of DHP gas at a concentration of between 0.001 parts per million (ppm) and 10 ppm.

Embodiment 124: The method of embodiment 123, further comprising a second incubating of said eggs for between 1 to 5 days, or until hatching is complete, in the presence of dry hydrogen peroxide (DHP) at a concentration of between 0.001 parts per million (ppm) and 10 ppm.

Embodiment 125: The method of embodiments 123 or 124, wherein said second incubating is in a second incubator.

Embodiment 126: The method of any one of embodiments 123 to 125, wherein said eggs for hatching are stored at a temperature below physiological zero and dilute hydrogen peroxide (DHP) gas at a concentration between 0.001 and 5 parts-per-million (ppm) of DHP gas for between 1 and 7 days prior to step (b).

Embodiment 127: The method of any one of embodiments 123 to 126, wherein said DHP gas concentration is at least 0.01 ppm.

132. Embodiment 128: The method of any one of embodiments 123 to 127, wherein said DHP gas concentration is at least 0.01 ppm.

While the present disclosure has been described with reference to particular embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular embodiments disclosed as the best mode contemplated for carrying out the present disclosure, but that the present disclosure will include all embodiments falling within the scope and spirit of the appended claims.

EXAMPLES

Example 1: Measurement of DHP

Hydrogen peroxide gas of the present specification can be measured using a Drager Polytron based method. A polytron sensor is provided with a pump to force air across the sensor to the environment. The hydrogen peroxide is reduced by the sensor, which measures the combined voltage of the reduction reactions taking place and uses an algorithm to provide a readout indicating the DHP concentration based on the overall voltage measured method. The amount of DHP detected is divided by the amount of air pumped.

Hydrogen peroxide gas of the present specification can be measured using the Drager Rohrchen method. The Rohrchen method involves using a Drager pump to force air through a tube containing a potassium iodide salt. As DHP reacts with the salt, the pure white salt darkens using the same reaction commonly employed in iodide titration methods used to determine peroxide concentration in solution. After 100 pumps, the furthest limit (distance into the tube) of the darkened color is located in the tube and compared to the calibrated concentration markings on the tube itself.

Example 2: Eggs and Quality Assessment

Hatching eggs are obtained from a breeder farm and the eggs are subjected to standard egg cleaning and preparation procedures. Hatched chicks are collected and prepared according to standard procedures (separation of eggshells and unhatched eggs, counted, etc.). Chicks are graded according to established methods. See van de Ven et al., "Significance of chick quality score in broiler production," *Animal* 6(10):1677-1683; Boerjan, "Programs for single stage incubation and chick quality," *Avian Poultry Biology Reviews* 13:237-238 (2002); Tona et al, "Effects of egg storage time on spread of hatch, chick quality and chick juvenile growth," *Poultry Science* 82:736-741 (2003).

As indicated, certain studies were performed at Western Hatchery in Abbotsford, British Columbia, Canada ("Western"), under the supervision of the inventors and assignee. Approximately 4 million eggs per month are processed through the hatchery.

Example 3: Egg Room Procedures Incorporated DHP Gas Treatment

In May 2016, DHP generating devices are installed in the "egg room" (receiving area) at Western. The egg room is contiguous to the loading and receiving area of the facility and is exposed to the outside during deliveries for up to 2 to 3 hours daily. The dimensions of the egg room are approximately 60×14×11 ft (18×4.2×33.5 m). In addition to the incoming eggs, the egg room includes excess shipping boxes and pallets. The HVAC system for the egg room area includes two supply ducts, and three DHP devices each are installed on the two supply ducts. DHP levels are determined to be between 0.1 ppm and 0.2 ppm. This level of DHP is sufficient to eliminate flies and other unwanted insects that are sources of contamination. Such levels provide for reductions in bacterial, viral, and fungal pathogens.

In June 2016, the egg room and facilities are modified to add a vestibule to the loading dock with plastic curtains and upgrading the HVAC system to provide a third supply duct.

Each duct is provided with three DHP devices (nine total). The use of the egg room is further modified to remove unnecessary equipment including, but not limited to, pallets, cardboard boxes, and crates. These items are sources of both contaminants and volatile organic compounds (VOCs) and can decrease the effective concentration of DHP. These improvements allow for the maintenance of DHP levels between about 0.3 and about 0.7 ppm.

The incorporation of DHP into the egg room eliminates flies and other unwanted insects, both flying and non-flying, that are sources of contamination. The DHP further improves the egg room by reducing odors.

Eggs are stored for up to 7 to 9 days in the DHP modified egg room before proceeding to incubation. As shown in Table 5, FIG. 6, and FIG. 7, the installation of DHP and improvements result in a 0.2% to 0.5% decline in cull rate in the egg room between June and July, and is at least 1% lower than the cull rate before DHP modification. Thus, the installation of DHP in the egg room results in about 4,000 additional birds available for shipping to the grow-out facility.

TABLE 6

Effect of DHP on Chick Production

| Month (2016) | Before Modification Cull Rate(%) | Before Modification First Quality Chick (% Hatched) | After Modification Cull Rate(%) | After Modification First Quality Chick (% Hatched) |
| --- | --- | --- | --- | --- |
| June | 2.90 | 77.60 | 2.09 | 78.62 |
| July | 3.25 | 80.12 | 1.88 | 79.78 |
| August | 3.01 | 79.66 | 1.58 | 79.90 |
| September | 3.53 | 77.78 | 1.63 | 81.09 |
| October | 3.32 | 80.90 | 1.32 | 82.55 |
| November | 3.50 | 80.34 | 1.41 | 82.96 |
| December | 3.59 | 78.38 | n/a | n/a |
| Average | 3.30 | 79.25 | 1.65 | 80.82 |
| Std. Dev. | 0.27 | 1.32 | 0.29 | 1.70 |

Example 4: Incubation Procedures Incorporating DHP Gas Treatment

In August 2016, the Western facility is further modified to introduce DHP technology to the incubation area containing setting incubators (Jamesway). DHP is supplied through the HVAC system into the hatcher hallway. Setter incubators are set to industry standard conditions: temperature between 37° C. and 38° C. and relative humidity between 40% and 70%. The setting incubation room is maintained at a DHP level of about 0.5 ppm. This provides for DHP to enter the incubators through the existing air intakes. Levels of DHP in the incubators are not determined.

Figure 6:
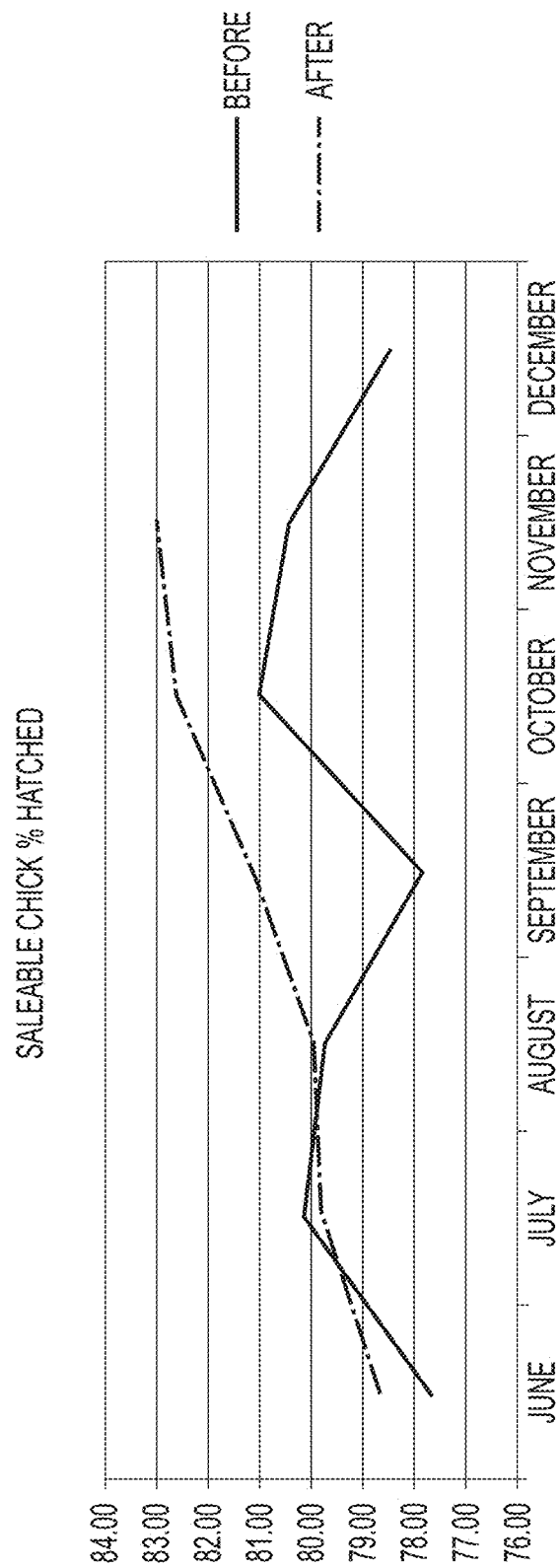
FIG. 6 is a graph presenting the effect of DHP on the percent hatching of first quality chicks according to an aspect of the present specification.
Figure 7:
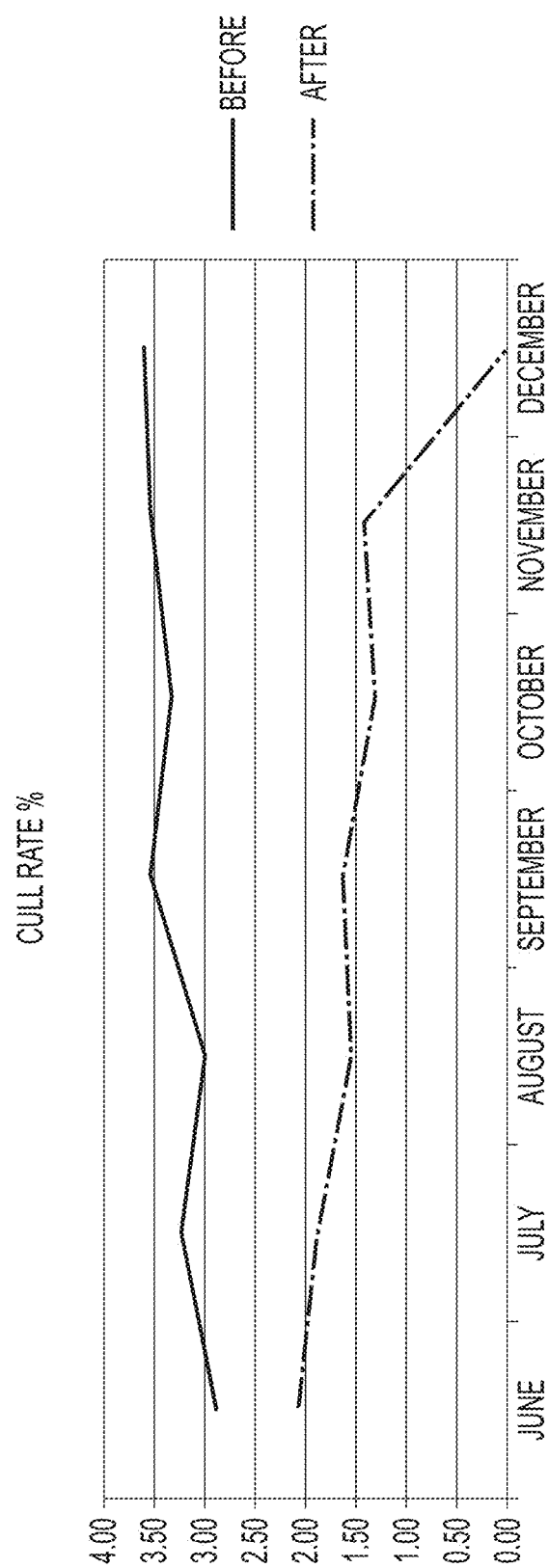
FIG. 7 is a graph presenting the effect of DHP on the cull rate of chicks according to an aspect of the present specification.

DHP treated eggs are moved from the egg room of Example 1 and placed in the incubators and incubated according to standard conditions for 18 days. FIG. 6 presents the percent hatching of first quality chicks. Notably, the percent hatching sharply increases after installation of DHP to the setter incubator environment and reaches 83%. As shown in FIG. 7, the cull rate continues to drop for eggs incubated under DHP conditions.

Example 5: Production of Flocks Treated with DHP

The chicks hatched according to the methods of Examples 2 and 3 are shipped to a broiler facility and raised to maturity. No additional changes to grow-out methods are made. A total of about 4 million eggs are set per month and the saleable chicks are sent to the grow-out facility. As shown in Table 6, DHP treatment not only improves the percent of saleable chicks, but profoundly improves the overall quality of the chicks sent to the grow-out facility. As discussed in Examples 2 and 3, the reduction of culling and improved chick quality results in an average of 62,000 more chicks for sale from each 4,000,000 eggs set. At the grow-out facility, the superior quality of the chicks is evident by the reduction of mortality of about 7.8%. This provides for an increase in overall production of over 300,000 broilers. The wholesale price of a broiler is currently estimated at $0.85 per pound. At an average carcass weight of about 4 lb (1.8 kg), the improvements of DHP to broiler production is valued at over $1,000,000 per month. See the nationalchickencouncil.org available on the web.

TABLE 7

Increases in Monthly Broiler Production After DHP Treatment

| Number | Before | After |
| --- | --- | --- |
| Eggs Set per month | 4,000,000 | 4,000,000 |
| Saleable Chick (average) | 3,213,600 | 3,318,400 |
| Percent Saleable Chicks | 79.25% | 80.82% |
| Net increase(# Chicks) | | 62,000 |
| Broilers raised | 2,853,000 | 3,161,678 |
| Mortality Rate | 10% | 2.2% |
| Net increase(# Broilers) | | 308,678 |

Example 6: DHP Reduces *Salmonella* Bacterial Load

After 28 days, *Salmonella* in the hatchery environment on the egg surface is reduced by 83.3% and maintained at this level.

The incubator room is a large room filled with banks of incubators. DHP devices are supplying air only to the area outside the incubators, and it enters the incubators through air intakes, but this is not the most efficient method, even though we see an overall reduction in *Salmonella* on the eggs of 83.3% between their time in the egg room (rack of eggs in a large open space) and in the incubators (racks of eggs in enclosed incubators).

Example 7: Hatching Procedures Incorporating DHP Treatment

Shortly before hatching, as determined per standard procedures, the setter incubated eggs according to Example 3 are moved from the setter incubators in the modified incubator room to a hatching incubator in a modified incubator room or to modified hatching incubators. In some aspects, the incubation incubator and the hatching incubator are the same; however, it is well known that using separate incubators can reduce the costs of cleanup and decontamination.

Chicks are hatched in the presence of DHP. Fluff, the normal byproduct of hatching and chick development, is often contaminated with disease organisms. The presence of DHP reduces the levels of contaminants and further improves the health of the newly hatched chicks.

Example 8: Vaccine Production in DHP Treated Eggs

The production of vaccines is improved through the application of DHP. Layers for the production of eggs for vaccines are incubated and hatched according to Examples 1 to 4. Layers are raised to maturity under DHP conditions and eggs are collected. Eggs produced from this process have significantly lower levels of contaminants than eggs produced under standard conditions.

Candidate vaccine viruses (CVVs) are injected into the DHP fertilized eggs and incubated for several days using standard methods in a space having DHP at a level of between 0.01 ppm and 10 ppm. Virus containing fluid is harvested from the eggs. The resulting virus is inactivated and the virus antigens are purified for the production of vaccine.

Example 9: Improved Incubators

To improve the provision of DHP during egg incubation, commercial incubators are modified to incorporate a PHPG generating device into the air intake. This provides for DHP directly to the inside of the incubator and provides for control of the DHP level. In an aspect, the modified incubator further includes a device for measuring DHP levels and for controlling the PHPG generating device.

Example 10: DHP Eliminates Influenza A (H1N1)

The effectiveness of DHP against Influenza A (H1N1) on a surface is tested by exposing glass slides inoculated with virus to DHP at 0.6 to 1.0 ppm. Glass slides (1"×3") are ethanol-sanitized and autoclaved prior to testing. The slides (carriers) are placed into sterile plastic petri dishes until use. Aliquots (0.010 ml) of diluted stock Influenza A (H1N1) are aseptically spread over a 1"×1" square area of the carrier slide to prepare a virus film. Duplicate carriers are prepared and designated as follows: (2-Time Zero Virus Control; 2-T=60 min Virus Control; 2-T=120 min Virus Control; 8-Virus Test Carriers (2 per Device Testing Chamber). Slides are dried for 25 minutes, 24.0° C., 36% relative humidity.

Upon drying, the carriers are placed into either a modular room pre-conditioned with DHP (Temperature=24.6° C., relative humidity 36%; DHP=0.6 ppm using Polytron method; DHP=1.0 ppm using Rohrchen method) and the lids of the petri dishes are removed. Virus Control carriers are placed into an adjacent modular room with the lids removed. One additional glass slide (with no virus film) is also placed into each testing chamber to perform cytotoxicity and neutralization validation controls. Upon closure of the respective study contact times (T=60 min and T=120 min), duplicate carriers are removed from each testing chamber. Duplicate carriers are also removed from the control modular room at each time point. Duplicate time zero carriers are harvested and enumerated promptly by eluting the films with 2 ml of influenza Infection Medium. Serial dilutions (1:10) are performed and dilutions $10-^{1}$ to $10-^{5}$ are plated in quadruplicate onto Madin-Darby Canine Kidney (MDCK) cell monolayers prepared to suitable confluency. Cell culture assay trays are incubated at 35° C. on an orbital rotator (60 rotations/minute) for 60 minutes to facilitate viral-host adsorption. Trays are removed from incubation, and Influenza infection Media is pipetted into each well (−1.0 ml). The trays are incubated for 7 days. The assay trays are observed regularly for the presence of cytotoxicity, viral cytopathic effects, and contamination. At the end of 7 days, plates are scored and the Spearman-Karber Method is used to compute viral titers and levels of cytotoxicity. The results are presented in Table 7.

TABLE 8

DHP Effect on Influenza A (H1N1) on a Surface

| | | Modular Room | | Hood Chamber | |
|---|---|---|---|---|---|
| Test Virus | Contact | Log10 | % Reduction | Log10 | % Reduction |
| Influenza A (HINI) | 60 minutes | 0.87 | 87% | >=2.62 | 99.8% |
| | 120 minutes | 0.62 | 76% | >=1.87 | 98.6% |

Example 11: DHP Eliminates Bacteria on Surfaces

The effectiveness of DHP on *S. aureus* ATCC 33592 (MRSA), *A. brasiliensis* ATCC 16404, and *C. difficile* (endospores) ATCC 43598 is tested according to the methods of Example 10. 24 and 48 hour test cultures of *S. aureus*, as well as all *A. brasiliensis* and *C. difficile* are prepared with 0.1% Triton X-100. A 6 hour test culture of *S. aureus* is prepared with 5.0% Petal Bovine Serum and no Triton. Carriers (slides) are inoculated, in duplicate per test microorganism per condition, at a target concentration of $1\times10^{6}$ CPU/Carrier. Inoculated carriers are allowed to dry at ambient temperatures, and are then placed in respective conditions to endure contact times. Carriers for *S. aureus* endured contact times of 6, 24, and 48 hours. Carriers for *A. brasiliensis* endured contact times of 12, 24, and 48 hours. Carriers for *C. difficile* endured contact times of 24, 48, and 72 hours. After respective contact times, carriers are harvested in 10.0 mL of D/E Broth, vortex mixed, diluted, and plated on the appropriate growth media for each microorganism. Environmental conditions are monitored using the Drager Rohrchen, and Drager Polytron methods described in Example 1. The results for *S. aureus* are presented in Table 8. The results for *A. brasiliensis* are presented in Table 9. The results for *C. difficile* are presented in Table 10. (Note: The limit of detection for this assay is 5.0 CPU. Samples with no detectable colonies are listed as <5.00E+OO in the table).

TABLE 9

Effect of DHP on *S. aureus*

| Test Microorganism | Contact Time | Carrier Position | Replicate | Replicate CFU/Carrier | Average CFU/Carrier | % Reduction compared | Log Reduction compared to |
|---|---|---|---|---|---|---|---|
| *S. aureus*ATCC 33592 (MRSA) | Initial | Time Zero | 1 | 7.40E+06 | 5.75E+06 | NIA | |
| | | | 2 | 4.10E+06 | | | |
| | 6 Hours | Room (Control) | 1 | 4.05E+06 | 5.18E+06 | NIA | |
| | | | 2 | 6.30E+06 | | | |
| | | Room (Treated) | 1 | 2.54E+05 | 8.77E+05 | 83.053% | 0.77 |
| | | | 2 | 1.50E+06 | | | |

TABLE 9-continued

Effect of DHP on *S. aureus*

| Test Microorganism | Contact Time | Carrier Position | Replicate | Replicate CFU/Carrier | Average CFU/Carrier | % Reduction compared | Log Reduction compared to |
|---|---|---|---|---|---|---|---|
| | | Hood (Treated) | 1 | 1.62E+05 | 2.51E+05 | 95.150% | 1.31 |
| | | | 2 | 3.40E+05 | | | |
| | 24 Hours | Room (Control) | 1 | 4.00E+01 | 4.50E+01 | NIA | |
| | | | 2 | 5.00E+01 | | | |
| | | Room (Treated) | 1 | 5.00E+00 | <5.00E+00 | >88.889% | >0.95 |
| | | | 2 | <5.00E+00 | | | |
| | | Hood (Treated) | 1 | 2.50E+01 | <1.50E+01 | >66.667% | >0.48 |
| | | | 2 | <5.00E+00 | | | |
| | 48 Hours | Room (Control) | 1 | 4.00E+01 | 4.75E+01 | NIA | |
| | | | 2 | 5.50E+01 | | | |
| | | Room (Treated) | 1 | <5.00E+00 | <5.00E+00 | >89.474% | >0.98 |
| | | | 2 | <5.00E+00 | | | |
| | | Hood (Treated) | 1 | <5.00E+00 | <1.00E+01 | >78.947% | >0.68 |
| | | | 2 | 1.50E+01 | | | |

TABLE 10

Effect of DHP on *A brasiliensis*

| Test Microorganism | Contact Time | Carrier Position | Replicate | Replicate CFU/Carrier | Average CFU/Carrier | Percent Reduction compared to Control | Log Reduction compared to Control |
|---|---|---|---|---|---|---|---|
| *A. brasiliensis* ATCC 16404 | Initial | Time Zero | 1 | 3.65E+06 | 2.93E+06 | NIA | |
| | | | 2 | 2.20E+06 | | | |
| | 12 Hours | Room (Control) | 1 | 1.65E+06 | 2.28E+06 | NIA | |
| | | | 2 | 2.90E+06 | | | |
| | | Room (Treated) | 1 | 2.80E+06 | 3.10E+06 | None | None |
| | | | 2 | 3.40E+06 | | | |
| | | Hood (Treated) | 1 | 2.10E+06 | 2.18E+06 | 4.40% | 0.02 |
| | | | 2 | 2.25E+06 | | | |
| | Initial | Time Zero | 1 | 3.95E+06 | 4.28E+06 | NIA | |
| | | | 2 | 4.60E+06 | | | |
| | 24 Hours | Room (Control) | 1 | 1.65E+06 | 1.90E+06 | NIA | |
| | | | 2 | 2.15E+06 | | | |
| | | Room (Treated) | 1 | 1.75E+06 | 1.43E+06 | 25.00% | 0.12 |
| | | | 2 | 1.60E+06 | | | |
| | | Hood (Treated) | 1 | 9.50E+05 | 9.75E+05 | 48.68% | 0.29 |
| | | | 2 | 1.00E+06 | | | |
| | 48 Hours | Room (Control) | 1 | 9.50E+05 | 1.28E+06 | NIA | |
| | | | 2 | 1.60E+06 | | | |
| | | Room (Treated) | 1 | 1.35E+06 | 1.70E+06 | None | None |
| | | | 2 | 2.05E+06 | | | |
| | | Hood (Treated) | 1 | 7.00E+05 | 6.75E+05 | 47.06% | 0.28 |
| | | | 2 | 6.50E+05 | | | |

TABLE 11

Effect of DHP on *C. difficile*

| Test Microorganism | Contact Time | Carrier Position | Replicate | Replicate CFU/Carrier | Average CFU/Carrier | Percent Reduction Compared to Control | Log Reduction Compared to Control |
|---|---|---|---|---|---|---|---|
| *C. difficile* ATCC 43598 (endospores) | Initial | Time Zero | 1 | 3.30E+06 | 3.78E+06 | NIA | |
| | | | 2 | 4.25E+06 | | | |
| | 24 Hours | Room (Control) | 1 | 1.71E+06 | 1.77E+06 | NIA | |
| | | | 2 | 1.84E+06 | | | |
| | | Room (Treated) | 1 | 4.80E+05 | 1.53E+06 | 13.96% | 0.07 |
| | | | 2 | 2.57E+06 | | | |

TABLE 11-continued

Effect of DHP on *C. difficile*

| Test Microorganism | Contact Time | Carrier Position | Replicate | Replicate CFU/Carrier | Average CFU/Carrier | Percent Reduction Compared to Control | Log Reduction Compared to Control |
|---|---|---|---|---|---|---|---|
| | | Hood (Treated) | 1 | 3.06E+06 | 2.75E+06 | None | None |
| | | | 2 | 2.44E+06 | | | |
| | | Room (Control) | 1 | 5.55E+06 | 5.35E+06 | NIA | |
| | | | 2 | 5.15E+06 | | | |
| | | Room (Treated) | 1 | 4.85E+06 | 3.53E+06 | 34.11% | 0.18 |
| | | | 2 | 2.20E+06 | | | |
| | | Hood (Treated) | 1 | 4.35E+06 | 3.10E+06 | 42.06% | 0.24 |
| | | | 2 | 1.85E+06 | | | |
| | 72 Hours | Room (Control) | 1 | 3.85E+06 | 3.68E+06 | NIA | |
| | | | 2 | 3.50E+06 | | | |
| | | Room (Treated) | 1 | 2.70E+06 | 3.35E+06 | 8.84% | 0.04 |
| | | | 2 | 4.00E+06 | | | |
| | | Hood (Treated) | 1 | 1.55E+06 | 1.80E+06 | 51.02% | 0.31 |
| | | | 2 | 2.05E+06 | | | |

Example 12: Prevention of Contamination by Airborne Pathogens

The transmission of airborne pathogens such as aerosolized bacteria and viruses is a critical concern in poultry production facilities. Introduction of such pathogens can decimate a flock. In addition to the application of DHP to productive spaces of a poultry facility, DHP can prevent the transmission of airborne pathogens through the treatment of auxiliary areas such as worker break rooms, locker rooms, equipment rooms, barns, and offices. DHP is effective at killing airborne bacteria and viruses.

Test pathogens *E. coli* K12, and MS2 Bacteriophage ATCC 15597-B1 are aerosolized into a 500 square foot building having 8 foot ceilings (114 m\ The building has an initial DHP concentration of 0 ppm at time zero. To provide DHP, an HVAC device as described in WO 2015/171633 is mounted to a duct and a fan to produce a stand-alone HVAC device and turned on at time zero. Within one hour, levels of DHP are measured at 0.5 ppm. Samples are collected and tested at the times indicated in Table 11. As shown in Table 11, aerosolized bacteria are essentially eliminated from the DHP treated space within one hour, demonstrating the rapid effect of DHP on airborne bacteria. It is anticipated that the elimination of airborne bacteria is nearly complete well before an hour has elapsed. In contrast to the DHP treated space, the decrease in airborne bacteria is due to settling of the bacteria.

Similar results are observed for airborne viruses. As shown in Table 11, the phage is essentially eliminated within one hour with only 17 CFU/m$^3$ remaining. Like the bacteria, it is anticipated that the destruction of any airborne virus occurs within minutes of treatment with DHP.

TABLE 12

DHP Eliminates Aerosolized Pathogens

| Organism | DHP | Time (hours) | Recovery (CFU/m$^3$) | Percent reduction | Log$_{10}$ reduction | % Reduction vs. Control | Log$_{10}$ reduction vs. Control |
|---|---|---|---|---|---|---|---|
| *E. coli* | (−) | 0 | 1.03E+06 | | | | |
| | (−) | 1 | 1.13E+04 | 98.91% | 1.96 | | |
| | (−) | 2 | 8.66E+02 | 99.92% | 3.08 | | |
| | (−) | 3 | <1.52E+01 | >99.9985% | >4.83 | | |
| | (−) | 4 | <1.60E+01 | >99.9985% | >4.81 | | |
| | (+) | 0 | 1.03E+06 | | | | |
| | (+) | 1 | <1.70E+01 | >99.9984% | >4.78 | 99.8% | 2.82 |
| | (+) | 2 | <1.68E+01 | >99.9984% | >4.79 | 98.1% | 1.71 |
| MS2 Bacteriophage | (−) | 0 | 5.84E+04 | | | | |
| | (−) | 1 | 8.61E+03 | 85.3% | 0.83 | | |
| | (−) | 2 | 2.20E+03 | 96.2% | 1.42 | | |
| | (−) | 3 | 5.83E+02 | 99.0% | 2.00 | | |
| | (−) | 4 | 7.59E+02 | 98.7% | 1.89 | | |
| | (+) | 0 | 5.83E+04 | | | | |
| | (+) | 1 | 1.70E+01 | 99.97% | 3.54 | 99.8% | 2.70 |

Example 13: Improved Incubators

To improve the provision of DHP during egg incubation, commercial incubators (Jamesway) are modified to incorporate a PHPG generating device as part of an air-recirculation system 100. Incorporating a PHPG generating device in a separate recirculation system provides for greater flexibility in incubator design and allows for the retrofitting of existing incubators. The recirculating system provides for, but does not require, an independent controller and an independent filtration system. In addition to controlling temperature, incubators provide for the control of humidity in incubators. Thus, the recirculated air is humidified air, generally at a relative humidity of 50% or higher.

Figure 8A:
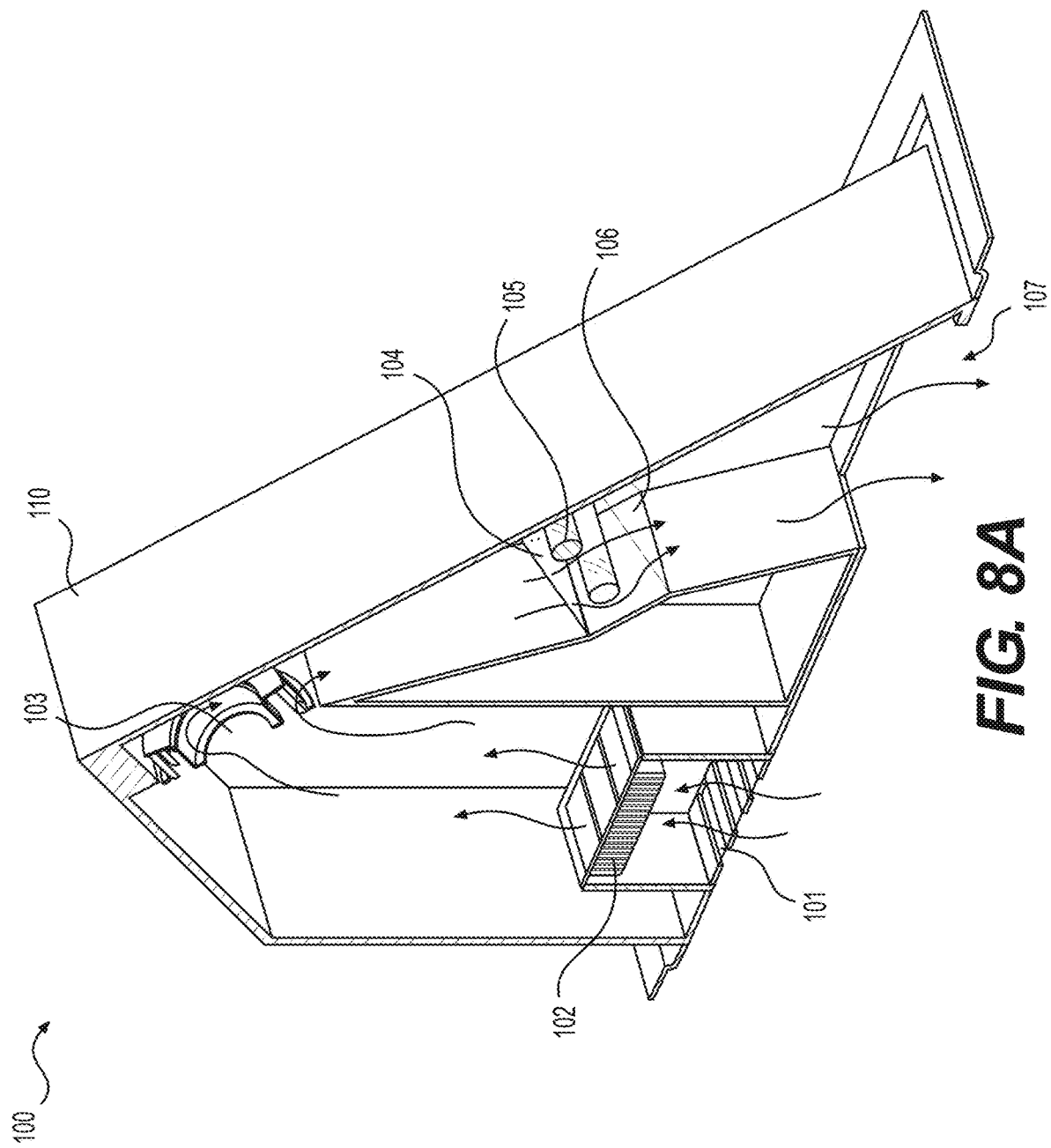
Figure 8B:
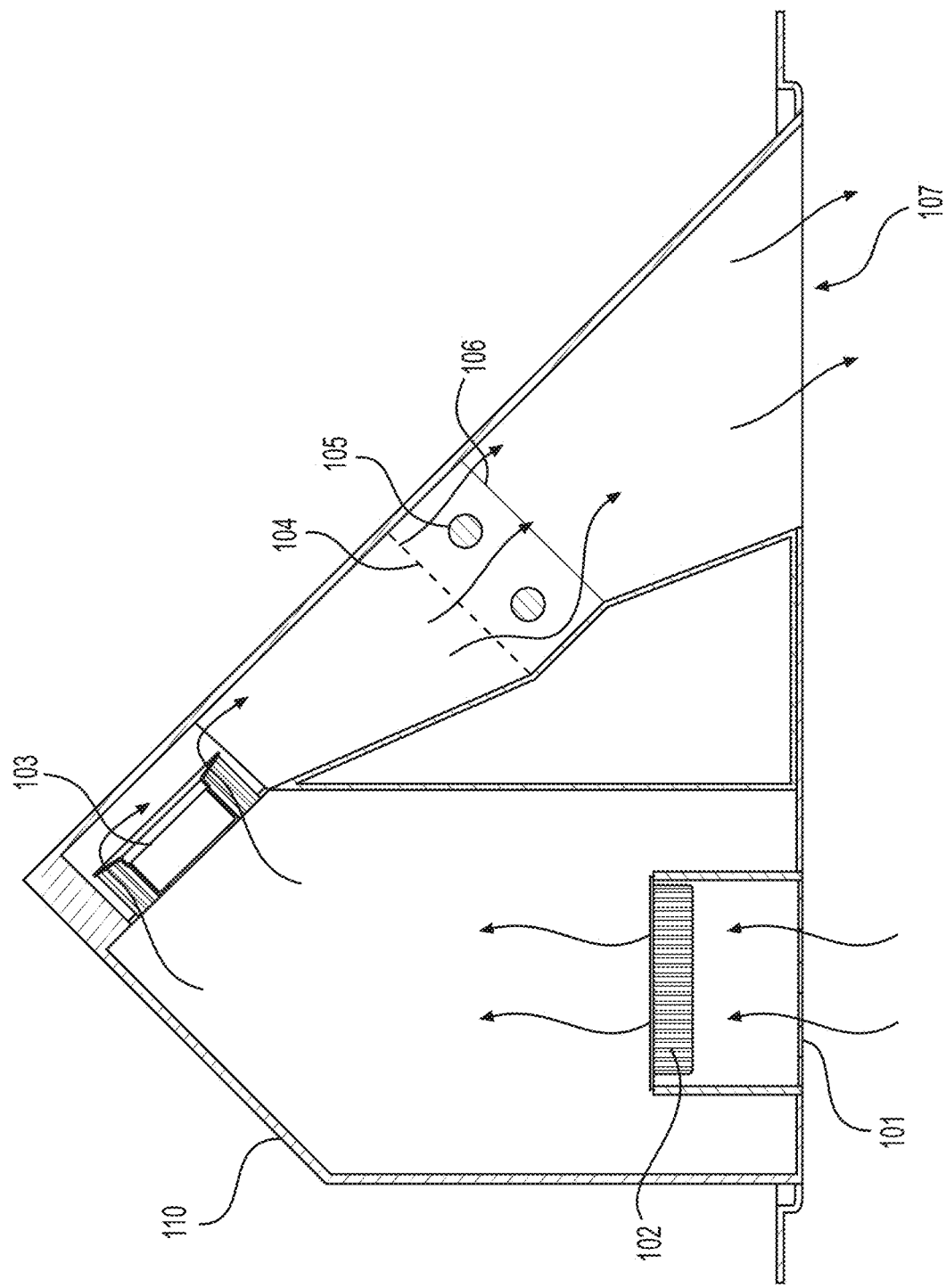
Figure 8D:
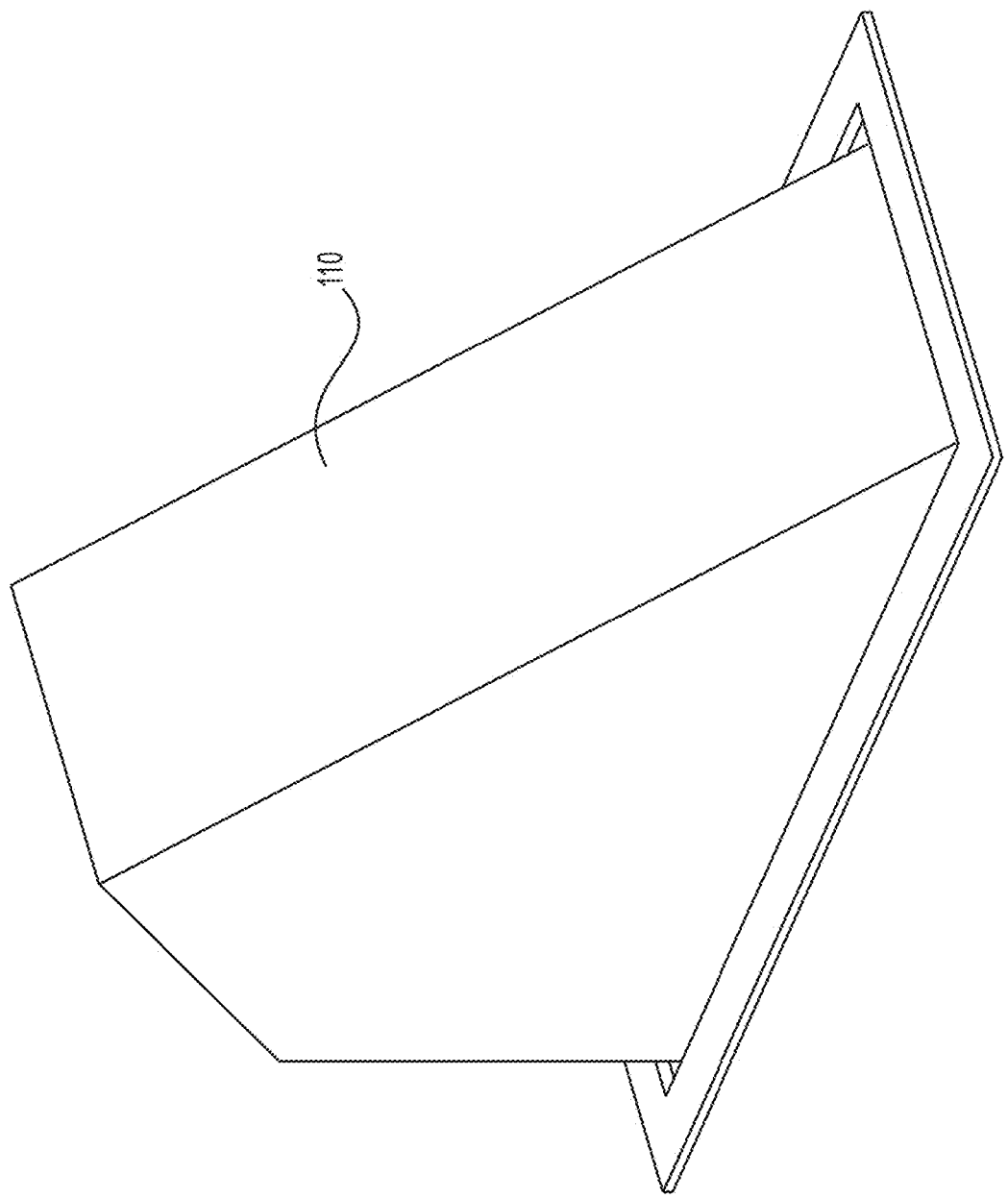
Figure 9A:
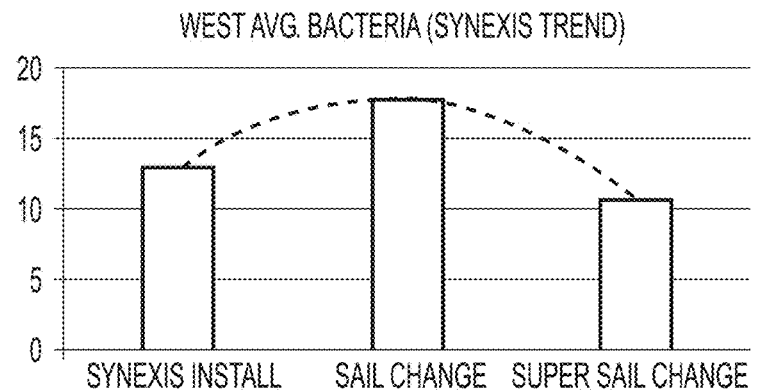
FIGS. 9A-C are graphs presenting the results of the effect of DHP gas on the number of bacteria detected in an on-site egg storage room according to an embodiment of the present specification.
Figure 9B:
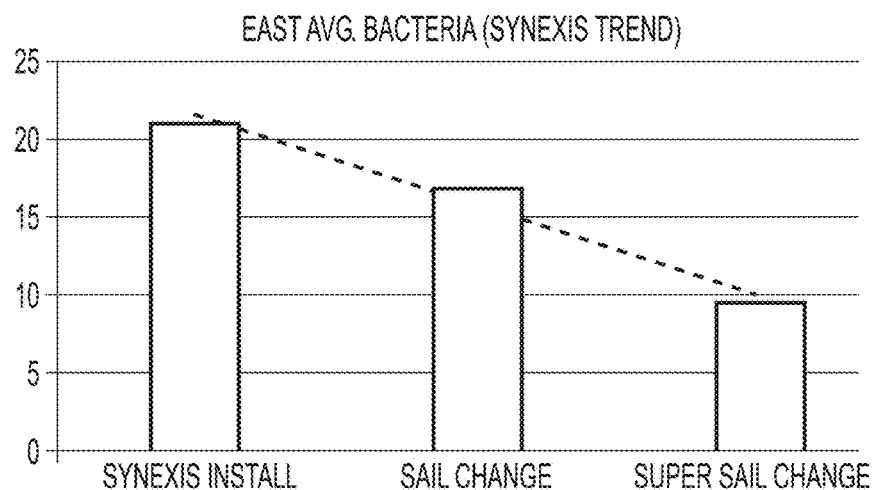
Figure 9C:
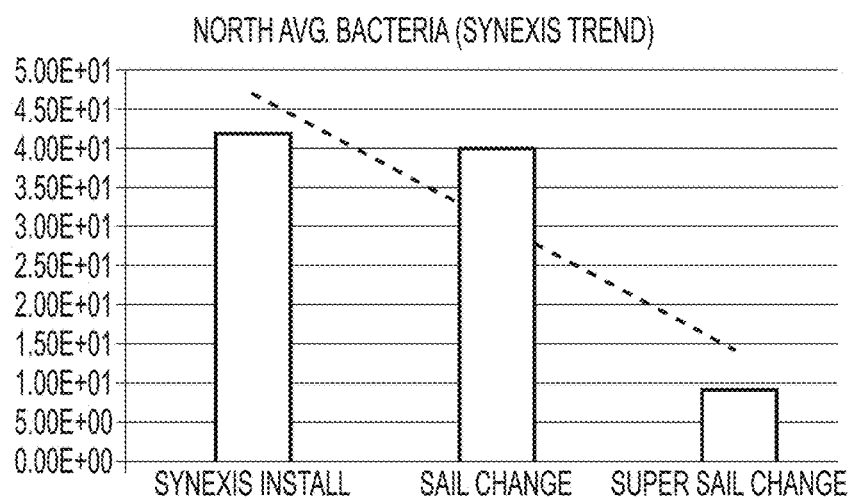
Figure 10C:
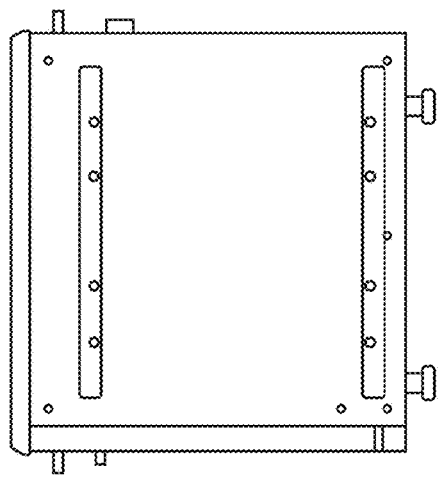
FIGS. 10A-E are views of a stand-alone DHP gas generating device according to the present disclosure.
Figure 10B:
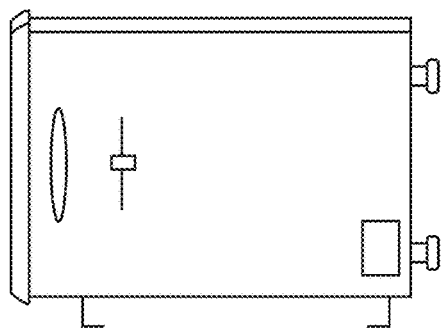
Figure 10A:
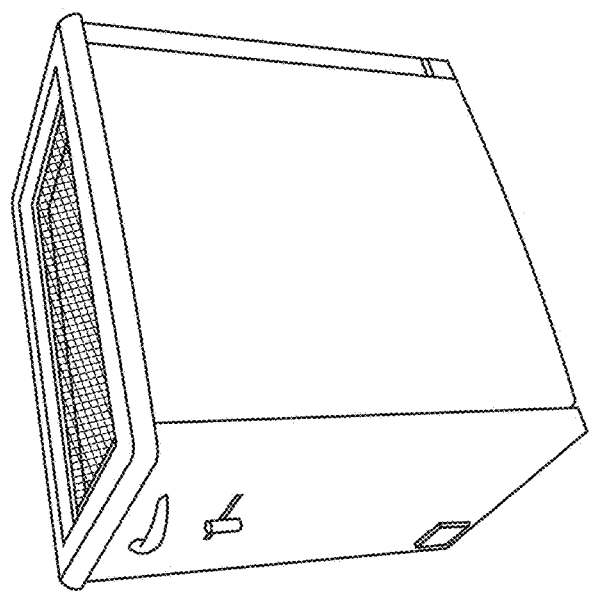
Figure 10E:
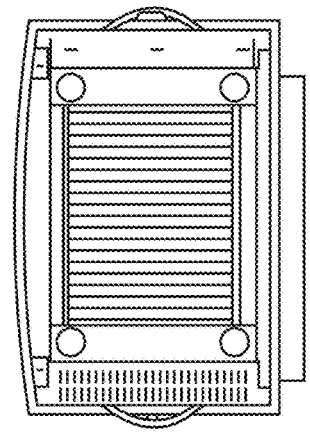
Figure 10D:
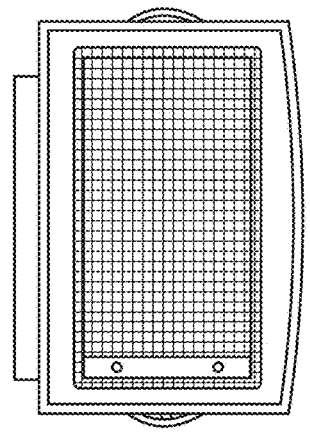

As shown in FIG. 8A, an air-recirculation system 100 includes an air-intake 101 that draws air from the incubator cabinet using a fan 103. The intake air is passed through a filter 102 and fan 103 and directed via a housing 110 through perforated plate 104, through substrate structure 106, and returned to the incubator through air outlet 107. As shown in FIG. 8A, the air-recirculation system 100 includes UV bulbs 105 that illuminate the substrate structure 106 having a catalyst on its surface. Patent Publication No. WO2010/093796 and International Patent Publication No. WO 2015/171633 describe suitable substrate structures 106 and catalysts. The humidified air reacts on the surface of the substrate structure to generate PHPG that is returned to the incubator via air outlet 107. Air-recirculation system 100 or the incubator itself further incudes a device for measuring the levels of PHPG in the incubator and for modifying the air-flow within the air-recirculation system 100 to maintain optimal levels of DHP during the incubation period. A side view of air-recirculation system 100 is presented in FIG. 8B showing the air-intake 101, filter 102, fan 103, plate 104, UV bulbs 105, substrate structure 106, and air outlet 107. FIG. 8C presents a view of an air-recirculation system 100 from inside an incubator showing air-intake 101, and air outlet 107, all contained in enclosure 110. FIG. 8D presents an external view of the housing 110.

Example 14: Effect of DHP on the Microbial Load on Eggs

To determine the effectiveness and safety of DHP on eggs, an initial study is performed to measure microbial loads on commercial hatching eggs. As a control, sixty (60) commercial eggs are placed into a biosafety cabinet with the window closed. This isolates the eggs from exposure to DHP. A test room is prepared by pre-treating the room with DHP for a week using a stand-alone DHP generator (FIG. 9A-E). Sixty (60) commercial hatching eggs (test eggs) are placed in the room and both the control and test eggs are sampled, 10 eggs each, four times over the course of five (5) days at 0 hours, 24 hours, 72 hours, and 120 hours. The level of DHP is maintained at about 0.1 ppm.

For sampling, individual eggs are placed in Whirl-Pak bags containing 10 milliliters (ml) of tryptic soy broth and manually rubbed in bag for 1 minute each. The washed eggs are discarded. One (1) ml from each sample is transferred to a deep well plate in triplicate and 10 fold serial dilutions performed with tryptic soy broth to $10^{-11}$ dilution. The deep well plates are incubated for 24 hours at 37° C. After incubation, 5 microliters (5 μl) of each well is stamped onto a 96-well plate containing either tryptic soy agar (TSA) or MacConkey (Macx) agar. TSA agar is a non-selective, general purpose media. Macx agar is a selective, differential culture media for Gram-negative enteric bacilli. The agar plates are incubated 24 hours at 37° C. and then scored for bacterial growth.

Bacterial growth is scored using a Most Probable Number (MPN) calculation. The results are presented in FIGS. 10A-D. As shown in FIGS. 10A-D, the number of bacteria growing on TSA is significantly reduced after 72 (P=0.05) and 120 hours (P=0.05).

A similar experiment is performed under egg cooler conditions. To provide DHP, a stand-alone device is placed into the egg cooler next to the egg rack and two devices are placed outside of the cooler. For control, the experiment is repeated with all of three DHP generating devices turned off. In this experiment, 300 commercial eggs are placed in the cooler and twenty (20) eggs are sampled, four times over five (5) days at 0 hours, 24 hours, 72 hours, and 120 hours as described above. In addition to the TSA and Mac plates, Xylose Lysine Tergitol-4 (XLT-4) agar plates are included to test for salmonellae. To enrich the sample for *Salmonella*, after removing a first 1 ml sample for serial dilution, tetrathionate and iodine are added to the bags and the bags are incubated for 24 hours at 40° C. The results of the second trial are shown in FIG. 11.

Figure 11A:
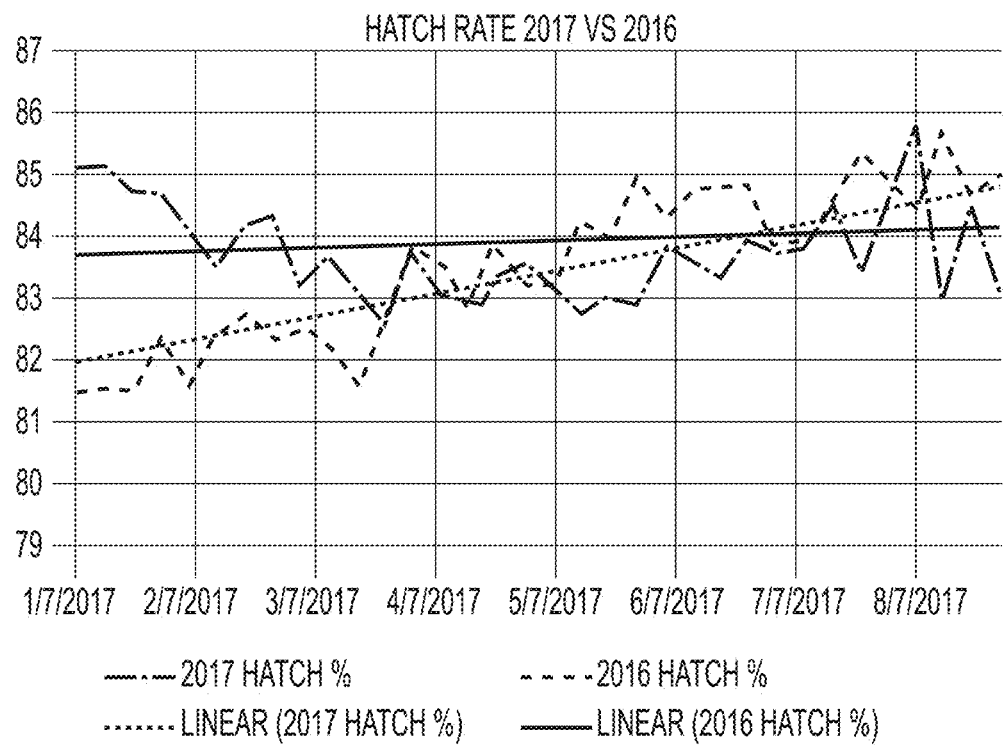
FIGS. 11A-B are graphs presenting the increase in hatch rate and decrease in one week mortality of eggs incubated in the presence or absence of DHP gas according to an embodiment of the present disclosure.
Figure 11B:
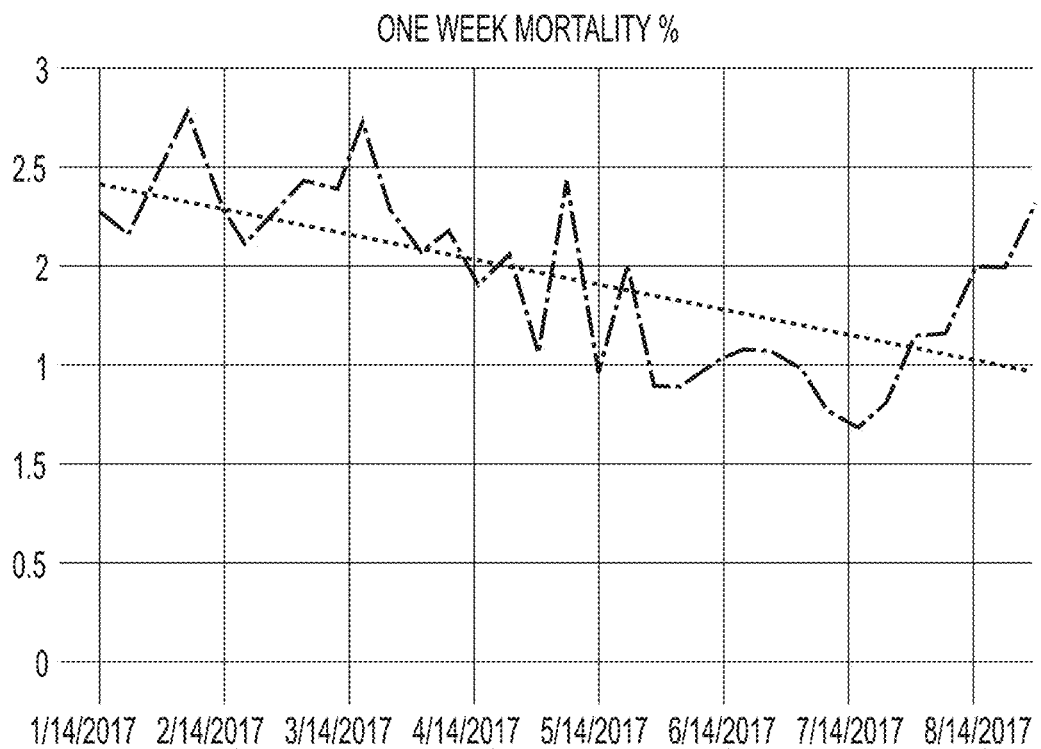
Figure 12:
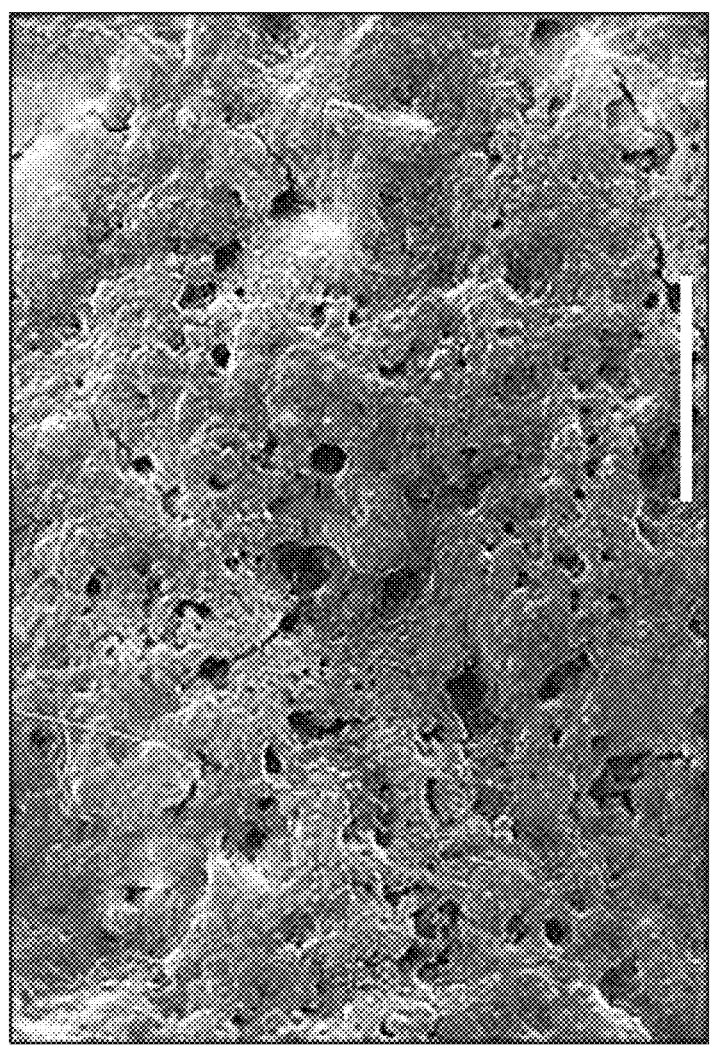
FIG. 12 is a scanning electron micrograph of a chicken egg shell showing its porous, gas permeable surface.
Figure 13A:
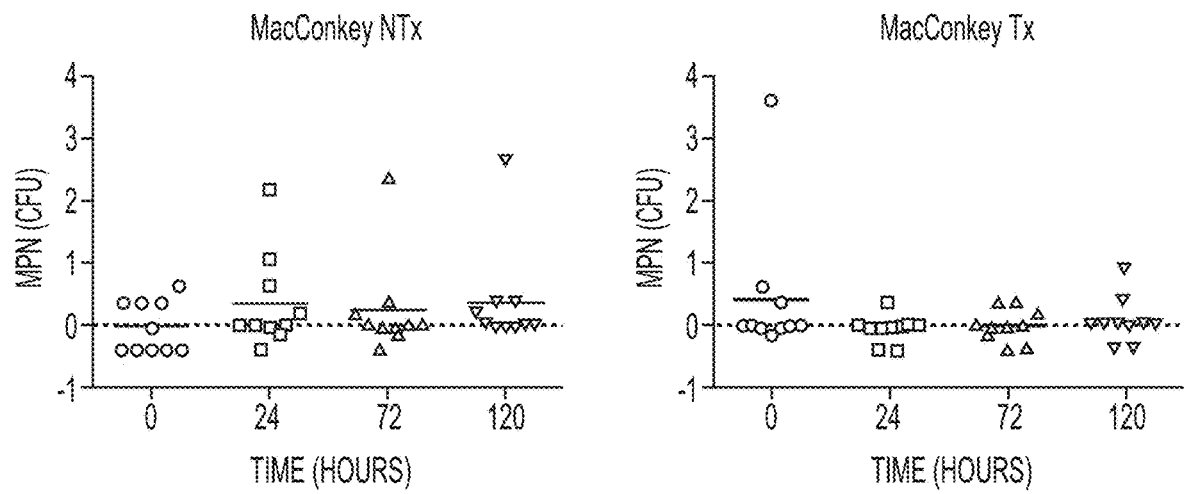
FIGS. 13A-B present graphs showing the effects of DHP gas treatment of eggs on the number and type of bacteria recovered from the surface according to an embodiment of the present disclosure.
Figure 13B:
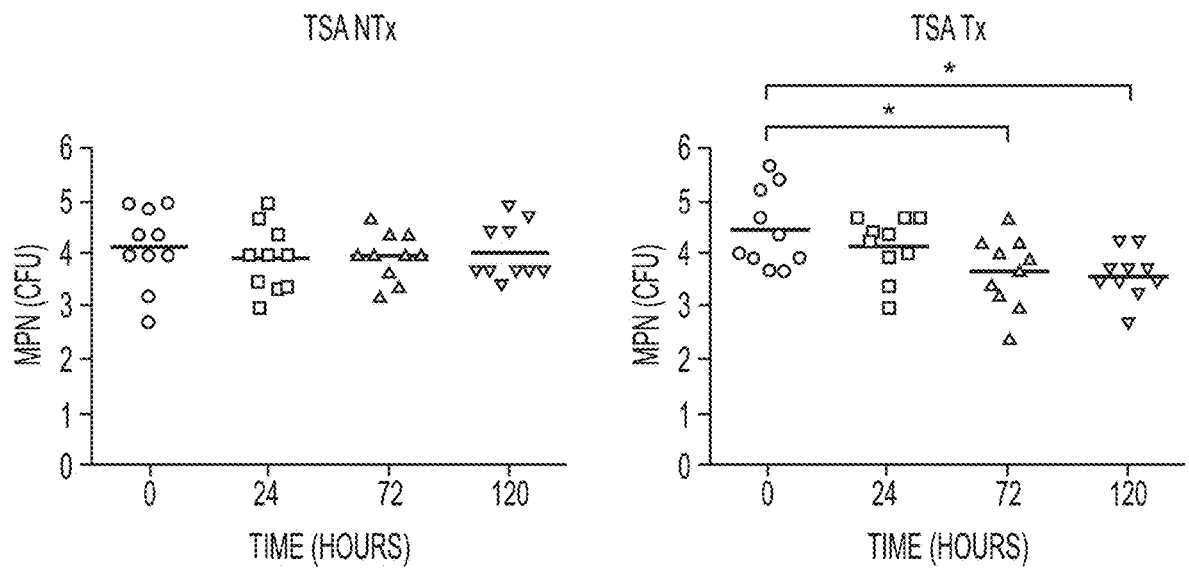
Figure 14A:
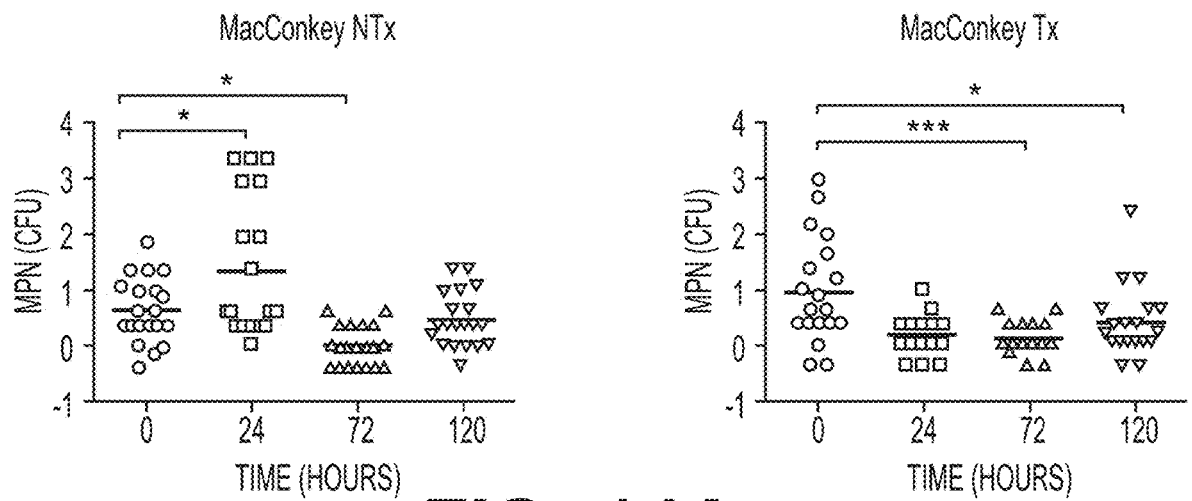
FIGS. 14A-C present graphs of studies of the effects of DHP gas treatment of eggs on the number and type of bacteria recovered from the egg surface according to an embodiment of the present disclosure.
Figure 14B:
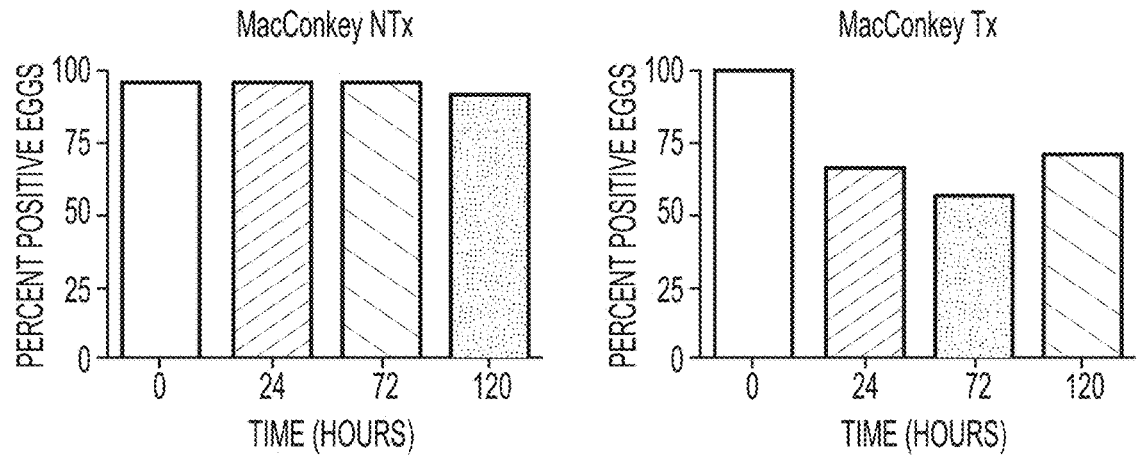
Figure 14C:
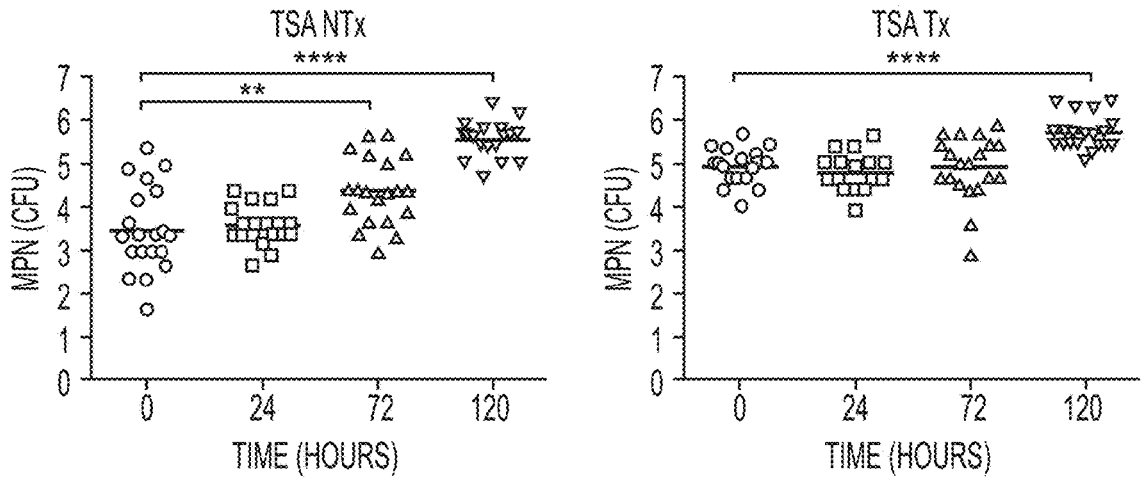

As shown in FIG. 11, for the non-treated group there is significantly more growth on Mac at 24 hours vs. 0 hours (p=0.05) but significantly less growth on Mac at 72 hours compared to 0 hours (p=0.05). In the non-treated group there is significantly more growth on TSA at 72 hours compared to 0 hours (p=0.01) and at 120 hours compared to 0 hours (p=0.0001). In the treated group there is significantly less growth on Mac at 72 hours compared to 0 hours (p=0.001) and at 120 hours compared to 0 hours (p=0.05). In the treated group there is significantly more growth on Mac at 120 hours compared to 0 hours (p=0.0001). No growth of *Salmonella* on the XLT-4 is detected during the trial. The treatment keeps TSA growth static until 120 hours when it starts to increase in number and keeps Mac growth low throughout. The non-treated group has increased growth on TSA at each time-point and Mac growth is low throughout with some fluctuations.

Example 15: Application of DHP Technology to on Farm Egg Rooms

Bacterial contamination of eggs poses a significant risk during incubation. So called ROTS or rotten eggs can explode when warmed to incubation temperatures and contaminate an entire incubator together with the other eggs. Thus, a single ROT can lead to the loss of thousands of eggs and a further expense of cleaning the incubator itself. Accordingly, even small decreases in ROTS provide significant reductions in costs due to lost production time, cleanup, and destruction of otherwise viable eggs.

DHP technology was applied to an on-farm egg room in 2017 and the quality of the eggs assessed. A single stand-alone unit (FIG. 9A-E) is installed in an on-farm egg room having a volume of approximately 50 cubic meters. The temperature is maintained at between about 15° C. to 21° C. Eggs for both the pre- and post-DHP treated rooms are obtained from similarly aged flocks (about 45 week). Newly laid, dry eggs are collected, lightly brushed and placed in the egg room within about thirty minutes of laying. Additional eggs are added to the egg room at approximately two hour intervals. Eggs are stored in the egg room between about 24 and 72 hours and then shipped by truck. Approximately 200,000 to 600,000 eggs are processed through the on-farm egg room (about $1.4 \times 10^6$ eggs/per week).

DHP is provided to the egg room at a concentration of about 0.25 ppm as determined by the Draeger method (See International Patent Publication Nos. WO 2015/171633 and WO 2009/021108). The substrate structure, referred to as the 'sail', is monitored and changed as appropriate. During the course of the studies, an improved sail having an increased amount of catalyst is provided (e.g., the "supersail").

Eggs are monitored for "ROT" rates using standard methods and the results are presented below in Tables 12 and 13 and summarized in Tables 14 and 15. As shown in both tables 14 and 15, DHP treatment results in a decrease in the average percentage of rotten eggs, from 0.44% to 0.29% as shown in Table 12 and from 0.75% to 0.36% in Table 13. The decrease is shown to be statistically significant using Student's t-test (one tailed; homoscedastic variance).

TABLE 13

On Farm Egg Room pre-treatment results

| Rec Date | Quantity | Set Quantity | Hatched | Hatch % | ROTS | Pre-Treatment ROT % |
|---|---|---|---|---|---|---|
| May 10, 2016 | 20160 | 20160 | 16560 | 82.14% | 49 | 0.24% |
| May 13, 2016 | 10080 | 10080 | 8415 | 83.48% | 45 | 0.45% |
| May 17, 2016 | 15120 | 15120 | 12548 | 82.99% | 39 | 0.26% |
| May 20, 2016 | 15120 | 15120 | 12302 | 81.36% | 12 | 0.08% |
| May 24, 2016 | 15120 | 15120 | 12400 | 82.01% | 45 | 0.30% |
| May 27, 2016 | 10080 | 10080 | 8042 | 79.78% | 0 | 0.00% |
| May 31, 2016 | 15120 | 15120 | 12003 | 79.38% | 58 | 0.38% |
| Jun. 3, 2016 | 10080 | 10080 | 7695 | 76.34% | 44 | 0.44% |
| Jun. 7, 2016 | 20160 | 20160 | 15021 | 74.51% | 108 | 0.54% |
| Jun. 10, 2016 | 10080 | 10080 | 7452 | 73.93% | 42 | 0.42% |
| Jun. 14, 2016 | 10080 | 10080 | 7413 | 73.54% | 53 | 0.53% |
| Jun. 17, 2016 | 15120 | 15120 | 11218 | 74.19% | 76 | 0.50% |
| Jun. 21, 2016 | 15120 | 15120 | 10770 | 71.23% | 105 | 0.69% |
| Jun. 24, 2016 | 5040 | 5040 | 3472 | 68.89% | 33 | 0.65% |
| Jun. 28, 2016 | 15120 | 15120 | 10356 | 68.49% | 105 | 0.69% |
| Jul. 1, 2016 | 10080 | 10080 | 6654 | 66.01% | 0 | 0.00% |
| Jul. 5, 2016 | 15120 | 15120 | 10032 | 66.35% | 110 | 0.73% |
| Jul. 7, 2016 | 5040 | 5040 | 3348 | 66.43% | 8 | 0.16% |
| Jul. 8, 2016 | 5040 | 5040 | 3309 | 65.65% | 24 | 0.48% |
| Jul. 11, 2016 | 10080 | 10080 | 6580 | 65.28% | 32 | 0.32% |
| Jul. 15, 2016 | 10080 | 10080 | 6229 | 61.80% | 19 | 0.19% |
| Jul. 17, 2016 | 5040 | 5040 | 3027 | 60.06% | 13 | 0.26% |
| Jul. 18, 2016 | 5040 | 5040 | 3018 | 59.88% | 81 | 1.61% |
| Jul. 21, 2016 | 10080 | 10080 | 6222 | 61.73% | 268 | 2.66% |
| Jul. 26, 2016 | 15120 | 15120 | 8341 | 55.17% | 120 | 0.79% |
| Jul. 29, 2016 | 5040 | 5040 | 2783 | 55.22% | 15 | 0.30% |
| Aug. 2, 2016 | 15120 | 15120 | 8144 | 53.86% | 41 | 0.27% |

TABLE 14

On Farm Egg Room treatment results

| Rec Date | Quantity | Set Quantity | Hatched | Hatch % | ROTS | Pre-Treatment ROT % |
|---|---|---|---|---|---|---|
| May 9, 2017 | 15120 | 15120 | 12340 | 81.61% | 37 | 0.24% |
| May 12, 2017 | 15120 | 15120 | 12245 | 80.99% | 29 | 0.19% |
| May 16, 2017 | 10080 | 10080 | 8093 | 80.29% | 46 | 0.46% |
| May 19, 2017 | 15120 | 15120 | 11796 | 78.02% | 22 | 0.15% |
| May 21, 2017 | 5040 | 5040 | 4083 | 81.01% | 30 | 0.60% |
| May 23, 2017 | 5040 | 5040 | 3958 | 78.53 | 16 | 0.32% |
| May 24, 2017 | 5040 | 5040 | 4092 | 81.19 | 21 | 0.42% |
| May 26, 2017 | 10080 | 10080 | 7934 | 78.71 | 27 | 0.27% |
| May 28, 2017 | 5040 | 5040 | 2879 | 57.12 | 21 | 0.42% |
| May 30, 2017 | 5040 | 5040 | 3872 | 76.83 | 1 | 0.02% |
| Jun. 3, 2017 | 15120 | 15120 | 11373 | 75.22 | 27 | 0.18% |
| Jun. 6, 2017 | 10080 | 10080 | 7665 | 76.04 | 37 | 0.37% |
| Jun. 9, 2017 | 10080 | 10080 | 7585 | 75.25 | 17 | 0.17% |
| Jun. 13, 2017 | 15120 | 15120 | 10644 | 70.40 | 63 | 0.42% |
| Jun. 16, 2017 | 10080 | 10080 | 7041 | 69.85 | 16 | 0.16% |
| Jun. 20, 2017 | 15120 | 15120 | 10358 | 68.51 | 36 | 0.24% |
| Jun. 23, 2017 | 10080 | 10080 | 7336 | 72.78 | 10 | 0.10% |
| Jun. 27, 2017 | 10080 | 10080 | 6640 | 65.87 | 56 | 0.56% |
| Jun. 30, 2017 | 10080 | 10080 | 6684 | 66.31 | 13 | 0.13% |
| Jul. 4, 2017 | 15120 | 15120 | 9705 | 64.19 | 45 | 0.30% |
| Jul. 7, 2017 | 5040 | 5040 | 3261 | 64.70 | 7 | 0.14% |
| Jul. 11, 2017 | 15120 | 15120 | 9156 | 60.56 | 73 | 0.48% |
| Jul. 14, 2017 | 10080 | 10080 | 6677 | 66.24 | 55 | 0.55% |
| Jul. 18, 2017 | 10080 | 10080 | 6983 | 69.28 | 15 | 0.15% |
| Jul. 21, 2017 | 10080 | 10080 | 6791 | 67.37 | 40 | 0.40% |
| Jul. 25, 2017 | 10080 | 10080 | 6703 | 66.50 | 82 | 0.81% |
| Jul. 28, 2017 | 10080 | 10080 | 6458 | 64.07 | 41 | 0.41% |

TABLE 15

Percentage ROT per egg room cycle

| Pre-DHP (2016) | Post DHP (2017) |
|---|---|
| 0.24 | 0.24 |
| 0.45 | 0.19 |
| 0.26 | 0.46 |
| 0.08 | 0.15 |
| 0.3 | 0.6 |
| n/a | 0.32 |
| 0.38 | 0.42 |
| 0.44 | 0.27 |
| 0.54 | 0.42 |
| 0.42 | 0.02 |
| 0.53 | 0.18 |
| 0.5 | 0.37 |
| 0.69 | 0.17 |
| 0.65 | 0.42 |
| 0.69 | 0.16 |
| Average 0.4407 | Average 0.2927 |
| | P = 0.022 |

TABLE 16

Percentage ROT per egg room cycle (improved substrate structure)

| Pre-DHP (2016) | Post DHP (2017) |
|---|---|
| 0.1480 | n/a |
| n/a | 0.24 |
| 0.73 | 0.1 |
| 0.16 | 0.56 |
| 0.48 | 0.13 |
| 0.32 | 0.3 |
| 0.19 | 0.14 |
| 0.26 | 0.48 |
| 1.61 | 0.55 |
| 2.66 | 0.15 |
| 0.79 | 0.4 |
| 0.3 | 0.81 |
| n/a | 0.41 |
| Average 0.7500 | Average 0.3558 |
| | P = 0.10 |

In addition, bacterial contamination in the egg room is assessed by placing blood agar plates at three locations in the room (East, North, and West) at 0, 7, and 30 days, and bacterial growth is assessed after 24 hours. As shown in FIGS. 8A to 8C, the average number of bacteria decreases with DHP treatment. The initial increase observed in the West sampling is due to the placement of the plate directly below the air vent. As shown in FIGS. 8A to 8C, the number of bacterial colonies on the blood agar plates decreases from about 70 total to about 30 total during the test period. Not to be limited by theory, it is hypothesized that the overall bacterial load is decreased over time to a new, lower steady state level.

Notably, during testing it is observed that a refrigerant leak "killed" the sail.

Example 16: Application of DHP Technology to Reduce Hatchery Contamination

Hatcheries and chick production facilities are subject to heavy bacterial loads that are difficult to control. In addition to the animals themselves, there is a significant contamination of the facilities from the outside. As shown in REF_Ref502234528 Table 16, DHP treatment reduces bacterial loads in hatcheries by over 90%.

TABLE 17

PHP reduces bacterial loads in the hatchery

| | Pre | Post | Kill | Reduction |
|---|---|---|---|---|
| Total bacteria | 600147 | 50110 | 550037 | 91.65% |
| Aspergillus fumigatus | 5000 | 1 | 49999 | 99.99% |
| Other blue green | 50039 | 56 | 49983 | 99.89% |
| Total | 700186 | 50167 | 650019 | |

Example 17: DHP Treatment During on-Site Storage on Improved Chick Hatching and Chick Weight DHP gas treatment during on-site storage improves the health and quality eggs resulting in an increase of the total percent hatchability and the fertile hatchability. Even further, the average chick weight increases by 0.77 grams (1.7% more than the untreated eggs). Thus, on-site DHP gas treatment prior to incubation is effective. Importantly, the effect of the treatment persists long after the application of DHP gas has ended.

A total of 22 replicates of 90 eggs each of age matched, flock matched eggs are stored prior to incubation for 4 to 7 days in an on-site egg room at about 20° C. (e.g., below physiological zero) either with or without DHP gas. The paired replicates are then incubated to hatching under standard commercial conditions. At hatching, the following parameters are assessed and recorded: Total Hatchability (%), Fertile Hatchability (%),% Infertile, Early dead (%), Mid dead (%), Late dead (%), Cracked (%), Contaminated (%), Live pip (%), Dead pip (%), Cull dead chick (%), Chick Weight (g), Chick A (%), and Chick B (%). The results for the DHP gas treated (DHP+) replicates are presented in REF_Ref503113403 \h Table 17. The results for untreated (DHP-) replicates are presented in REF_Ref503113442 \h Table 18. The results are summarized and compared based on the number of days eggs were stored prior to incubation and shown in REF Ref503113614 \h Table 19.

As shown in Table 19, the chicks show significant improvements in overall health with an increased number of A grade chicks (0.23% improvement). In addition, the chicks are an average of 1.8% heavier (0.77 grams). The effect of DHP gas is increased with longer incubations. Eggs treated four days have slightly less total hatchability (−0.64%) but slightly increased fertile hatchability (+0.12) and increased weight (+0.89 g). An additional day of DHP gas treatment increases total hatchability by 1.3% and fertile hatchability by 3.2% and 0.85 grams increased weight. At six days, DHP gas treatment results in an increase of total hatchability of 2.96% and fertile hatchability of 4.67%, and 0.49 grams increased weight. After a seven day storage in the presence of DHP gas, total hatchability remains increased by 0.56% and fertile hatchability by 0.56%, and 1.10 grams increased weight. These results suggest that five or six days of on-site storage in the presence of DHP gas results in further benefits. In an aspect, treatment with DHP gas can be continued during the incubation and hatching periods to further reduce bacteria and improve the health of the chicks.

Treatment of eggs during on-site storage decreases ROTS (e.g., contaminated eggs at risk of becoming "boomers" or exploding eggs during incubation). As shown in Table 19, while the number of cracked eggs (micro-cracking is considered independent of DHP treatment) is similar between the treated and untreated eggs, at day 7, none of the DHP gas treated eggs is observed to be contaminated. The elimination of ROTS is significant as even a single "boomer" contaminates an entire incubation and results in significant clean-up and lost production.

The overall health of developing chicks is improved by DHP gas treatment during on-site storage as is evident from the death during incubation. Notably, the number of early deaths is decreased by about 1.7% while mid cycle deaths are decreased. In contrast, the number of live pip eggs increases for the DHP gas treated eggs. Not to be limited by theory, it is thought that the improved health provides for more chicks to develop to pipping stage, but the health is insufficiently improved to result in hatching. In contrast, chicks that reach the pipping stage are healthier, thereby decreasing the number of chicks that are unable to hatch. These results suggest a permanent improvement of chick health as a result of DHP gas treatment during on site storage.

TABLE 18

Chick Hatching Data with DHP Treatment

| Rep | Egg storage (days) | Total Hatchblty (%) | Fertile Hatchblty (%) | % Infer | Early dead (%) | Mid dead (%) | Late dead (%) | Crack (%) | Cont (%) | Live pip (%) | Dead pip (%) | Cull dead (%) | Check Weight (g) | Chick A (%) | Chick B (%) |
|---|---|---|---|---|---|---|---|---|---|---|---|---|---|---|---|
| 1 | 4 | 91.01 | 94.19 | 3.37 | 4.44 | 0.00 | 1.11 | 0.00 | 0.00 | 0.00 | 0.00 | 0.00 | 45.68 | 96.30 | 3.70 |
| 2 | 4 | 88.89 | 93.02 | 4.44 | 4.44 | 0.00 | 1.11 | 0.00 | 0.00 | 1.11 | 0.00 | 0.00 | 45.25 | 96.25 | 3.75 |
| 3 | 6 | 94.44 | 95.51 | 1.11 | 2.22 | 0.00 | 2.22 | 0.00 | 0.00 | 0.00 | 0.00 | 0.00 | 44.65 | 97.65 | 2.35 |
| 4 | 6 | 96.67 | 96.67 | 0.00 | 2.22 | 1.11 | 0.00 | 0.00 | 0.00 | 0.00 | 0.00 | 0.00 | 44.71 | 98.85 | 1.15 |
| 5 | 5 | 96.67 | 97.75 | 1.11 | 2.22 | 0.00 | 0.00 | 0.00 | 0.00 | 0.00 | 0.00 | 0.00 | 43.79 | 98.85 | 1.15 |
| 6 | 5 | 93.33 | 95.45 | 2.22 | 1.11 | 0.00 | 2.22 | 0.00 | 0.00 | 1.11 | 0.00 | 0.00 | 44.29 | 100.0 | 0.00 |
| 7 | 7 | 94.44 | 95.51 | 1.11 | 1.11 | 0.00 | 2.22 | 0.00 | 0.00 | 0.00 | 0.00 | 1.11 | 44.94 | 96.47 | 3.53 |
| 8 | 7 | 94.44 | 94.44 | 0.00 | 1.11 | 1.11 | 1.11 | 0.00 | 0.00 | 2.22 | 0.00 | 0.00 | 44.41 | 97.65 | 2.35 |
| 9 | 6 | 90.00 | 93.10 | 3.33 | 3.33 | 0.00 | 3.33 | 0.00 | 0.00 | 0.00 | 0.00 | 0.00 | 44.44 | 98.77 | 1.23 |
| 10 | 4 | 92.22 | 93.26 | 1.11 | 2.22 | 0.00 | 3.33 | 0.00 | 0.00 | 1.11 | 0.00 | 0.00 | 44.70 | 97.60 | 2.40 |
| 11 | 6 | 93.33 | 94.38 | 1.11 | 2.22 | 2.22 | 1.11 | 0.00 | 0.00 | 0.00 | 0.00 | 0.00 | 43.75 | 96.43 | 3.57 |
| 12 | 6 | 86.67 | 92.86 | 6.67 | 2.22 | 1.11 | 3.33 | 0.00 | 0.00 | 0.00 | 0.00 | 0.00 | 44.23 | 96.16 | 3.84 |
| 13 | 5 | 92.22 | 95.40 | 3.33 | 1.11 | 1.11 | 2.22 | 0.00 | 0.00 | 0.00 | 0.00 | 0.00 | 43.86 | 97.60 | 2.40 |
| 14 | 5 | 85.56 | 95.06 | 10.00 | 2.22 | 2.22 | 0.00 | 0.00 | 0.00 | 0.00 | 0.00 | 0.00 | 43.90 | 98.70 | 1.30 |
| 15 | 4 | 88.89 | 90.91 | 2.22 | 5.55 | 0.00 | 2.22 | 1.11 | 0.00 | 0.00 | 0.00 | 0.00 | 43.44 | 98.75 | 1.25 |
| 16 | 4 | 92.22 | 96.51 | 4.44 | 3.33 | 0.00 | 0.00 | 0.00 | 0.00 | 0.00 | 0.00 | 0.00 | 44.76 | 95.20 | 4.80 |
| 17 | 6 | 91.11 | 93.18 | 2.22 | 2.22 | 1.11 | 3.33 | 0.00 | 0.00 | 0.00 | 0.00 | 0.00 | 43.54 | 95.13 | 4.87 |
| 18 | 6 | 92.22 | 93.26 | 1.11 | 4.44 | 0.00 | 1.11 | 0.00 | 0.00 | 1.11 | 0.00 | 0.00 | 44.76 | 95.20 | 4.80 |
| 19 | 5 | 90.00 | 95.29 | 5.56 | 1.11 | 1.11 | 2.22 | 0.00 | 0.00 | 0.00 | 0.00 | 0.00 | 45.12 | 97.54 | 2.46 |
| 20 | 5 | 88.89 | 93.02 | 4.44 | 3.33 | 1.11 | 0.00 | 0.00 | 0.00 | 2.22 | 0.00 | 0.00 | 44.81 | 97.50 | 2.50 |
| 21 | 4 | 82.22 | 83.15 | 1.11 | 6.66 | 1.11 | 4.44 | 0.00 | 0.00 | 4.44 | 0.00 | 0.00 | 44.19 | 95.95 | 4.05 |
| 22 | 4 | 94.44 | 94.44 | 0.00 | 2.22 | 0.00 | 0.00 | 2.22 | 0.00 | 0.00 | 1.11 | 0.00 | 44.82 | 98.83 | 1.17 |
| Mean |  | 91.36 | 93.93 | 2.73 | 2.78 | 0.61 | 1.67 | 0.15 |  | 0.61 | 0.05 | 0.05 | 44.46 | 97.34 | 2.66 |

TABLE 19

Chick Hatching Data without DHP Treatment

| Rep | Egg storage (days) | Total Hatchblty (%) | Fertile Hatchblty (%) | % Infer | Early dead (%) | Mid dead (%) | Late dead (%) | Crack (%) | Cont (%) | Live pip (%) | Dead pip (%) | Cull dead (%) | Check Weight (g) | Chick A (%) | Chick B (%) |
|---|---|---|---|---|---|---|---|---|---|---|---|---|---|---|---|
| 1 | 4 | 93.33 | 95.45 | 2.22 | 3.33 | 0.00 | 1.11 | 0.00 | 0.00 | 0.00 | 0.00 | 0.00 | 44.46 | 96.43 | 3.57 |
| 2 | 4 | 92.13 | 94.25 | 2.25 | 4.49 | 0.00 | 0.00 | 0.00 | 0.00 | 1.12 | 0.00 | 0.00 | 43.84 | 98.78 | 1.22 |
| 3 | 5 | 83.33 | 89.29 | 6.67 | 3.33 | 0.00 | 6.67 | 0.00 | 0.00 | 0.00 | 0.00 | 0.00 | 43.73 | 94.67 | 5.33 |
| 4 | 5 | 90.00 | 92.05 | 2.22 | 2.22 | 0.00 | 4.44 | 0.00 | 0.00 | 0.00 | 1.11 | 0.00 | 43.56 | 95.06 | 4.94 |
| 5 | 6 | 91.11 | 90.91 | 2.22 | 4.44 | 0.00 | 1.11 | 0.00 | 0.00 | 0.00 | 1.11 | 0.00 | 43.38 | 96.25 | 3.75 |
| 6 | 6 | 87.78 | 88.76 | 1.11 | 7.78 | 0.00 | 3.33 | 0.00 | 0.00 | 0.00 | 0.00 | 0.00 | 43.35 | 100.00 | 0.00 |
| 7 | 7 | 94.44 | 95.51 | 1.11 | 4.44 | 0.00 | 0.00 | 0.00 | 0.00 | 0.00 | 0.00 | 0.00 | 43.76 | 97.65 | 2.35 |
| 8 | 7 | 93.33 | 93.33 | 0.00 | 3.33 | 0.00 | 2.22 | 0.00 | 1.11 | 0.00 | 0.00 | 0.00 | 43.39 | 98.81 | 1.19 |
| 9 | 4 | 90.00 | 93.10 | 3.33 | 5.56 | 0.00 | 1.11 | 0.00 | 0.00 | 0.00 | 0.00 | 0.00 | 43.21 | 93.83 | 6.17 |
| 10 | 4 | 92.22 | 93.26 | 1.11 | 2.22 | 0.00 | 4.44 | 0.00 | 0.00 | 0.00 | 0.00 | 0.00 | 44.46 | 97.59 | 2.41 |
| 11 | 5 | 92.13 | 92.13 | 0.00 | 3.37 | 0.00 | 4.49 | 0.00 | 0.00 | 0.00 | 0.00 | 0.00 | 42.74 | 97.56 | 2.44 |
| 12 | 5 | 92.13 | 95.35 | 3.37 | 1.12 | 0.00 | 1.12 | 1.12 | 0.00 | 0.00 | 1.12 | 0.00 | 42.26 | 97.56 | 2.44 |
| 13 | 6 | 88.89 | 88.76 | 1.11 | 2.22 | 1.11 | 5.56 | 0.00 | 0.00 | 0.00 | 1.11 | 1.11 | 43.10 | 100.00 | 0.00 |
| 14 | 6 | 87.78 | 88.76 | 1.11 | 7.78 | 0.00 | 1.11 | 0.00 | 0.00 | 2.22 | 0.00 | 0.00 | 44.36 | 96.20 | 3.80 |
| 15 | 6 | 89.29 | 90.36 | 1.19 | 7.14 | 0.00 | 2.38 | 0.00 | 0.00 | 0.00 | 0.00 | 0.00 | 43.73 | 97.33 | 2.67 |
| 16 | 4 | 91.11 | 92.13 | 1.11 | 4.44 | 0.00 | 2.22 | 0.00 | 0.00 | 0.00 | 1.11 | 0.00 | 43.48 | 96.34 | 3.66 |
| 17 | 4 | 86.67 | 86.52 | 1.11 | 6.67 | 0.00 | 3.33 | 1.11 | 0.00 | 0.00 | 1.11 | 0.00 | 44.22 | 97.40 | 2.60 |
| 18 | 4 | 88.89 | 89.89 | 1.11 | 4.44 | 0.00 | 4.44 | 0.00 | 0.00 | 1.11 | 0.00 | 0.00 | 42.94 | 97.50 | 2.50 |
| 19 | 5 | 89.77 | 91.86 | 2.27 | 5.68 | 0.00 | 1.14 | 0.00 | 0.00 | 1.14 | 0.00 | 0.00 | 44.30 | 96.20 | 3.80 |
| 20 | 5 | 91.11 | 92.13 | 1.11 | 5.56 | 1.11 | 1.11 | 0.00 | 0.00 | 0.00 | 0.00 | 0.00 | 44.09 | 98.78 | 1.22 |
| 21 | 6 | 87.78 | 86.67 | 0.00 | 6.67 | 0.00 | 4.44 | 0.00 | 0.00 | 0.00 | 0.00 | 1.11 | 44.68 | 94.87 | 5.13 |
| 22 | 6 | 91.11 | 92.05 | 2.22 | 2.22 | 1.11 | 2.22 | 0.00 | 0.00 | 0.00 | 1.11 | 1.11 | 44.07 | 97.53 | 2.47 |
| Mean |  | 90.20 | 91.48 | 1.73 | 4.48 | 0.15 | 2.64 | 0.10 | 0.05 | 0.25 | 0.35 | 0.15 | 43.69 | 97.11 | 2.89 |

TABLE 20

Summary of Effects of DHP on Hatching Incubation

|  | Day 4 DHP+ | Day 4 DHP− | 4 day delta | Day 5 DHP+ | Day 5 DHP− | 5 day delta | Day 6 DHP+ | Day 6 DHP− | 6 day delta | Day 7 DHP+ | Day 7 DHP− | Day 7 Delta | Avg. Trtd | Avg. Untrd | Delta |
|---|---|---|---|---|---|---|---|---|---|---|---|---|---|---|---|
| Total Hatchability (%) | 89.99 | 90.62 | −0.64 | 91.11 | 89.75 | 1.36 | 92.06 | 89.10 | 2.96 | 94.44 | 93.89 | 0.56 | 91.36 | 90.20 | 1.16 |
| Fertile Hatchability (%) | 92.21 | 92.09 | 0.12 | 95.33 | 92.14 | 3.20 | 94.14 | 89.47 | 4.67 | 94.98 | 94.42 | 0.56 | 93.93 | 91.48 | 2.45 |
| % Infertile | 2.39 | 1.75 | 0.64 | 4.44 | 2.61 | 1.84 | 2.22 | 1.28 | 0.94 | 0.56 | 0.56 | 0.00 | 2.73 | 1.73 | 1.00 |
| Early dead (%) | 4.12 | 4.45 | −0.33 | 1.85 | 3.55 | −1.70 | 2.70 | 5.46 | −2.77 | 1.11 | 3.89 | −2.78 | 2.78 | 4.48 | −1.70 |
| Mid dead (%) | 0.16 | 0.00 | 0.16 | 0.93 | 0.19 | 0.74 | 0.79 | 0.32 | 0.48 | 0.56 | 0.00 | 0.56 | 0.61 | 0.15 | 0.45 |
| Late dead (%) | 1.74 | 2.38 | −0.64 | 1.11 | 3.16 | −2.05 | 2.06 | 2.88 | −0.82 | 1.67 | 1.11 | 0.55 | 1.67 | 2.64 | −0.97 |
| Crack (%) | 0.48 | 0.16 | 0.32 | 0.00 | 0.19 | −0.19 | 0.00 | 0.00 | 0.00 | 0.00 | 0.00 | 0.00 | 0.15 | 0.10 | 0.05 |
| Cont(%) | 0.00 | 0.00 | 0.00 | 0.00 | 0.00 | 0.00 | 0.00 | 0.00 | 0.00 | 0.00 | 0.56 | −0.56 | 0.00 | 0.05 | −0.05 |
| Live pip (%) | 0.95 | 0.32 | 0.63 | 0.56 | 0.19 | 0.37 | 0.16 | 0.32 | −0.16 | 1.11 | 0.00 | 1.11 | 0.61 | 0.25 | 0.35 |
| Dead pip (%) | 0.16 | 0.32 | −0.16 | 0.00 | 0.37 | −0.37 | 0.00 | 0.48 | −0.48 | 0.00 | 0.00 | 0.00 | 0.05 | 0.35 | −0.30 |
| Cull dead cks (%) | 0.00 | 0.00 | 0.00 | 0.00 | 0.00 | 0.00 | 0.00 | 0.48 | −0.48 | 0.56 | 0.00 | 0.56 | 0.05 | 0.15 | −0.10 |
| Chick Weight (g) | 44.69 | 43.80 | 0.89 | 44.29 | 43.45 | 0.85 | 44.30 | 43.81 | 0.49 | 44.68 | 43.58 | 1.10 | 44.46 | 43.69 | 0.77 |
| Chick A (%) | 96.98 | 96.84 | 0.14 | 98.37 | 96.64 | 1.73 | 96.88 | 97.46 | −0.57 | 97.06 | 98.23 | −1.17 | 97.34 | 97.11 | 0.23 |
| Chick B (%) | 3.02 | 3.16 | −0.14 | 1.64 | 3.36 | −1.73 | 3.12 | 2.54 | 0.57 | 2.94 | 1.77 | 1.17 | 2.66 | 2.89 | −0.23 |

Example 18: Stand-Alone DHP Generating Device

A stand-alone DHP gas generating device comprising a filter 110, a fan assembly 120, a housing 130, and a DHP gas generating system 140 is shown in FIGS. 15 to 19.

The invention claimed is:

1. A method for improving poultry production by treatment of eggs in a hatchery with dry hydrogen peroxide (DHP) gas, the method comprising:
   (a) placing poultry eggs into an egg storage room at the hatchery, wherein the egg storage room is maintained at a first relative humidity;
   (b) storing at least a portion of the poultry eggs in the egg storage room for a storage period, wherein the temperature of the egg storage room during the storage period is below physiological zero;
   (c) transferring at least a portion of the poultry eggs from the egg storage room to an incubation room;
   (d) incubating the poultry eggs in an incubator for an incubation period, wherein the incubating is carried out at a temperature of at least 37° C. and a second relative humidity lower than the first relative humidity in the egg storage room, wherein the incubator is located in a protected area of the incubation room, wherein said protected area reduces an exchange of air with an environment outside the incubation room to prevent dilution of the DHP;
   (e) during the incubating, continuously treating the poultry eggs with DHP at a concentration in the range of from 0.001 ppm to 10 ppm to provide treated eggs; and
   (f) hatching at least a portion of the treated eggs to provide a plurality of chicks.

2. The method of claim 1, wherein the storage period is between 1 and 7.

3. The method of claim 1, wherein the DHP gas is provided directly into the incubator.

4. The method of claim 1, wherein during the storing, at least a portion of the poultry eggs are provided short periods of incubation during egg storage (SPIDES).

5. The method of claim 1, wherein the storage period is between 1 and 8 hours.

6. The method of claim 1, wherein at least one of the following improvements (i) through (vii) is exhibited as a result of performing steps (a) through (f) (i) an increase in hatchability, (ii) an increase in uniformity, (iii) an increase in average chick hatching weight, (iv) a reduction in the number of pipped unhatched eggs, (v) a decrease in the number of second quality chicks, (vi) a reduction in the bacterial load of the poultry eggs by 10 fold, and (vii) a decrease in the 7-day mortality of hatched first quality chicks.

7. The method of claim 1, further comprising during the incubating, continuously treating the poultry eggs with DHP at a concentration in the range of from about 0.001 ppm to 2 ppm.

8. The method of claim 1, further comprising continuously treating the poultry eggs with DHP at a concentration in the range of from 0.001 ppm to 5 ppm during the storage period.

9. The method of claim 8, wherein the poultry eggs are stored in a protected area of the egg storage room during the treating with DHP and wherein the protected area includes curtains to reduce an exchange of air with an environment outside of the egg storage room.

10. The method of claim 1, further comprising during the hatching, treating the plurality of chicks with DHP at a concentration in the range of from 0.001 to 10 ppm.

11. The method of claim 1, wherein the incubator is a setting incubator and wherein the incubating period is in the range of from 1 to 18 days.

12. The method of claim 1, wherein the incubator is a hatching incubator and wherein the incubating period is in the range of from 1 to 5 days.

13. The method of claim 1, wherein the treated eggs have a lower concentration of pathogens than the eggs placed in the egg storage room, wherein the pathogens comprise one or more of *Salmonella* spp., *Enterococcus* spp., *Staphylococcus* spp., *Escherichia* spp., *Streptococci* spp., *Clostridium* spp., Orthomyxoviridae (influenza), Picornaviridae, Retroviridae, Herpesviridae, Hepeviridae, Poxviridae, Parvoviridae, Paramyxoviridae, Reoviridae, *Aspergillus* spp., *Candida* spp., *Fusarium* spp., or *Mycoplasma*.

* * * * *